(12) United States Patent
Satchi-Fainaro et al.

(10) Patent No.: US 8,703,114 B2
(45) Date of Patent: Apr. 22, 2014

(54) CONJUGATE OF A POLYMER, AN ANTI-ANGIOGENESIS AGENT AND A TARGETING MOIETY, AND USES THEREOF IN THE TREATMENT OF BONE RELATED ANGIOGENESIS CONDITIONS

(75) Inventors: Ronit Satchi-Fainaro, Tel-Aviv (IL); Ehud Segal, Ramat-Gan (IL); Jindrich Kopecek, Salt Lake City (IL); Pavla Kopeckova, Salt Lake City, UT (US); Huaizhong Pan, Salt Lake City, UT (US)

(73) Assignees: Ramot at Tel-Aviv University Ltd., Tel-Aviv (IL); University of Utah Research Foundation, Salt Lake City, UT (US)

( * ) Notice: Subject to any disclaimer, the term of this patent is extended or adjusted under 35 U.S.C. 154(b) by 440 days.

(21) Appl. No.: 12/993,855

(22) PCT Filed: May 21, 2009

(86) PCT No.: PCT/IL2009/000511
§ 371 (c)(1),
(2), (4) Date: Nov. 22, 2010

(87) PCT Pub. No.: WO2009/141827
PCT Pub. Date: Nov. 26, 2009

(65) Prior Publication Data
US 2011/0085979 A1     Apr. 14, 2011

Related U.S. Application Data

(60) Provisional application No. 61/193,136, filed on Oct. 30, 2008, provisional application No. 61/071,888, filed on May 22, 2008.

(51) Int. Cl.
*A61K 31/74*    (2006.01)

(52) U.S. Cl.
USPC ............................................. 424/78.17

(58) Field of Classification Search
None
See application file for complete search history.

(56) References Cited

U.S. PATENT DOCUMENTS

| 6,884,817 B2 | 4/2005 | Li et al. |
| 7,803,903 B2 | 9/2010 | Kratz |

(Continued)

FOREIGN PATENT DOCUMENTS

| WO | WO 03/086178 | 10/2003 |
| WO | WO 03/086382 | 10/2003 |

(Continued)

OTHER PUBLICATIONS

Pan et al, Water-soluble HPMA copolymer-prostaglandin E1 conjugates containing a cathepsin K sensitive spacer, Journal of Drug Targeting, 2006, 14(6), 425-435.*

(Continued)

*Primary Examiner* — Paul Dickinson

(57) ABSTRACT

Conjugates of hydroxypropyl methacrylamide (HPMA)-derived copolymers having attached thereto TNP-470 and a high load (e.g., higher than 3 mol %) of alendronate (ALN), and processes of preparing same are disclosed.
Conjugates of polymers or copolymers having attached thereto an anti-angiogenesis agent and an oligoaspartate bone targeting agent, and processes of preparing same, are further disclosed.
Pharmaceutical compositions containing these conjugates and uses thereof in the treatment and monitoring of bone related disorders are also disclosed.

39 Claims, 14 Drawing Sheets
(10 of 14 Drawing Sheet(s) Filed in Color)

(56) References Cited

U.S. PATENT DOCUMENTS

| | | |
|---|---|---|
| 2002/0197261 A1 | 12/2002 | Li et al. |
| 2005/0257114 A1 | 11/2005 | Gorshe |
| 2007/0104719 A1 | 5/2007 | Carter et al. |
| 2008/0279778 A1 | 11/2008 | Van et al. |
| 2010/0022615 A1 | 1/2010 | Fegley et al. |
| 2011/0135618 A1 | 6/2011 | Koch et al. |
| 2011/0286923 A1 | 11/2011 | Satchi-Fainaro et al. |

FOREIGN PATENT DOCUMENTS

| | | |
|---|---|---|
| WO | WO 2004/062588 | 7/2004 |
| WO | WO 2006/012355 | 2/2006 |
| WO | WO 2006/084054 | 8/2006 |
| WO | WO 2007/090094 | 8/2007 |
| WO | WO 2009/141823 | 11/2009 |
| WO | WO 2009/141826 | 11/2009 |
| WO | WO 2009/141827 | 11/2009 |
| WO | WO 2013/132485 | 9/2013 |

OTHER PUBLICATIONS

Official Action Dated Mar. 4, 2013 From the US Patent and Trademark Office Re. U.S. Appl. No. 12/993,856.

Translation of Office Action Dated Sep. 26, 2011 From the State Intellectual Property Office of the People's Republic of China Re. Application No. 200980128587.1.

Restriction Official Action Dated Oct. 11, 2012 From the US Patent and Trademark Office Re. U.S. Appl. No. 12/993,856.

Mitra et al. "Polymeric Conjugates of Mono- and Bi-Cyclic αvβ3 Binding Peptides for Tumor Targeting", Journal of Controlled Release, 114: 175-183, 2006.

Baabur-Cohen et al. "Recent Progress in Polymer Therapeutics as Nanomedicines", Handbook of Harnessing Biomaterials in Nanomedicine: Preparation, Toxicity, and Applications, Chap.4: 77-122, 2012.

Duncan "Polymer Conjugates as Anticancer Nanomedicines", Nature Reviews Cancer, 6: 688-701, Sep. 2006.

Marsili et al. "Interaction of DDSDEEN Peptide With N-CAM Protein. Possible Mechanism Enhancing Neuronal Differentiation", Peptides, 29: 2232-2242, 2008.

Greco et al. "Combination Therapy: Opportunities and Challenges for Polymer-Drug Conjugates as Anticancer Nanomedicines", Advanced Drug Delivery Reviews, 61: 1203-1213, 2009.

Satchi-Fainaro et al. "Synthesis and Characterization of a Catalytic Antibody-HPMA Copolymer-Conjugate as A Tool for Tumor Selective Prodrug Activation", Bioorganic & Medicinal Chemistry, 10(9): 3023-3029, 2002.

International Search Report and the Written Opinion Dated Dec. 2, 2009 From the International Searching Authority Re.: Application No. PCT/IL09/00510.

International Search Report and the Written Opinion Dated Nov. 25, 2009 From the International Searching Authority Re.: Application No. PCT/IL09/00507.

Chen et al. "Synthesis and Biological Evaluation of Dimeric RGD Peptide-Paclitaxel Conjugate as a Model for Integrin-Targeted Drug Delivery", Journal of Medicinal Chemistry, 48: 1098-1106, 2005.

Hrubýet al. "Hydroxybisphosphonate-Containing Polymeric Drug-Delivery Systems Designed for Targeting Into Bone Tissue", Journal of Applied Polymer Science, 101: 3192-3201, 2006.

Meerum Terwogt et al. "Phase I Clinical and Pharmacokinetic Study of PNU166945, A Novel Water-Soluble Polymer-Conjugated Prodrug of Paclitaxel", Anti-Cancer Drug, 12: 315-323, 2001.

Mitra et al. "Comparison of Polymeric Conjugates of Mono- and Bi-Cyclic RGD Peptide for Targeting Tumor Angiogenesis", 2006 National Biotechnology Conference, The AAPS Journal, 8(S1): Abstract 127, 2006. Retrieved From the Internet. § 1, 3-4.

Mitra et al. "Polymer-Peptide Conjugates for Angiogenesis Targeted Tumor Radiotherapy", Nuclear Medicine and Biology, 33: 43-52, 2006.

O'Hare et al. "Polymeric Drug-Carriers Containing Doxorubicin and Melanocyte-Stimulating Hormone: In Vitro and In Vivo Evaluation Against Murine Melanoma", Journal of Drug Targeting, 1: 217-229, 1993.

Satchi-Fainaro et al. "Targeting Angiogenesis With a Conjugate of HPMA Copolymer and TNP-470", Nature Medicine, 10(3): 255-261, Mar. 2004.

Seymour et al. "Hepatic Drug Targeting: Phase I Evaluation of Polymer-Bound Doxorubicin", Journal of Clinical Oncology, 20(6): 1668-1676, Mar. 15, 2002.

Uludag "Bisphosphonates as a Foundation of Drug Delivery to Bone", Current Pharmaceutical Design, 8: 1929-1944, 2002.

Wang et al. "Paclitaxel at Ultra Low Concentrations Inhibits Angiogenesis Without Affecting Cellular Microtube Assembly", Anti-Cancer Drugs, 14: 13-19, 2003.

Official Action Dated Jan. 31, 2013 From the US Patent and Trademark Office Re. U.S. Appl. No. 12/993,853.

Van Hagen et al. "Evaluation of a Radiolabelled Cyclic DTPA-RGD Analogue for Tumour Imaging and Radionuclide Therapy", International Journal of Cancer, 90(4): 186-198, Aug. 2000.

Translation of Office Action Dated Aug. 1, 2012 From the State Intellectual Property Office of the People's Republic of China Re. Application No. 200980128587.1.

Translation of Office Action Dated Jan. 5, 2012 From the State Intellectual Property Office of the People's Republic of China Re. Application No. 200980128588.6.

International Preliminary Report on Patentability Dated Dec. 2, 2010 From the International Bureau of WIPO Re. Application No. PCT/IL2009/000507.

International Preliminary Report on Patentability Dated Dec. 2, 2010 From the International Bureau of WIPO Re. Application No. PCT/IL2009/000510.

International Preliminary Report on Patentability Dated Dec. 2, 2010 From the International Bureau of WIPO Re. Application No. PCT/IL2009/000511.

Eldar-Boock et al. "Integrin-Assisted Drug Delivery of Nano-Scaled Polymer Therapeutics Bearing Paclitaxel", Biomaterials, 32(15): 3862-3874, May 2011.

Pan et al. "Backbone Degradable Multiblock N-(2-Hydroxypropyl)Methacrylamide Copolymer Conjugates Via Reversible Addition Fragmentation Chain Transfer Polymerization and Thiol-Ene Coupling Reaction", Biomacromolecules, 12(1): 247-252, Jan. 10, 2011.

Segal et al. "Enhanced Anti-Tumor Activity and Safety Profile of Targeted Nano-Scaled HPMA Copolymer-Alendronate-TNP-470 Conjugate in the Treatment of Bone Malignances", Biomaterials, 32(19): 4450-4463, Jul. 2011.

Segal et al. "Targeting Angiogenesis-Dependent Calcified Neoplasms Using Combines Polymer Therapeutics", PLoS ONE, 4(4): e5233-1-e5233-16, Apr. 2009.

International Search Report and the Written Opinion Dated Jun. 16, 2013 From the International Searching Authority Re. Application No. PCT/IL2013/050195.

* cited by examiner

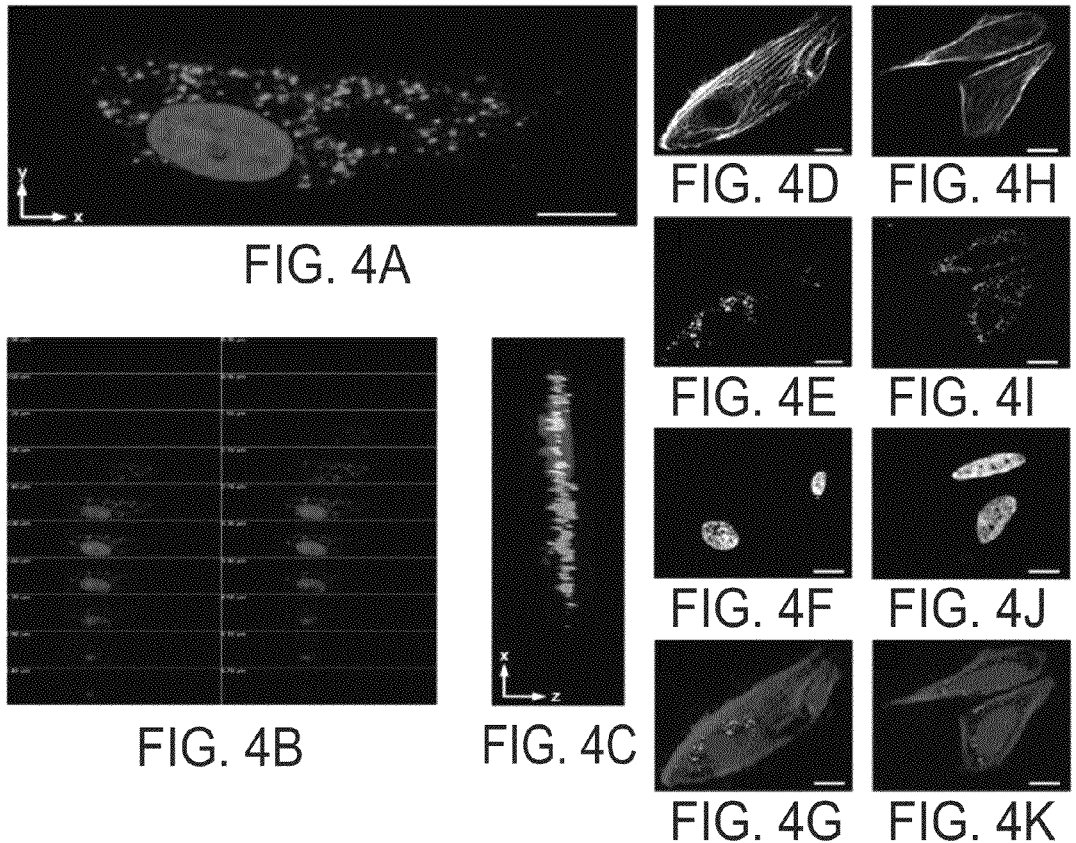
FIG. 4A
FIG. 4B
FIG. 4C
FIG. 4D
FIG. 4E
FIG. 4F
FIG. 4G
FIG. 4H
FIG. 4I
FIG. 4J
FIG. 4K
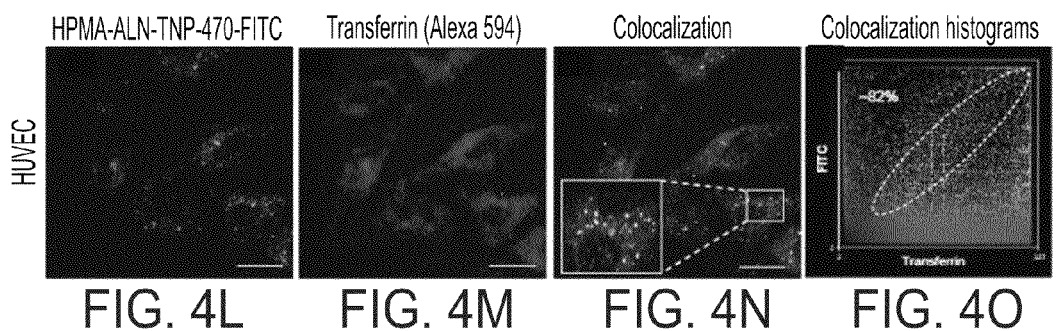
FIG. 4L  FIG. 4M  FIG. 4N  FIG. 4O
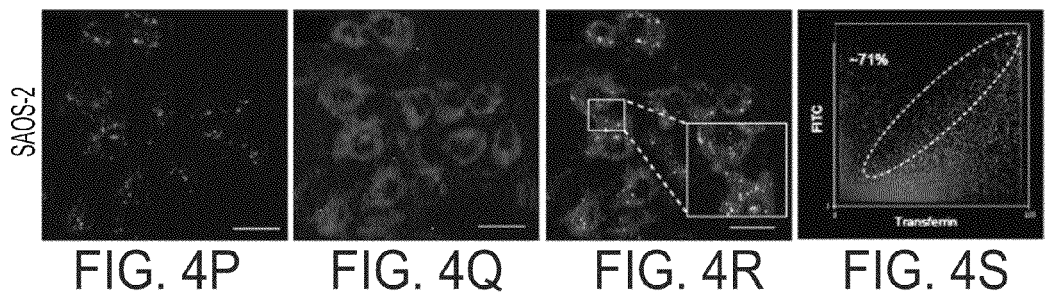
FIG. 4P  FIG. 4Q  FIG. 4R  FIG. 4S 1.
MA-Gly-Gly-OH $\xrightarrow{\text{HO-Tcp/DCC}}$ MA-Gly-Gly-OTcp  (MA-OTcp)
                                                            1

2.
MA-Gly-GlyProNle-NH(CH$_2$)$_2$NH—●    SPS synthesis using 2-chlortritylchoride beads
    ↓ 5% TFA/CH$_2$Cl$_2$ cleavage from the resin
MA-Gly-GlyProNle-NH(CH$_2$)$_2$NH$_2$
    ↓ Fmoc-Cl /THF in solution
MA-Gly-GlyProNle-NH(CH$_2$)$_2$NH—Fmoc  (MA-Fmoc)

3.
Fmoc-C$_6$-GlyProNle-C$_6$-Lys(FITC)-(D-Asp)$_8$—●     ["C6" = 1-aminohexanoic acid]
    ↓ 1. Fmoc deprotection piperidine/DMF
       2. 5% TFA/CH$_2$Cl$_2$ cleavage from the resin
NH$_2$-C$_6$-GlyProNle-C$_6$-Lys(FITC)-(D-Asp)$_8$—OH  (FD$_8$)
                                                    3

4.
HPMA + MA-Tcp + MA-Fmoc $\xrightarrow[\text{"Photo" polymerization/DMPAP initiator/DMSO/light}]{\text{"Thermo" polymerization/AIBN/DMSO/50°C}}$ ～～～|～～～|～～～   (P-Tcp-Fmoc)
                                                                                           Tcp    Fmoc
                                                                                                                    4

5.
～～～|～～～|～～～ $\xrightarrow{\text{FD}_8\text{/DMSO}}$ ～～～|～～～|～～～   (P-FD$_8$-Fmoc)
Tcp    Fmoc                               FD$_8$    Fmoc
                                                                        5

6.
～～～|～～～ $\xrightarrow[\text{TNP-470 binding}]{\text{piperidine/DMF/1 h}}$ [Polymer structure with HPMA, FITC, TNP-470, Asp$_8$ groups]
FD$_8$   Fmoc
                                                                                                            6

FIG. 8

CONJUGATE OF A POLYMER, AN ANTI-ANGIOGENESIS AGENT AND A TARGETING MOIETY, AND USES THEREOF IN THE TREATMENT OF BONE RELATED ANGIOGENESIS CONDITIONS

RELATED APPLICATIONS

This application is a National Phase of PCT Patent Application No. PCT/IL2009/000511 having International filing date of May 21, 2009, which claims the benefit of U.S. Provisional Patent Application Nos. 61/193,136 filed on Oct. 30, 2008 and 61/071,888 filed on May 22, 2008. The contents of the above Applications are all incorporated herein by reference.

STATEMENT OF GOVERNMENT INTEREST

This invention was made with Government support under GM069847 awarded by National Institutes of Health. The Government has certain rights to this invention.

FIELD AND BACKGROUND OF THE INVENTION

The present invention, in some embodiments thereof, relates to chemical conjugates and their use in therapy and diagnosis and, more particularly, but not exclusively, to chemical conjugates of a polymer, an anti-angiogenesis agent and a targeting moiety, which are useful, for example, in the treatment and monitoring of bone related diseases and disorders such as bone cancer and bone metastases.

Osteosarcoma is the most common type of primary bone cancer and classified as a malignant mesenchymal neoplasm in which the tumor directly produces defective osteoid (immature bone). It is a highly vascular and extremely destructive malignancy that most commonly arises in the metaphyseal ends of long bones. Over the past two decades, multimodality treatment consisting of aggressive chemotherapy combined with radical surgical resection, has been the mainstay of osteosarcoma management, with achievable 5 year survival rates of 50% to 70% in patients who do not have metastatic disease at presentation. Several strategies were proposed, such as immune-based therapy, tumor-suppressor or suicide gene therapy, or anticancer drugs that are not commonly used in osteosarcoma [Quan et al. *Cancer Metastasis Rev* 2006; 10: 707-713]. However, still one-third of patients die from this devastating cancer, and for those with unresectable disease there are no curative systemic therapies.

Prostate cancer is the most common cancer of males in industrialized countries and the second leading cause of male cancer mortality. Mortality in these patients is not due to primary tumor growth, but rather due to complications caused by metastases to vital organs. Prostate cancer predominantly metastasizes to bone, but other organ sites are affected including the lung, liver, and adrenal gland.

Breast cancer also often metastasizes to bones.

Bone metastases incidence in patients with advanced metastatic disease is approximately 70%. Bone metastases are associated with considerable skeletal morbidity, including severe bone pain, pathologic fracture, spinal cord or nerve root compressions, and hypercalcemia of malignancy. Chemotherapy agents, hormonal deprivation and bisphosphonates are the common treatments for advanced metastatic disease. However, with time, the disease progresses to a phase when the standard therapy fails to control the malignancy and further progresses to a highly chemotherapy-resistant state.

Tumor progression and metastases are highly dependent on oxygen and nutrients supplied by new blood vessels, which formation is stimulated by the tumor itself and its environment. Anti-angiogenic therapy combined with conventional treatment holds great potential for osteosarcoma management and metastatic risk reduction. Angiogenesis inhibitors, such as TNP-470 [Folkman, *J. Apmis* 2004; 112: 496-507], its non-toxic N-(2-hydroxypropyl)methacrylamide (HPMA) copolymer-conjugated form, caplostatin [Satchi-Fainaro et al. *Cancer Cell* 2005; 7: 251-261], and Avastin [Hurwitz et al. *N Engl J Med* 2004; 350: 2335-2342] are emerging as a new modality of anticancer drugs.

There are currently eight approved anti-cancer therapies with recognized antiangiogenic properties. These agents, which interrupt critical cell signaling pathways involved in tumor angiogenesis and growth, can be divided into two primary categories: (1) monoclonal antibodies directed against specific proangiogenic factors and/or their receptors; (Avastin, Erbitux, Vectibix, Herceptin) and (2) small molecule tyrosine kinase inhibitors (TKIs) of multiple proangiogenic growth factor receptors (Tarveca, Nexavar, Sutent). Inhibitors of mTOR (mammalian target of rapamycin) represent a third, smaller category of antiangiogenic therapies with one currently approved agent (Torisel). In addition, at least two other approved anti-angiogenic agents may indirectly inhibit angiogenesis through mechanisms that are not completely understood (Velcade, Celgene)

The first FDA-approved angiogenesis inhibitor, Bevacizumab (Avastin, Genentech), a monoclonal antibody to vascular endothelial growth factor (VEGF), has recently been approved for metastatic colon cancer treatment in conjunction with standard conventional chemotherapy.

The largest class of drugs that block angiogenesis are the multi-targeted tyrosine kinase inhibitors (TKIs) that target the VEGF receptor (VEGFR). These drugs such as sunitinib (Sutent, Pfizer), Sorafenib (Nexavar, Bayer/Onyx Pharmaceuticals) and Erlotinib (Tarveca, Gennentech/OSI/Roche) have the advantages of hitting multiple targets, convenient oral administration, and cost effectiveness. While these drugs exhibit promising efficacy, their use is limited by their lack of target specificity, which leads to unexpected toxicity [Cabebe et al. *Curr Treat Options Oncol* 2007; 8:15-27].

Novel targeted angiogenesis inhibitors, for use with or without other anti-neoplastic agents have therefore been sought for. A major impediment towards this effort has been the inability to determine therapeutic efficacy, the lack of reliable surrogate markers of tumor angiogenesis, and the complexity of interactions between multiple host cells and malignant cells involved in tumor angiogenesis, which may limit the use of a single anti-angiogenic agent. Another significant obstacle is that the vast majority of clinically used anti-cancer and anti-angiogenic drugs are small molecules that exhibit a short half-life in the bloodstream and a high overall clearance rate. These low-molecular weight drugs diffuse rapidly into healthy tissues and are distributed evenly within the body. As a consequence, relatively small amounts of the drug reach the target site, and therapy is associated with low efficacy and severe side effects.

TNP-470 is a low molecular weight synthetic analogue of fumagillin, which is capable of selectively inhibiting endothelial growth in vitro. In clinical trials, this drug was found to slow tumor growth in many patients with metastatic cancer and exhibited a promising efficacy when used in combination with conventional chemotherapy. However, at the doses required for tumor regression, many patients experienced neurotoxicity. Due to its dose-limiting neurotoxicity, no further clinical studies were conducted for using TNP-470 per se. It has been concluded that clinical uses of TNP-470 should be performed with this agent being targeted to tumor tissue, in order to increase its site specificity and reduce side effects.

Water-soluble polymers such as N-(2-Hydroxypropyl) methacrylamide copolymers (HPMA) are biocompatible, non-immunogenic and non-toxic carriers that enable specific delivery into tumor tissue [Satchi-Fainaro et al. *Nat Med* 2004; 10: 255-261]. These macromolecules do not diffuse through normal blood vessels but rather accumulate selectively in the tumor site because of the enhanced permeability and retention (EPR) effect. This phenomenon of passive diffusion through the hyperpermeable neovasculature and localization in the tumor interstitium is observed in many solid tumors for macromolecular agents and lipids. Conjugation of anti-cancer drugs such as TNP-470 with copolymers, such as HPMA, should enable selective targeting of these drugs to tumor tissue and thus reduce side effects. Furthermore, such copolymer-drug conjugates should restrict the passage through the blood brain barrier and would prolong the circulating half-life of the drugs, hence inhibiting the growth of tumor endothelial and epithelia cells by exposing the cells to the conjugated drugs in the circulation for a longer time compared to the free drugs.

An example of the favorable characteristics obtained by conjugation of an anti-angiogenesis agent such as TNP-470 to HPMA has been described by Satchi-Fainaro et al. in WO 03/086382. This patent application teaches conjugates of water-soluble polymers and TNP-470, and their use as anti-tumor agents, in particular their use as carriers of TNP-470 into tumor vessels, and their effect on the neurotoxicity of TNP-470. According to the teachings of WO 03/086382, an exemplary such conjugate, HPMA-(TNP-470) conjugate (caplostatin), exhibited superior antitumor activity together with a reduced level of toxicity, as compared with TNP-470 alone. WO 03/086382 further suggests incorporation of a targeting ligand, such as RGD or antibodies.

The use of HPMA-TNP-470 conjugate for the treatment of angiogenesis related conditions has also been described in WO 03/086178.

Another example of the increased activity yet reduced toxicity obtained by conjugation of anti-tumor drugs to water-soluble polymers is presented in U.S. Pat. No. 6,884,817.

An HPMA copolymer conjugate of paclitaxel has been described by Meerum Terwogt et al. [*Anticancer drugs* 2001; 12:315-323]. This conjugate was aimed at improving drug solubility and providing controlled release of paclitaxel. In this conjugate, the paclitaxel is linked to the HPMA copolymer through an ester bond, and is hence released from the polymer by non-tissue specific hydrolytic or enzymatic (esterases) degradation of the ester bond, thereby inducing the commonly observed toxicities of paclitaxel.

Bisphosphonates (BPs) such as alendronate are compounds with a chemical structure similar to that of inorganic pyrophosphate (PPi), an endogenous regulator of bone mineralization. Several bisphosphonates are established as effective treatments in clinical disorders such as osteoporosis, Paget's disease of bone, myeloma, and bone metastases. Bisphosphonates, such as zoledronic acid, have been shown to inhibit angiogenesis [Wood et al. *J Pharmacol Exp Ther* 2002; 302: 1055-1061]. The pharmacokinetic profile of bisphosphonates, which exhibit a strong affinity to bone mineral under physiological conditions, their low toxicity and anti-angiogenic activity are advantageous for targeting to tumors confined to bony tissues.

Alendronate is considered potent for the treatment of bone related diseases and cancer-associated hypercalcemia. It was shown to have antitumor effect in several in vivo cancer models through several different mechanisms [Tuomela et al. 2008, *BMC Cancer* 8:81; Molinuevo et al. 2007, *Eur J Pharmacol* 562:28-33; Hashimoto et al. 2005, *Cancer Res* 65: 540-545]. In addition, alendronate was found to have anti-angiogenic activity through (i) suppression of VEGF-induced Rho activation in an ovarian cancer model [Hashimoto et al. 2007, *Biochem Biphys Res Commun* 354: 478-484], (ii) inhibition of farnesyl pyrophosphate synthase, in the mevalonate pathway [Russell R G 2007, *Pediatrics* 119 Suppl 2: S150-162]; and (iii) regulation of cellular level of MMP-2 expression in osteosarcoma cell lines [Cheng et al. 2004, *Pediatr Blood Cancer* 42; 410-415].

Other bone targeting agents are oligopeptides of Aspartate. Wang et al. describe fluorescein-labeled bone-targeted model conjugates for detection purposes bearing 1% loading of D-Asp$_8$ (SEQ ID NO:1) on HPMA copolymer [Wang et al. 2003 *Bioconjug Chem* 14:853-859]. The bone-targeting potential of this conjugate was tested in vitro and in vivo and was found to selectively accumulate in bone tissue [Wang et al. 2006, *Mol Pharm* 3:717-725].

WO 2004/062588 teaches water soluble polymeric conjugates for bone targeted drug delivery with improved pharmacokinetics parameters and better water solubility of the loaded drugs. The polymeric drug delivery systems taught by this application are based on hydroxypropyl methacrylamide (HPMA) conjugates of bone-targeting drugs such as alendronate and D-Asp$_8$ together with a bone-related therapeutic agent. The loading of alendronate and D-Asp$_8$ (SEQ ID NO:1) onto the HPMA copolymer was 0.494 mmol/gram and 0.762 mmol/gram respectively.

PK2 (FCE28069) is a HPMA copolymer-doxorubicin-galactosamine conjugate, which was designed as a treatment for hepatocellular carcinoma or secondary liver disease [Seymour et al. *Journal of Clinical Oncology* 2002; 20:1668-1676]. Doxorubicin is an anthracycline antibiotic with limited solubility in physiological fluids, and is a well established anti-neoplastic drug. Galactosamine binds to the hepatic asialoglycoprotein receptor (ASGPR) thus serving as a specific hepatic targeting moiety. These components are linked to the HPMA polymer via an enzymatically biodegradable linker which permits the release of free doxorubicin within the liver, thus increasing the drug concentration in its site of action. The enzymatic degradable linker is a tetrapeptide spacer (Gly-Phe-Leu-Gly) (SEQ ID NO:2), designed for cleavage by lysosomal cathepsins.

O'hare et al. [*Journal of Drug Targeting* 1993; 1:217-229] have synthesized HPMA copolymers containing doxorubicin and melanocyte stimulating hormone (MSH) as a melanoma specific targeting moiety. Both the doxorubicin and the melanocyte stimulating hormone were linked to the HPMA polymer via an enzymatically biodegradable linker.

Hruby et al. [*Journal of Applied Polymer Science* 2006; 101: 3192-3201] have prepared and synthesized novel polymeric drug-delivery systems designed for bone targeting of anti-neoplastics based on biocompatible HPMA copolymers containing hydroxybisphosphonate targeting moieties and the model drugs radiotherapeutics $^{125}$I, imaging agent $^{111}$In, or the anticancer drug Doxorubicin. The percentage of hydroxybisphosphonate loaded onto the HPMA copolymers was in the range of 1.3-4 mol %.

SUMMARY OF THE INVENTION

Currently known agents used for treating bone related cancer and other angiogenesis-related conditions, at doses where anti-tumor activity is achieved, are characterized by high toxicity, which limits their use. In a search for modes of modifying currently known anti-angiogenesis agents so as to enable higher therapeutic efficacy thereof together with a reduced level of side effects, the present inventors have designed and successfully prepared and practiced a novel polymeric conjugate of N-(2-hydroxypropyl)-methacrylamide (HPMA) copolymer, TNP-470 and the bone targeting agent alendronate (ALN), wherein the TNP-470 and alendronate molecules are conjugated to backbone units of the HPMA polymeric backbone via biodegradable linkers and the percent of alendronate loaded onto the HPMA polymeric backbone is higher than in currently known alendronate-polymer conjugates (e.g., is greater than 3 mol % of the polymeric conjugate).

The present inventors have further devised and successfully practiced a novel process for preparing the conjugates described herein, while obtaining a high load of alendronate in the polymer as well as a homogenous size distribution, i.e. low polydispersity, of the polymer. This process can be beneficially performed in a controlled manner at 30° C.

The present inventors have designed and successfully prepared and practiced a novel conjugate of a polymer (e.g., a N-(2-hydroxypropyl)methacrylamide (HPMA) copolymer), an anti-angiogenesis agent (e.g., TNP-470) and a bone targeting agent being D-Asp8 (SEQ ID NO:1).

According to an aspect of some embodiments of the present invention there is provided a conjugate comprising an N-(2-hydroxypropyl)methacrylamide)-derived polymeric backbone having attached thereto TNP-470 and alendronate, wherein a load of the alendronate in the polymer is greater than 3 mol %

According to some embodiments of the invention, the load of the alendronate in the polymer is greater than 5 mol %.

According to some embodiments of the invention, the load of the alendronate in the polymer is about 7 mol %.

According to some embodiments of the invention, at least one of the TNP-470 and the alendronate is attached to the polymer via a linker.

According to some embodiments of the invention, each of the TNP-470 and the alendronate is attached to the polymer via a linker.

According to some embodiments of the invention, the linker is a biodegradable linker.

According to some embodiments of the invention, the biodegradable linker is selected from the group consisting of a pH-sensitive linker and an enzymatically cleavable linker.

According to some embodiments of the invention, the biodegradable linker is an enzymatically cleavable linker.

According to some embodiments of the invention, the enzymatically cleavable linker is cleaved by an enzyme which is expressed in tumor tissues.

According to some embodiments of the invention, the enzymatically cleavable linker is cleaved by an enzyme which is overexpressed in tumor tissues.

According to some embodiments of the invention, the enzyme is selected from a group consisting of Cathepsin B, Cathepsin K, Cathepsin D, Cathepsin H, Cathepsin L, legumain, MMP-2 and MMP-9.

According to some embodiments of the invention, the enzyme is Cathepsin K.

According to some embodiments of the invention, the linker comprises an oligopeptide group containing from 2 to 10 amino acid residues.

According to some embodiments of the invention, the oligopeptide is -[Gly-Gly-Pro-Nle]- (SEQ ID NO:3).

According to some embodiments of the invention, the TNP-470 is linked to the polymer or to the linker via a spacer.

According to some embodiments of the invention, the spacer has the formula G-(CH$_2$)n-K, wherein n is an integer from 1 to 4; and G and K are each independently selected from the group consisting of NH, O and S.

According to some embodiments of the invention, G and K are each NH and n is 2.

According to some embodiments of the invention, the alendronate is attached to the polymer via a linker that comprises (SEQ ID NO:3).

According to some embodiments of the invention, the conjugate has the general formula II, as described herein.

According to some embodiments of the invention, the conjugate has the structure:

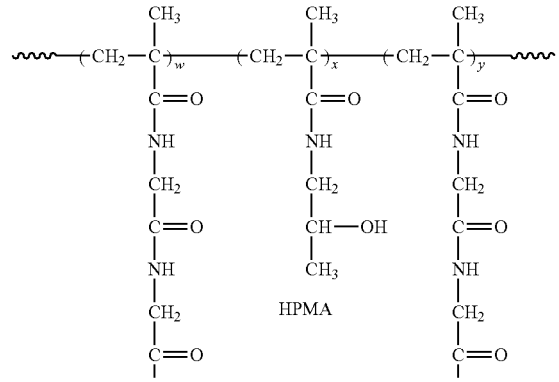

-continued

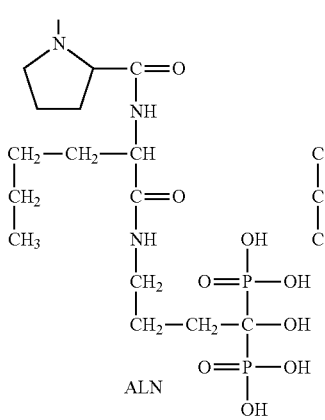
ALN

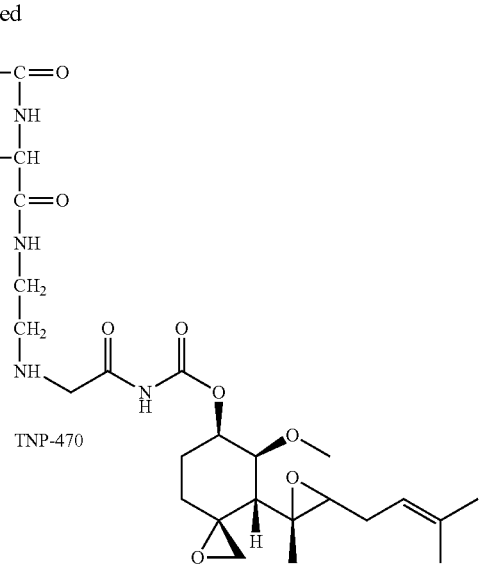
TNP-470

According to some embodiments of the invention, x is an integer that equals 70-99.9 and y and w are each independently an integer that equals 0.01-15.

According to some embodiments of the invention, the conjugate further comprising a labeling agent.

According to some embodiments of the invention, the labeling agent is selected from the group consisting of a fluorescent agent, a radioactive agent, a magnetic agent, a chromophore, a bioluminescent agent, a chemiluminescent agent, a phosphorescent agent and a heavy metal cluster.

According to some embodiments of the invention, the labeling agent is Fluorescein isothiocyanate.

Such conjugate is having, for example, the following structure:

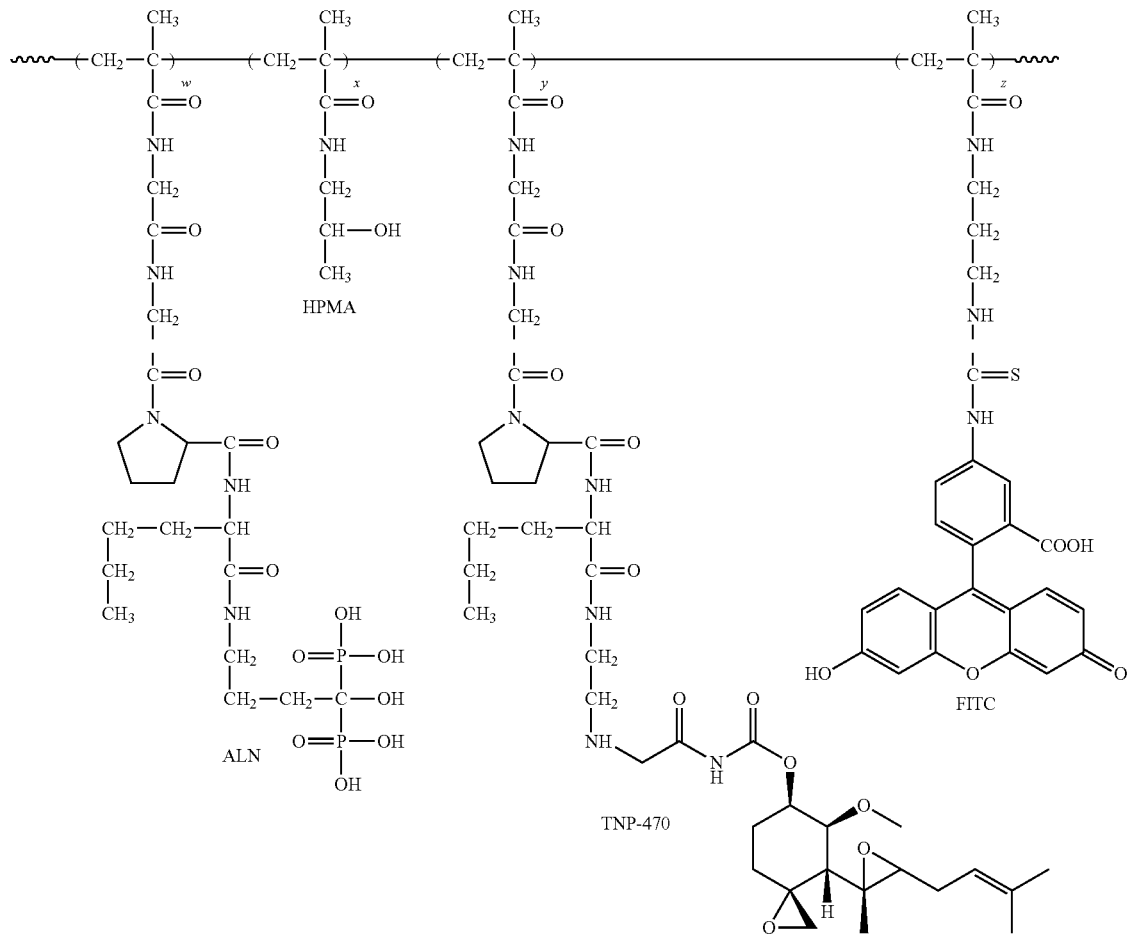

wherein:

x is an integer that equals 70-99.9; and y, z and w are each independently an integer that equals 0.01-15.

According to an aspect of some embodiments of the present invention there is provided a process of synthesizing the conjugates as described hereinabove, the process comprising:

(a) coupling alendronate to N-(2-hydroxypropyl)methacrylamide monomeric units, to thereby obtain alendronate-containing methacrylamide monomeric units;

(b) co-polymerizing N-(2-hydroxypropyl)methacrylamide monomeric units, and/or ((N-(2-hydroxypropyl)methacrylamide) oligomeric or polymeric units with the alendronate-containing methacrylamide monomeric units and with methacrylamide monomeric units terminating with a first reactive group, to thereby obtain a polymeric backbone which comprises a plurality of methacrylamide backbone units in which a portion of the backbone units has an alendronate attached thereto, and another portion of the backbone units has said reactive group, the first reactive group being capable of coupling TNP-470; and (c) coupling the TNP-470 and the polymeric backbone via the first reactive group, thereby obtaining the polymeric conjugate.

According to another aspect of some embodiments of the present invention there is provided a conjugate comprising a polymeric backbone having attached thereto an anti-angiogenesis agent and a bone targeting moiety, the bone targeting moiety being an oligopeptide of aspartic acid which comprises from 2 to 100 amino acid residues.

According to some embodiments of the invention, the oligopeptide comprises from 2 to 20 amino acid residues.

According to some embodiments of the invention, the oligopeptide comprises 8 amino acid residues.

According to some embodiments of the invention, the aspartic acid is selected from the group consisting of D-aspartic acid and L-aspartic acid.

According to some embodiments of the invention, the aspartic acid is D-aspartic acid.

According to some embodiments of the invention, at least one of the anti-angiogenesis agent and the bone targeting moiety is attached to the polymeric backbone via a linker.

According to some embodiments of the invention, the linker is a biodegradable linker.

According to some embodiments of the invention, each of the anti-angiogenesis agent and the bone targeting moiety is attached to the polymeric backbone via a linker:

According to some embodiments of the invention, the polymeric backbone is derived from a polymer that has an average molecular weight that ranges from 100 Da to 800 kDa.

According to some embodiments of the invention, the polymeric backbone is derived from a polymer selected from the group consisting of dextran, a water soluble polyamino acid, a polyethylenglycol (PEG), a polyglutamic acid (PGA), a polylactic acid (PLA), a polylactic-co-glycolic acid (PLGA), a poly(D,L-lactide-co-glycolide) (PLA/PLGA), a poly(hydroxyalkylmethacrylamide), a polyglycerol, a polyamidoamine (PAMAM), and a polyethylenimine (PEI).

According to some embodiments of the invention, the polymer is N-(2-hydroxypropyl)methacrylamide).

According to some embodiments of the invention, the anti-angiogenesis agent is TNP-470.

According to some embodiments of the invention, the biodegradable linker is selected from the group consisting of a pH-sensitive linker and an enzymatically-cleavable linker, as described herein.

According to an aspect of some embodiments of the present invention there is provided a pharmaceutical composition comprising, as an active ingredient, any of the conjugates described herein and a pharmaceutically acceptable carrier.

According to some embodiments of the invention, the composition is packaged in a packaging material and identified in print, in or on the packaging material, for use in the treatment of a bone related disease or disorder.

According to some embodiments of the invention, the conjugate comprises a labeling agent, the composition being packaged in a packaging material and identified in print, in or on the packaging material, for use in monitoring a bone related disease or disorder.

According to some embodiments of the invention, the bone related disease or disorder is associated with angiogenesis.

According to an aspect of some embodiments of the present invention there is provided a method of treating a bone related disease or disorder in a subject in need thereof, the method comprising administering to the subject a therapeutically effective amount of any of the conjugates described herein.

According to an aspect of some embodiments of the present invention there is provided a use of the conjugate as described hereinabove as a medicament.

According to an aspect of some embodiments of the present invention there is provided a use of the conjugate as described hereinabove in the manufacture of a medicament for treating a bone-related disease or disorder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

The patent or application file contains at least one drawing executed in color. Copies of this patent or patent application publication with color drawing(s) will be provided by the Office upon request and payment of the necessary fee.

In the drawings:

Figure 1:
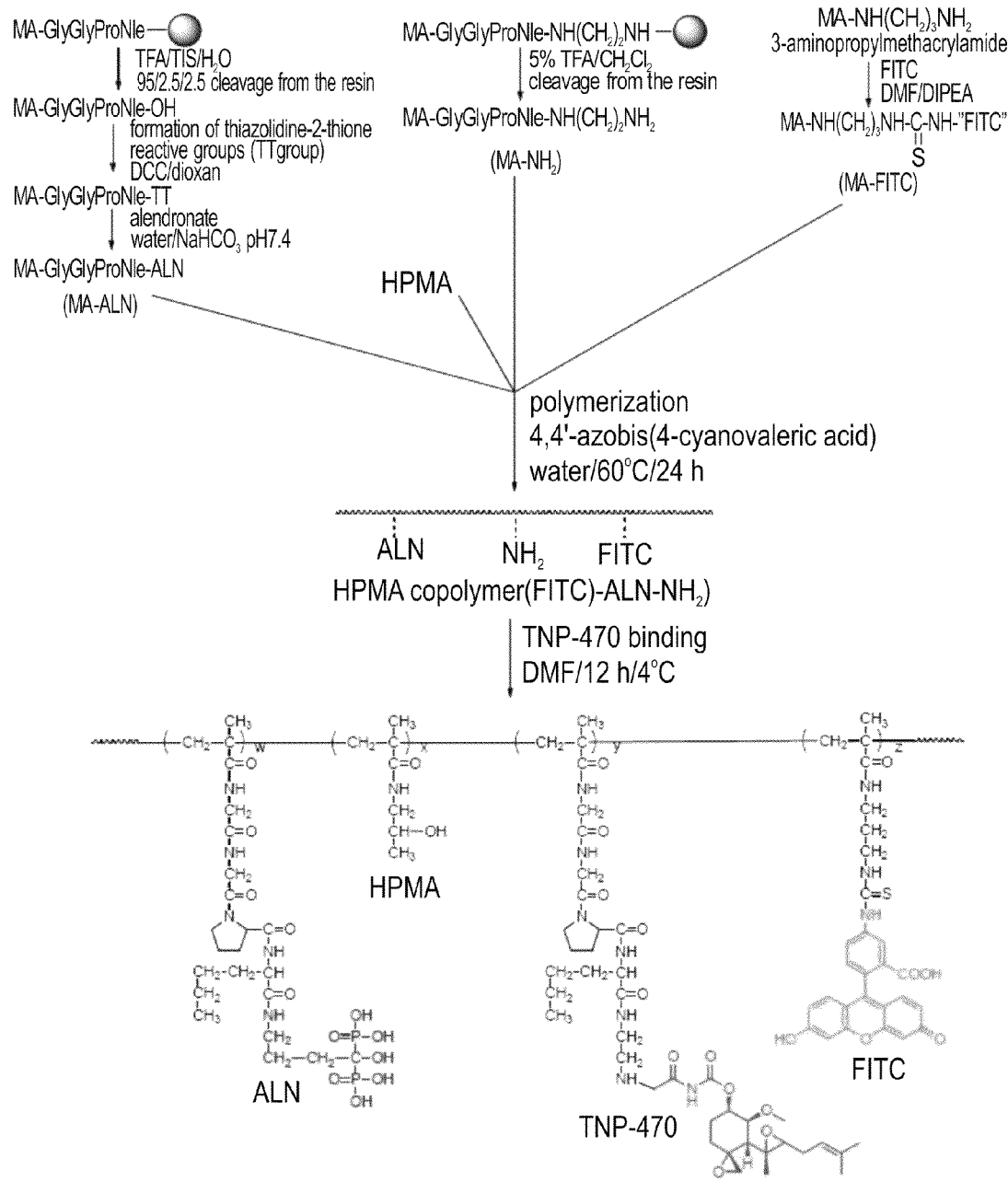

FIG. 1 presents a scheme illustrating the synthesis of an HPMA copolymer-ALN-TNP-470 conjugate according to some embodiments of the present invention.

Figure 2A:
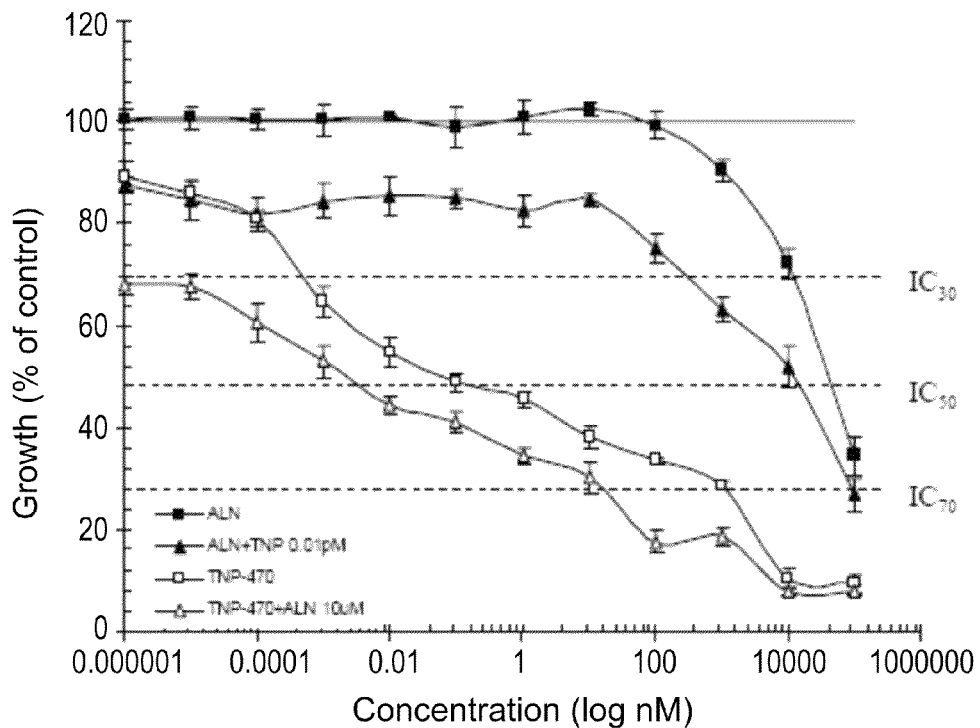
Figure 2B:
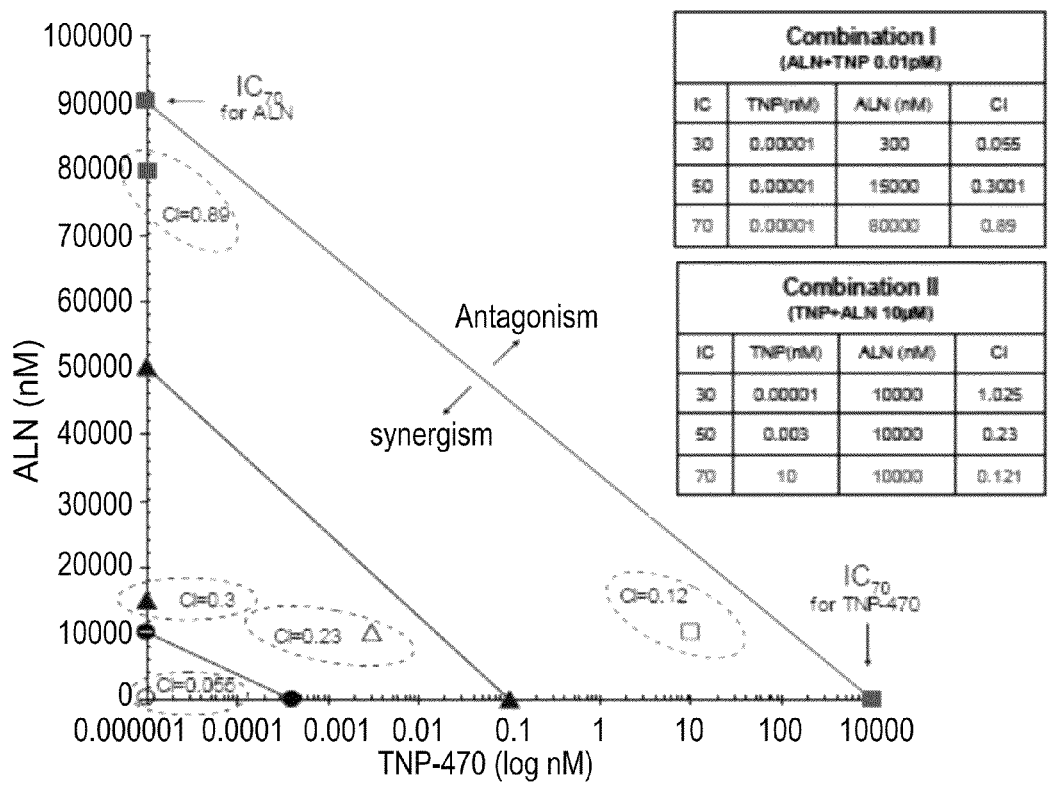

FIGS. 2A-B present data showing the synergistic inhibitory effect of the combined treatment of alendronate and TNP-470 on proliferation of endothelial cells in vitro. FIG. 2A presents comparative plots showing the effect of ALN (closed squares), TNP-470 (open squares), ALN+TNP-470 0.01 pM (closed triangles) and ALN+TNP-470 10 μM (open triangles), on the proliferation of human umbilical vain endothelial cells (HUVEC), and demonstrating the synergistic effect of a combined alendronate and TNP-470 treatment. FIG. 2B presents a classic isobologram of ALN-TNP-470 combination treatment at $IC_{70}$ (closed squares), $IC_{50}$ (closed triangles) and $IC_{30}$ (closed circles). The dashed circles represent synergism areas of the combined ALN+TNP-470 treatment. The tables represent the CI values of each IC of combination treatments I and II. Data represent mean±SD.

Figure 3A:
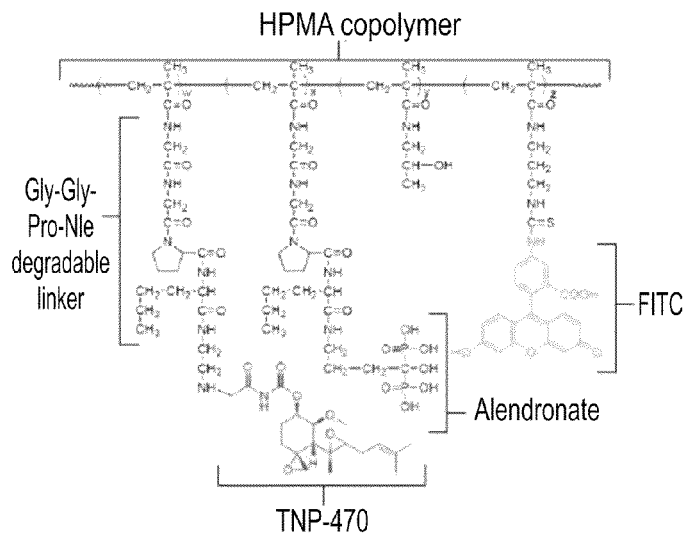
Figure 3B:
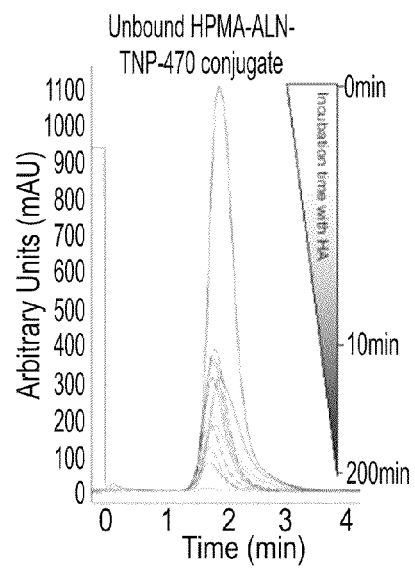
Figure 3C:
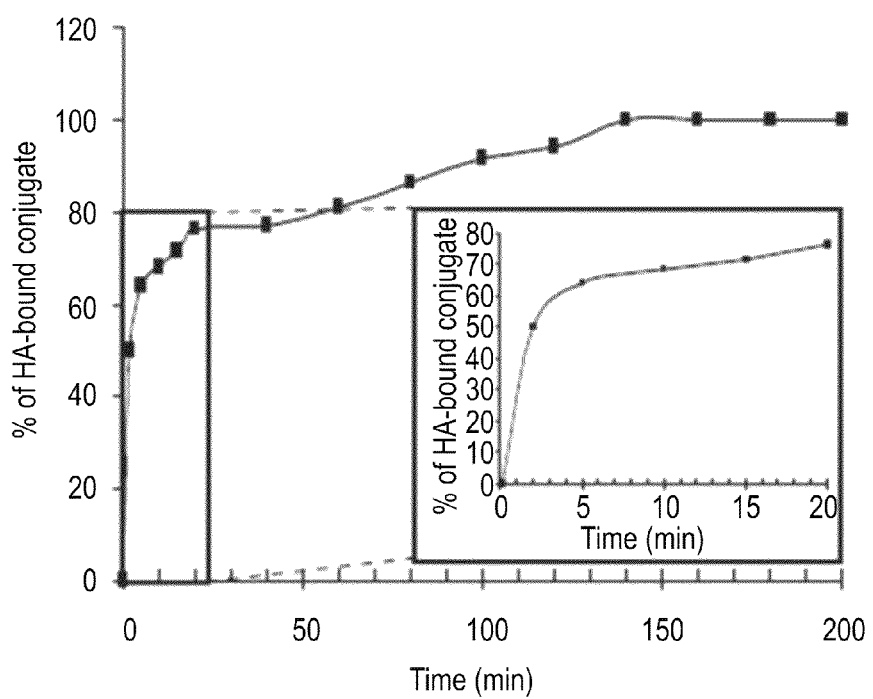
Figure 3D:
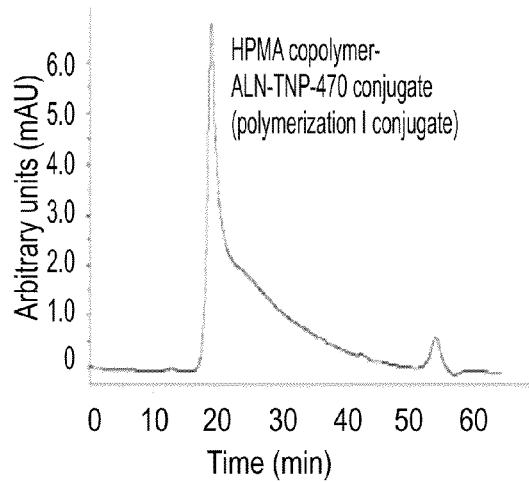
Figure 3E:
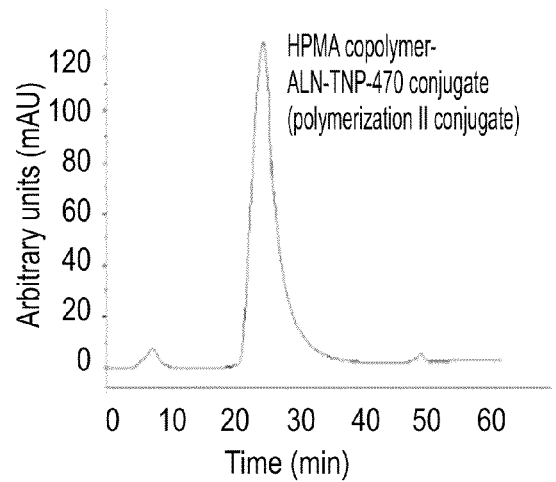
Figure 3F:
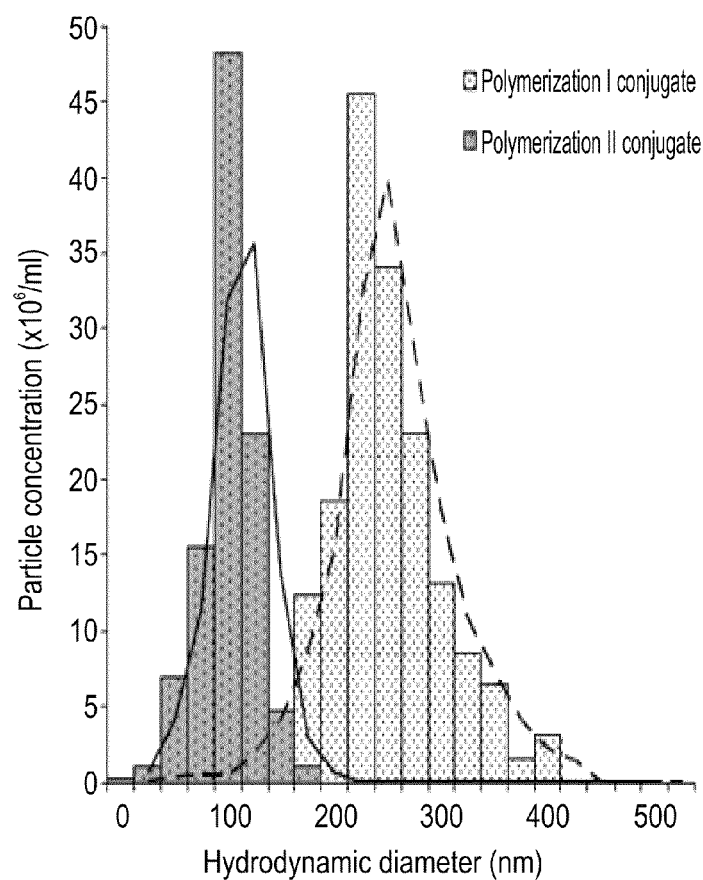
Figure 3G:
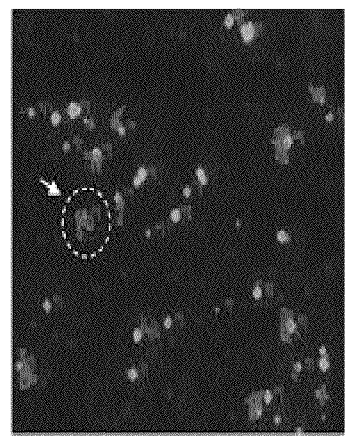

FIGS. 3A-G present the 2-D chemical structure of fluorosceinated-HPMA copolymer-ALN-TNP-470 conjugates according to some embodiments of the present invention (FIG. 3A); a diagram showing FPLC detection of unbound HPMA-ALN-TNP470 conjugate in the samples, in the presence and absence of Hydroxyapitate, at selected time points (FIG. 3B); and plots showing the percentages of HPMA-ALN-TNP-470 conjugate bound to hydroxyapatite as a function of the elution time (FIG. 3C); size exclusion chromatography (SEC) profile of conjugate polymerized by the classical polymerization method (Polymerization I conjugate; FIG. 3D) or conjugate polymerized by RAFT polymerization (Polymerization II conjugate; FIG. 3E); a graph showing the hydrodynamic diameter size distribution of the HPMA-ALN-TNP-470 polymerization I conjugate and polymerization II conjugate (FIG. 3F); and an image of the polymer I conjugate particles obtained (FIG. 3G).

FIGS. 4A-S present confocal images showing the intracellular trafficking of FITC-labeled HPMA copolymer-ALN-TNP-470 conjugate, according to some embodiments of the present invention, in human umbilical vain endothelial cells (HUVEC) and Saos-2 human osteosarcoma cells. Single XY plane imaging of the conjugate (green) with PI (red) nuclei staining showed cytoplasmatic accumulation of the conjugate. Cellular uptake analysis of the conjugate by HUVEC cells (FIG. 4A); 5.7 μm Z-stack of 28 slices (FIG. 4B); and XZ image slice, show similar conjugate and nuclei focal plane localization (FIG. 4C); Multi-channel overlay of HUVEC (FIG. 4G) and Saos-2 cells (FIG. 4K) stained with phalloidin (red) for actin filaments (FIGS. 4D and 4H) and DAPI (blue) for nuclei (FIGS. 4F and 4J) 12 hours post incubation with the ALN-TNP-470 conjugate (green) (FIGS. 4E, 4I), showing cellular localization of the conjugate mostly around the nuclei; the FITC-labeled conjugate (green) (FIGS. 4L and 4P) colocalized with clathrin-coated vesicles labeled with transferrin (red) (FIGS. 4M and 4Q) in HUVEC (FIGS. 4M and 4N) and Saos-2 (FIGS. 4Q and 4R) cells; histograms of overlay images showing a ratio of conjugate/transferrin of 82% in HUVEC (FIG. 4O) and 71% in Saos-2 (FIG. 4S) cells pointing at the cellular uptake of the conjugate via the lysosomotropic pathway. Bars represent 5 μm (FIGS. 4A-4K) and 20 μm (FIGS. 4L-4S).

Figure 5:
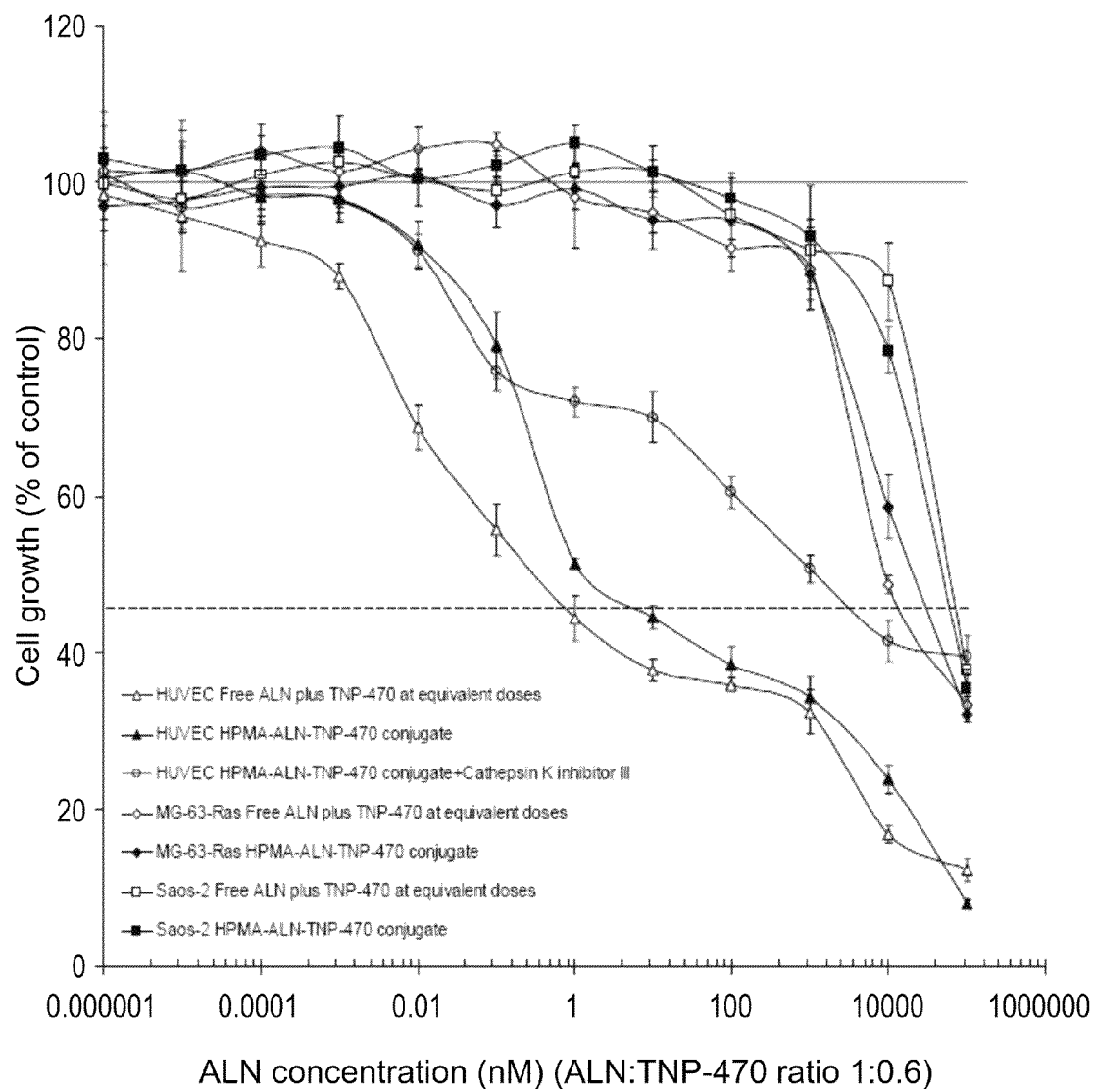

FIG. 5 present comparative plots demonstrating that ALN and TNP-470 retain their antiangiogenic effect when bound to the HPMA copolymer. The percentage of average cell growth is similar in the presence of polymer-conjugated ALN and TNP-470 in HUVEC cells (closed triangles), Saos-2 cells (closed squares) and MG-63-Ras (closed diamonds) compared with a combination of free ALN and free TNP-470 in HUVEC cells (open triangles), in Saos-2 cells (open squares) and MAG-63-Ras (open diamonds. The inhibition of endothelial proliferation by the conjugate was reduced significantly ($IC_{50}$=4200 nM) in the presence of cathepsin K inhibitor III (open circles). Solid and dashed lines represent the proliferation of cells in the presence (solid line) or absence (dashed line) of growth factors. Data represent mean±SD.

Figure 6A:
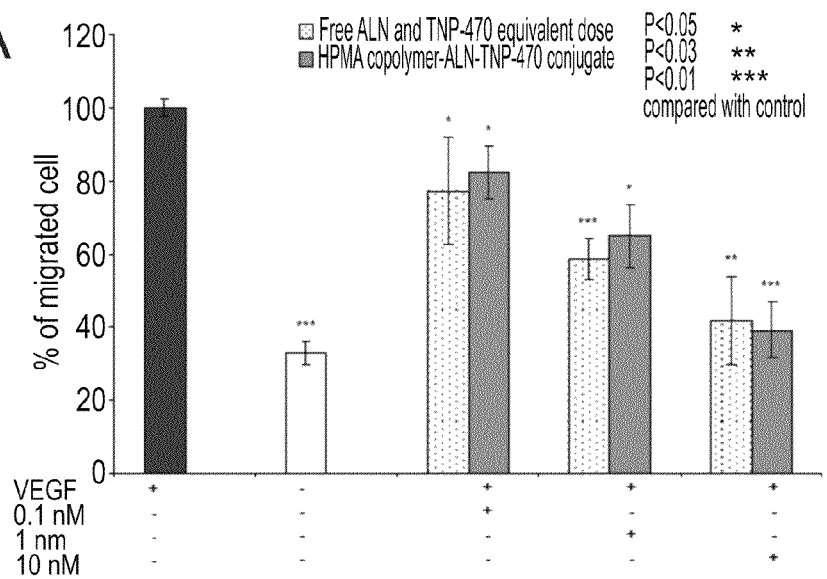
Figure 6B:
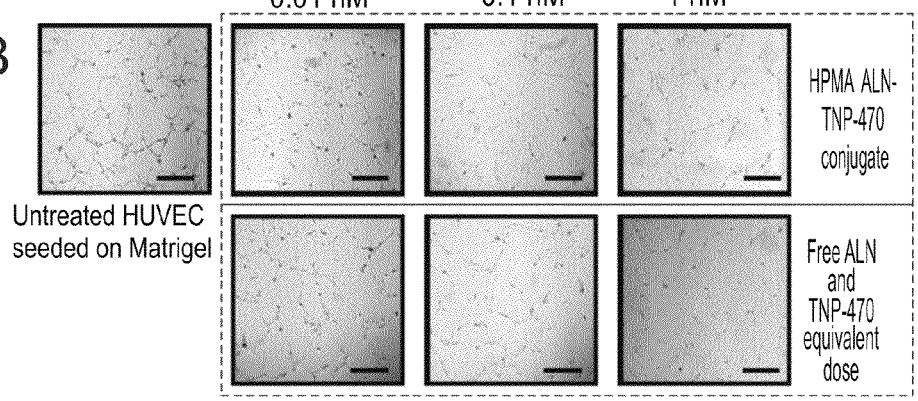
Figure 6C:
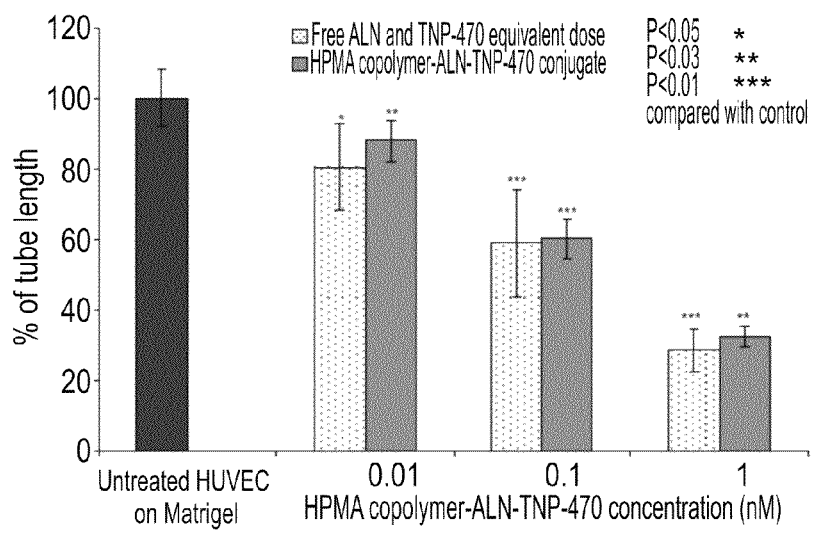

FIGS. 6A-C present the effect of HPMA copolymer-ALN-TNP-470 conjugate and free ALN+free TNP-470 on the ability of HUVEC to migrate towards vascular endothelial growth factor (VEGF) chemoattractant and the ability to form capillary-like tube structures. FIG. 6A presents a bar graph showing that free (dotted bars) and polymer-conjugated (gray bars) ALN and TNP-470 inhibited VEGF induced HUVEC migration; FIG. 6B presents images of HUVEC exposed to the combination of free ALN+free TNP-470, and with HPMA copolymer ALN-TNP470 after 8 hours of incubation; and FIG. 6C presents a bar graph showing the percentages of inhibition of HUVEC capillary-like tube structures by different concentrations of free (dotted bars) and polymer-conjugated (gray bars) ALN and TNP-470, compared with non-treated cells (black bar). Data represent mean±SD.

Figures 7A, 7B:
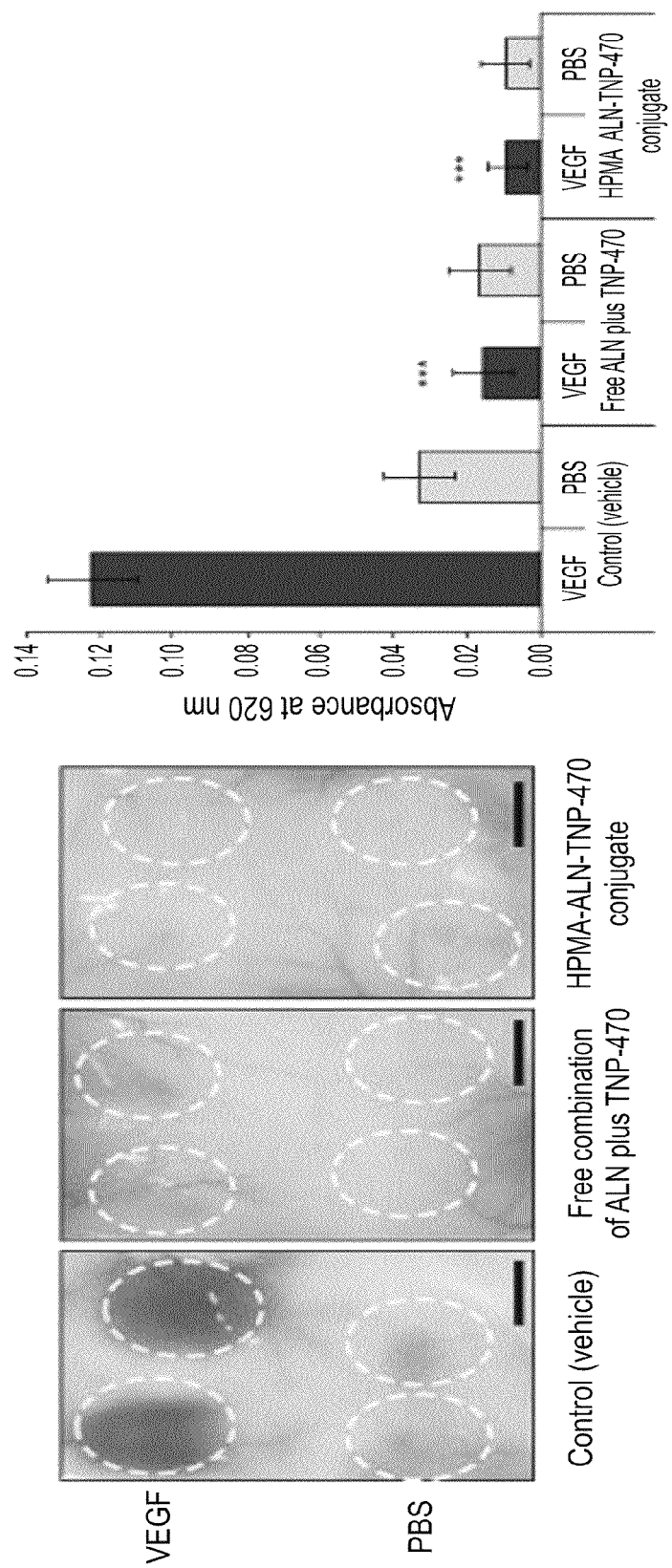
Figure 7D:
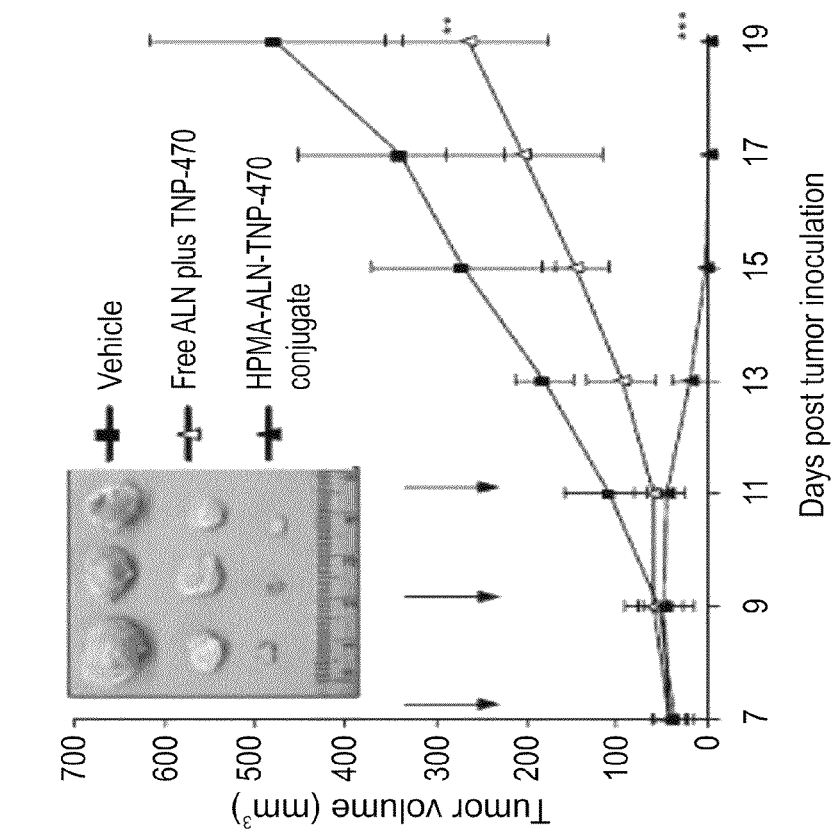
Figure 7C:
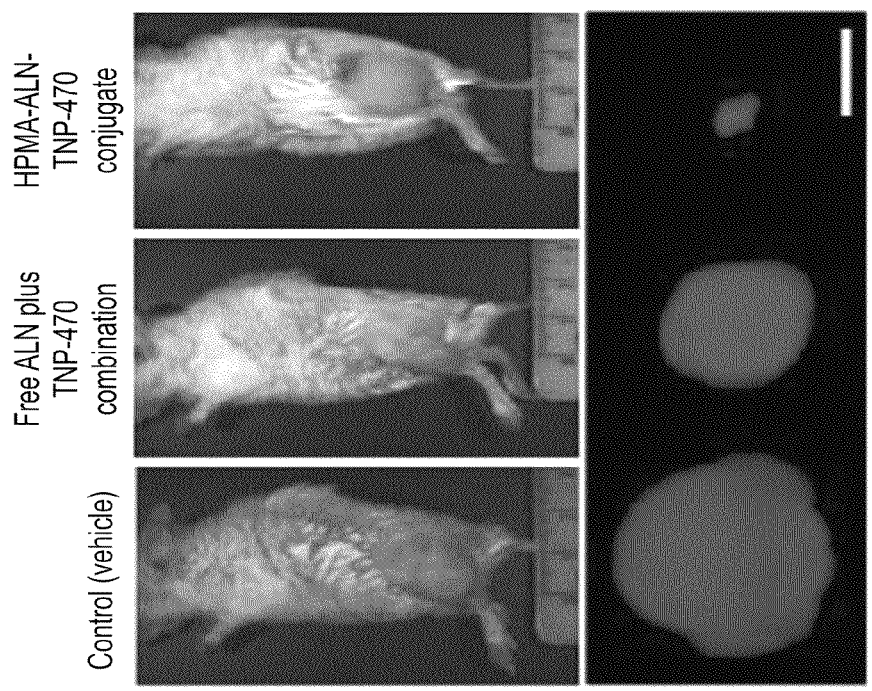
Figure 7F:
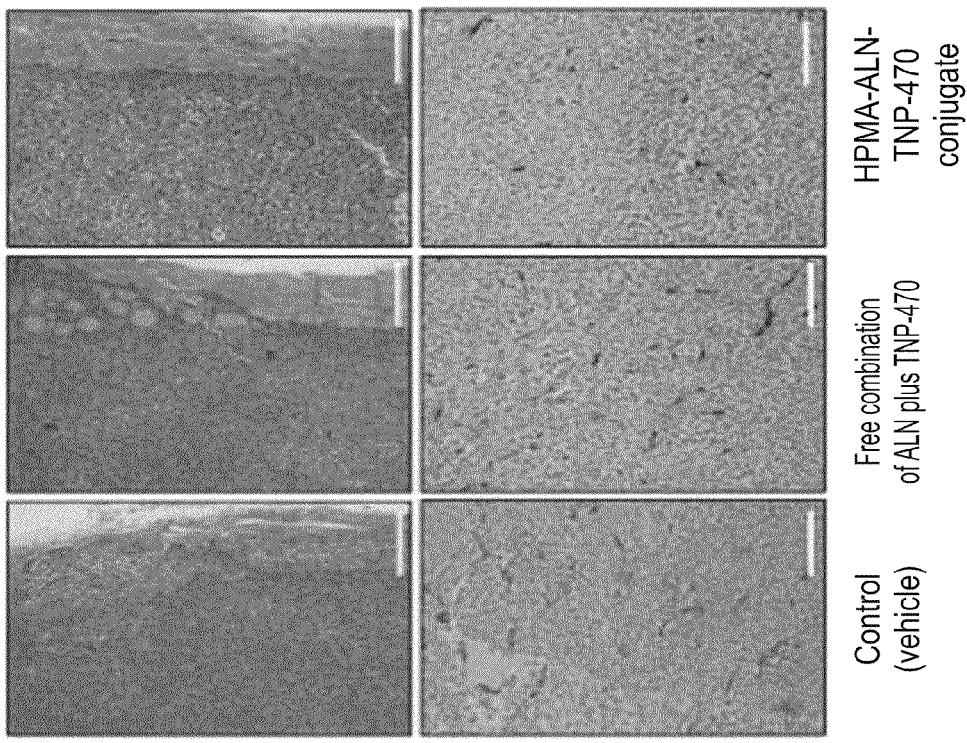
Figure 7E:
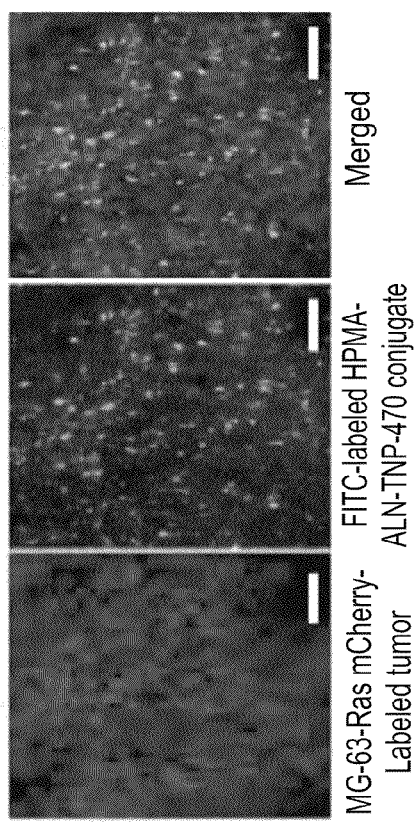
Figure 7G:
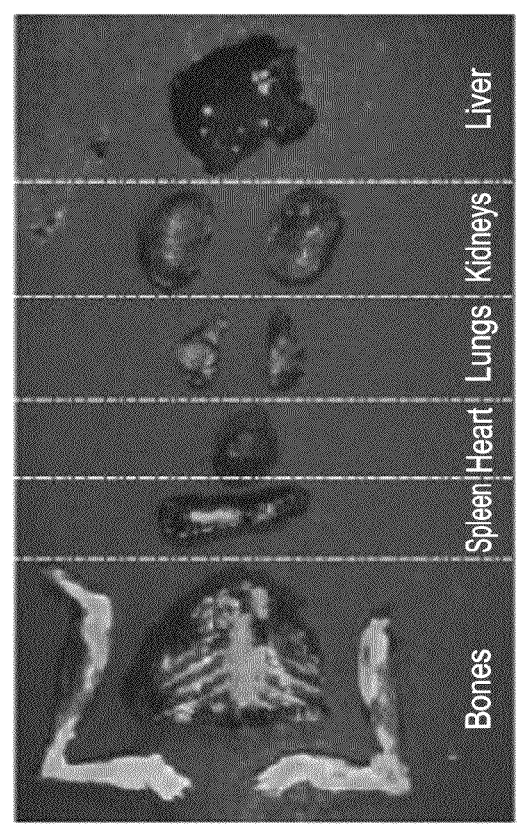

FIGS. 7A-G present data showing that HPMA copolymer-ALN-TNP-470 conjugate, according to some embodiments of the present invention, reduces vascular hyperpermeability in mouse skin capillaries and inhibits MG-63-Ras human osteosarcoma growth. FIG. 7A presents representative images showing diminished Evans Blue dye uptake in skin patches of mice treated with free ALN+TNP-470 or HPMA copolymer-ALN-TNP-470 conjugate as compared to untreated control group. Scale bar represents 10 mm. FIG. 7B presents bar graphs showing the extracted dye content taken from the skin patches of each mouse group and quantified by measurement at 620 nm (n=5 mice/group). FIG. 7C presents representative intravital non-invasive fluorescence images of mCherry-labeled MG-63-Ras tumor-bearing nontreated mice (control) or treated with free ALN+TNP-470 or HPMA copolymer-ALN-TNP-470 conjugate. FIG. 7D presents comparative plots showing antitumor effect of free ALN+TNP-470 (open triangles) or HPMA copolymer-ALN-TNP-470 conjugate (closed triangles) on MG-63-Ras human osteosarcoma tumor size compared to vehicle-treated group (closed squares) and dissected tumors images. Scale bar represents 10 mm. All p values are two-sided (n=5 mice/group). On day 19 HPMA copolymer-ALN-TNP-470 conjugate inhibited tumor growth by 96% (p=0.001) compared with 45% (p=0.012) of free ALN+TNP-470. Data represent mean±s.d.*p<0.05, p<0.03, *p<0.05 compared with control. FIG. 7E presents representative images from whole-mount confocal microscopy of mCherry-labeled MG-63-Ras human osteosarcoma tumors dissected from mice treated with FITC-labeled HPMA copolymer-ALN-TNP-470 conjugate. Scale bar represents 25 μm. FIG. 7F presents representative images of H & E and CD34 immunostaining of control, free ALN+TNP-470 combination, and HPMA copolymer-ALN-TNP-470 conjugate treated MG-63-Ras osteosarcomas inoculated s.c. in mice. FIG. 7G presents representative images of dissected organs of mice treated with FITC-labeled HPMA copolymer-ALN-TNP-470 conjugate showing greater intensity of FITC-fluorescence spectrum (green; composed images of unmixed multispectral cubes) in bone tissues then in the spleen, heart, lungs, kidneys and liver. Images were taken using the CRI Maestro™ intravital non-invasive fluorescence imaging system.

FIG. 8 presents a scheme illustrating the synthesis of two HPMA copolymer-D-$Asp_8$-TNP-470 conjugates (HP1 and HP2) (D-$Asp_8$ having SEQ ID NO:1) according to some embodiments of the present invention.

Figure 9:
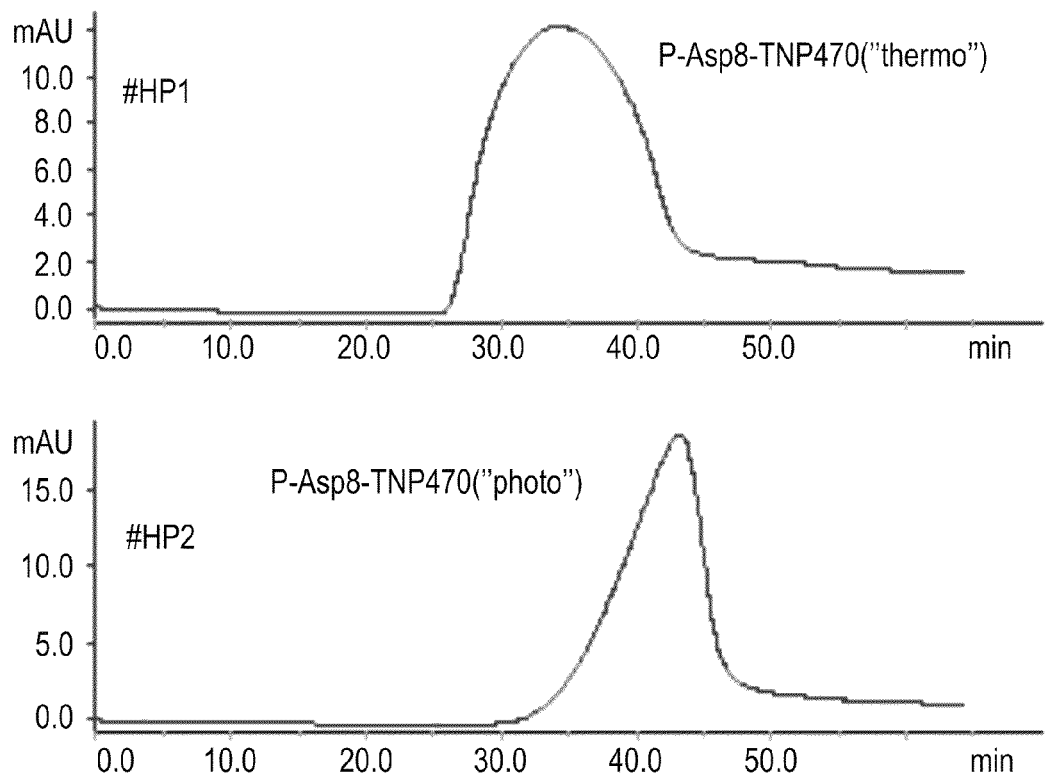

FIG. 9 presents a size exclusion chromatography (SEC) profile of two HPMA copolymer-D-$Asp_8$-TNP-470 conjugates (HP1 and HP2) (D-$Asp_8$ having SEQ ID NO:1).

Figure 10:
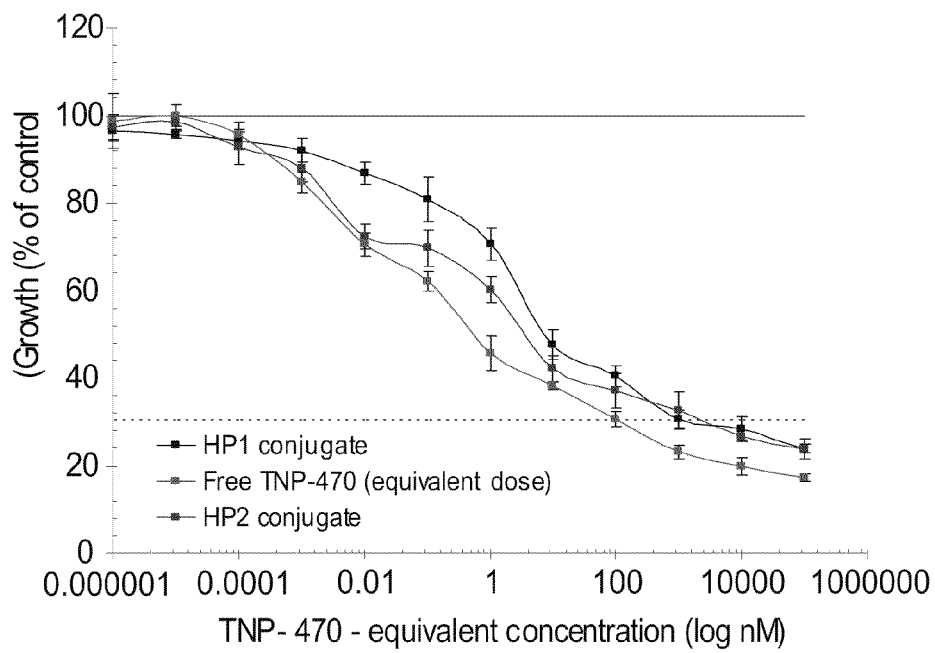

FIG. 10 presents comparative plots showing effect of free TNP-470 (orange squares), compared with HPMA-D-$Asp_8$-TNP-470 conjugates HP1 (black squares) and HP2 (blue squares) on the growth of HUVEC, demonstrating that TNP-470 retains its anti-angiogenic effect when bound to the HPMA copolymer (D-Asp$_8$ having SEQ ID NO:1).

Figure 11A:
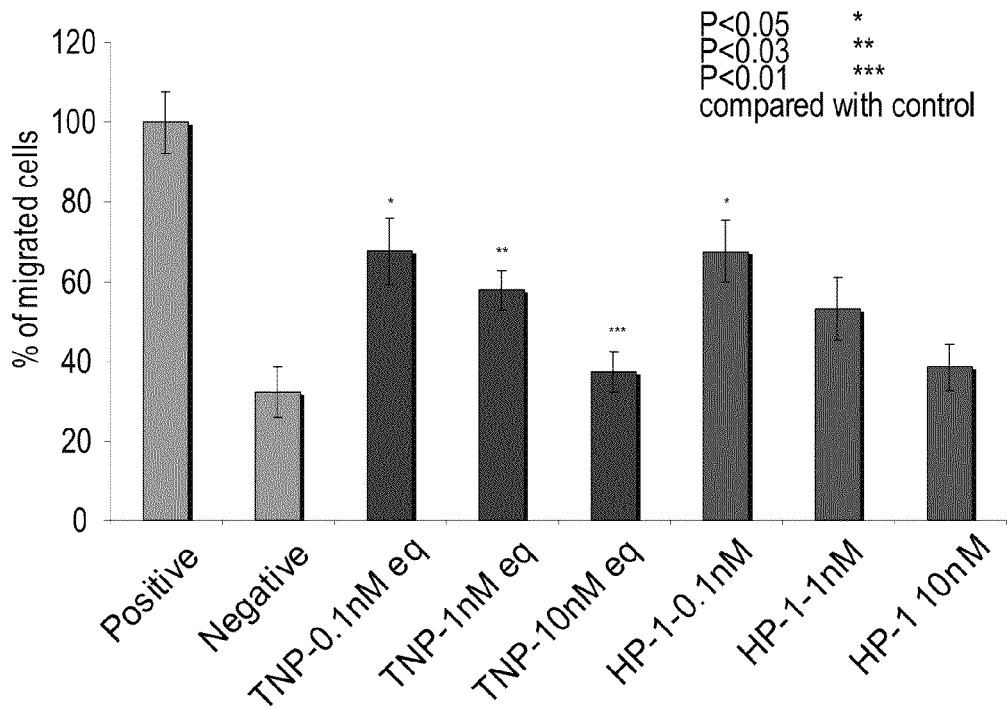
Figure 11B:
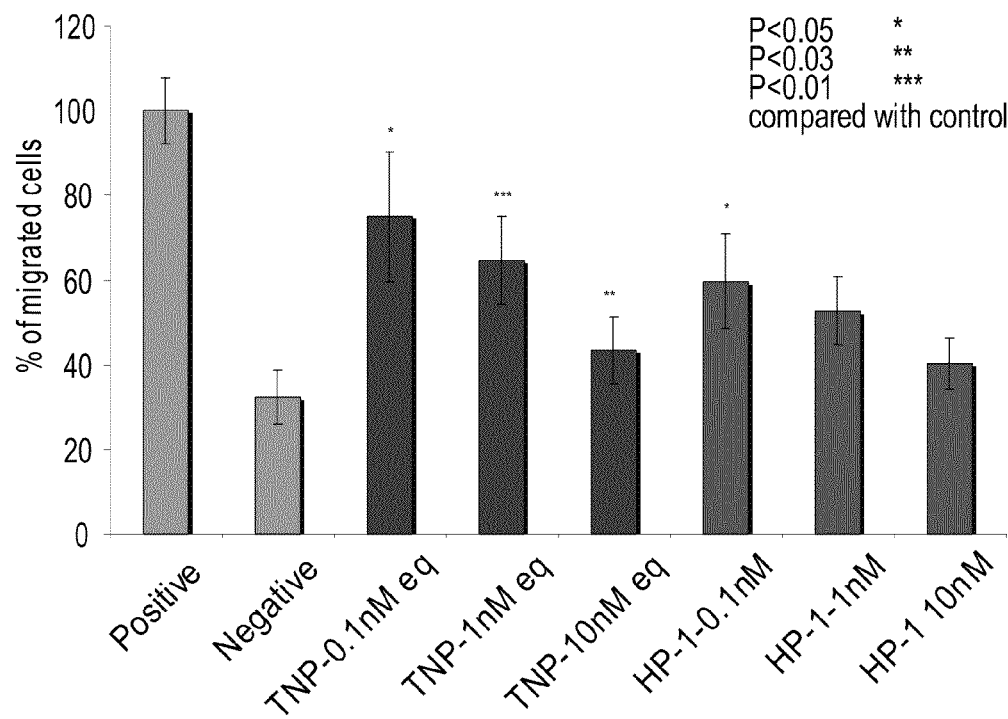

FIGS. 11A-B present bar graphs showing the effect of the HPMA-D-Asp$_8$-TNP-470 conjugates, HP1 (FIG. 11A) and HP2 (FIG. 11B), compared with free TNP-470, on the ability of HUVEC to migrate towards vascular endothelial growth factor (VEGF) chemoattractant, and demonstrating that free and polymer-conjugated TNP-470 inhibited VEGF-induced HUVEC migration to a similar extent.

Figure 12A:
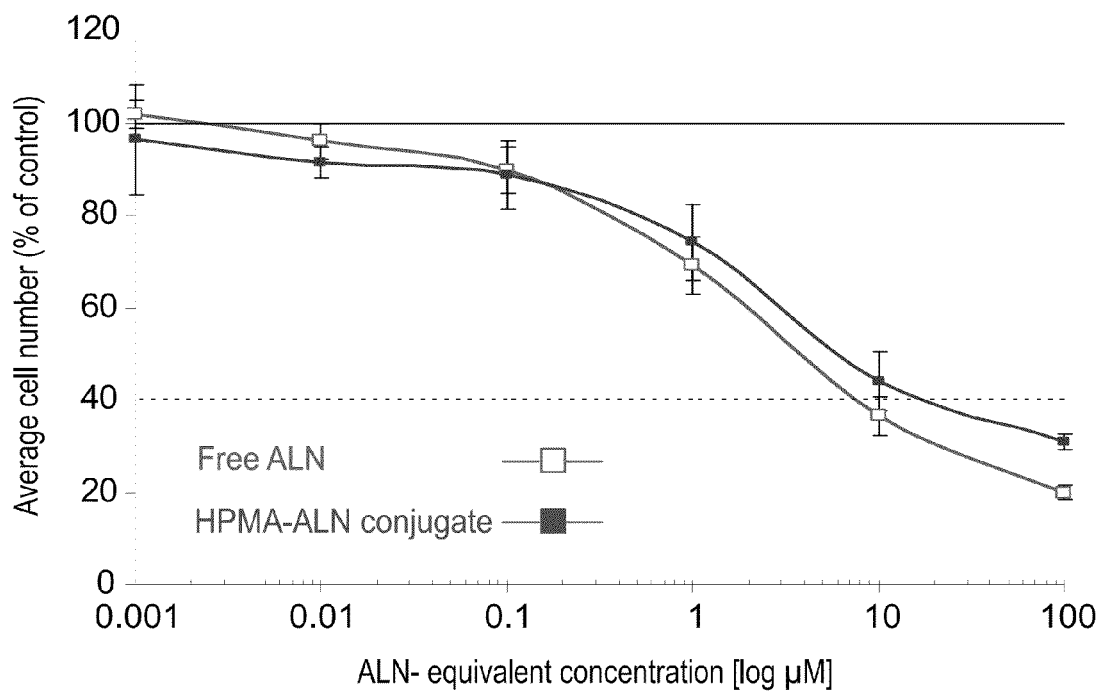
Figure 12B:
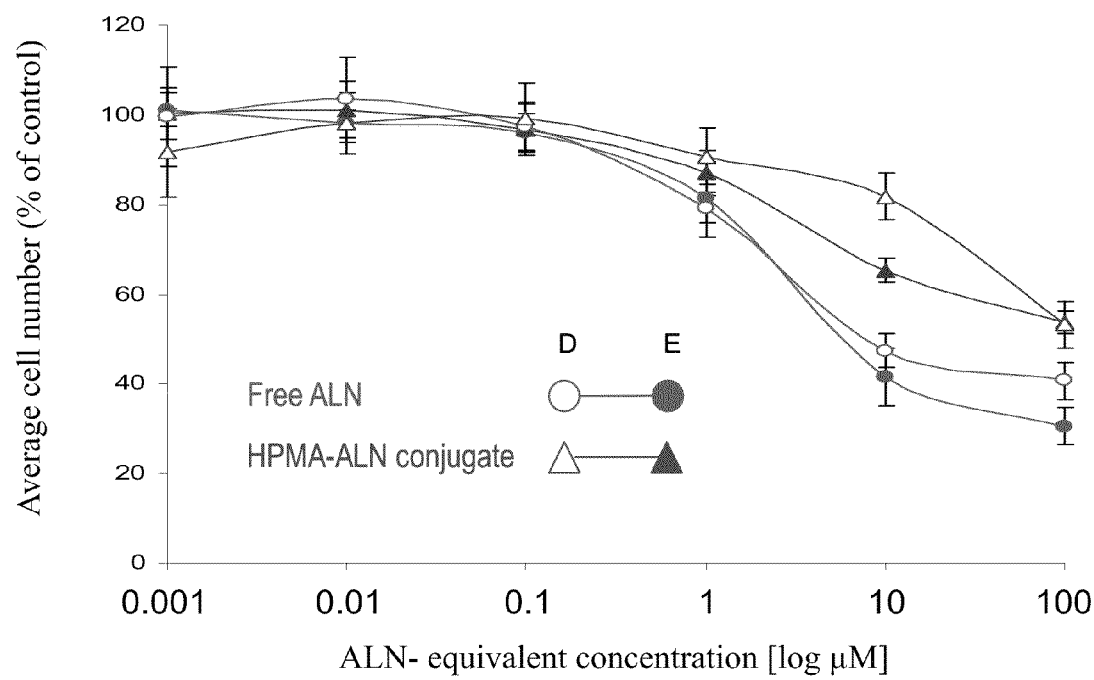

FIGS. 12A-B present comparative plots demonstrating that ALN exhibits an anti-angiogenic effect in a dose dependent manner. Shown in FIG. 12A are plots of the percentage of average HUVEC cell growth as a function of free ALN concentrations (red empty squares) and ALN conjugated to HPMA concentrations (1 mol % loading; filled blue squares). Shown in FIG. 12A are plots of the percentage of average aggressive type (E) Saos-2 human osteosarcoma cell growth as a function of free ALN concentrations (red filled circles); ALN conjugated to HPMA concentrations (1 mol % loading; filled blue triangles) as well as plots of the percentage of average dormant (D) type Saos-2 human osteosarcoma cell growth as a function of free ALN concentrations (empty filled circles) and ALN conjugated to HPMA (1 mol % loading; empty blue triangles) concentrations. Solid and dashed lines represent the proliferation of cells in the presence (solid line) or absence (dashed line) of growth factors. Data represent mean±SD.

DESCRIPTION OF SPECIFIC EMBODIMENTS OF THE INVENTION

The present invention, in some embodiments thereof, relates to chemical conjugates and their use in therapy and diagnosis and, more particularly, but not exclusively, to chemical conjugates of a polymer, an anti-angiogenesis agent and a targeting moiety, which are useful, for example, in the treatment and monitoring of bone related diseases and disorders such as bone cancer and bone metastases.

The principles and operation of the conjugates, compositions, use, methods and processes according to the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, currently known agents used for treating bone related cancer and other angiogenesis-related conditions, at doses where anti-tumor activity is achieved, are characterized by high toxicity, which limits their use.

The present inventors have now devised and successfully prepared and practiced novel conjugates of a copolymer having attached thereto an anti-angiogenesis agent and a bone targeting moiety.

More specifically, but not exclusively, the present inventors have devised and successfully practiced novel processes of preparing such conjugates, in which the bone targeting moiety is alendronate or an oligoaspartate.

The present inventors have devised and successfully practiced novel processes of preparing such conjugates in which alendronate is present in a relatively high load within the copolymer.

The present inventors have surprisingly uncovered that alendronate and TNP-470 can act in synergy in inhibition of angiogenesis. Taken together with the dose-dependent anti-angiogenic activity of alendronate, the alendronate high-loaded conjugates described herein are therefore characterized as highly potent agents for treating bone-related diseases and disorders.

As demonstrated in the Examples section that follows, the present inventors have successfully prepared and practiced a novel polymeric conjugate of a N-(2-hydroxypropyl)methacrylamide (HPMA) copolymer, having attached thereto TNP-470 and the bone targeting agent, alendronate (ALN), wherein the TNP-470 and alendronate are conjugated to backbone units of the HPMA-derived polymeric backbone via biodegradable linkers and the mol percent of alendronate loaded onto the conjugate is higher than in currently known alendronate-polymer conjugates (e.g., is greater than 3 mol % of the polymeric conjugate).

This polymeric conjugate exhibited an enhanced inhibition of angiogenesis and bone cancer as compared with un-conjugated, i.e., free, TNP-470 and ALN, administered at equivalent doses. Specifically, this HPMA copolymer-ALN-TNP470 conjugate was capable of binding to bone mineral (see, FIGS. 3B and 3C), and exhibited a superior activity, as compared to non-conjugated ALN and TNP-470, with regard to inhibition of osteosarcoma cell proliferation (see, FIG. 5), inhibition of endothelial cell proliferation and migration (see, FIGS. 5 and 6A respectively), inhibition of endothelial cell ability to form capillary tube structures (see, FIGS. 6B-C), and in reducing vascular hypermeability and osteosarcoma tumor growth in-vivo (see, FIG. 7).

The present inventors have further designed and successfully prepared and practiced a novel conjugate of a polymer (e.g., a N-(2-hydroxypropyl)methacrylamide (HPMA)-derived co-polymer) having attached thereto an anti-angiogenesis agent (e.g., TNP-470) and a bone targeting agent being D-Asp8 (SEQ ID NO:1).

Thus, according to one aspect of some embodiments of the invention there is provided a polymeric conjugate comprising an N-(2-hydroxypropyl)methacrylamide)-derived polymeric backbone having attached thereto TNP-470 and alendronate, wherein a load of the alendronate in the polymeric conjugate is greater than 3 mol %.

N-(2-hydroxypropyl)methacrylamide (HPMA) polymers are a class of water-soluble synthetic polymeric carriers that have been extensively characterized as biocompatible, non-immunogenic and non-toxic. HPMA polymers can be tailored through relatively simple chemical modifications, in order to regulate their respective drug and targeting moiety content. Further, the molecular weight and charge of these polymers may be manipulated so as to allow renal clearance and excretion from the body, or to alter biodistribution while allowing tumor targeting.

The tumor targeting capacity of HPMA polymers is attributed, at least in part, to the enhanced permeability and retention (EPR) effect of such polymers. Thus, HPMA conjugates are characterized by a limited diffusion and/or extravasation through normal blood vessels, due to the high molecular weight and hydrodynamic diameter thereof, and therefore accumulate selectively at the tumor site, which is characterized by leaky blood vessels having abnormal form and architecture and wide fenestrations, pores and vesicular vacuolar organelles (VVO). Due to the poor lymphatic drainage from tumor, macromolecules tend to be retained in the tumor microenvironment. Conjugating drugs to polymers such as HPMA is also expected to restrict the passage of the conjugate through the blood brain barrier, thus prolonging the circulating half-life of the drugs and abrogating neurotoxicity associated with many chemotherapeutic and anti-angiogenic drugs.

A polymeric conjugate, comprising an N-(2-hydroxypropyl)methacrylamide)-derived polymeric backbone having attached thereto TNP-470 and alendronate, that has a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of the polymeric conjugate can be determined while considering the half-life in plasma, the renal clearance, and the accumulation in the tumor of the conjugate. The molecular weight of the polymeric conjugate can be controlled, at least to some extent, by the degree of polymerization (or co-polymerization).

In some embodiments, the conjugate described herein has a MW that ranges from 100 Daltons to 800 kDa. In some embodiments, the conjugate described herein has a MW that ranges from 10 kDa to 800 kDa. In some embodiments, the conjugate has a MW that ranges from 10 kDa to 60 kDa.

In some embodiments of the invention, the conjugates described herein comprise an HPMA polymeric backbone comprised of N-(2-hydroxypropyl)methacrylamide-derived backbone units (a polymeric backbone formed by polymerizing N-(2-hydroxypropyl)methacrylamide monomers), whereby TNP-470 molecules are attached to a portion of these backbone units and alendronate molecules are attached to another portion of these backbone units, as described herein. Those backbone units within the polymeric backbone that are not linked to another moiety (e.g., TNP-470, alendronate, or any of the other moieties described herein) are referred to herein as "free" or "non-functionalized" backbone units.

Since the polymeric backbone in the conjugates described herein is composed of some backbone units that have alendronate attached thereto, some backbone units that have TNP-470 attached thereto, and optionally some free backbone units, these conjugates represent HPMA-derived co-polymers.

As discussed hereinabove, TNP-470 is a potent anti-angiogenesis agent. Its use as a free drug has been limited by its low solubility and dose-dependent neurotoxicity.

The phrase "anti-angiogenesis agent", which is also referred to herein interchangeably as "anti-angiogenic agent" or "angiogenesis inhibitor", describes an agent having the ability to (a) inhibit endothelial cell proliferation or migration; (b) kill proliferating endothelial cells; and/or (c) inhibit the formation of new blood vessels in a tissue.

As further discussed hereinabove, alendronate (4-amino-1-hydroxybutylidene)bisphosphonic acid) is a bisphosphonate which exhibits a strong affinity to bone minerals under physiological conditions.

Herein, the term "alendronate" also encompasses any pharmaceutically acceptable salts, solvates and/or hydrates thereof, as defined hereinafter.

It has been previously shown that alendronate exhibits anti-angiogenesis activity in a dose dependent manner. For example, Cheng et al. have shown that alendronate reduces the mRNA level and cellular level of Matrix metalloproteinase-2 (MMP-2) enzyme in osteosarcoma cell lines in a time and dose-dependent manner [Cheng et al. 2004, *Pediatr Blood Cancer* 42; 410-415].

As demonstrated in the Examples section that follows, the anti-angiogenesis activity of alendronate is dose dependent, as assessed by the extent of HUVEC and Saos-2 human osteosarcoma cell line proliferation inhibition, whereby the extent of inhibition is proportional to the alendronate concentrations, i.e., at higher alendronate concentration a stronger anti-angiogenesis activity could be observed.

Conjugating alendronate and an anti-angiogenesis agent to polymers is highly beneficial for producing an agent that is characterized by both selectivity, due to the EPR effect attributed to the polymer, and the bone-targeting effect attributed to the alendronate, and a potent therapeutic activity, due to the presence of a potent anti-angiogenesis agent.

However, such conjugates, which are further characterized by a high load of alendronate, as described herein, are even more potent, due to the dual targeting and anti-angiogenesis effect that can be potentially exhibited by the alendronate.

According to some embodiments of the invention, the conjugates described herein are characterized by an alendronate loading which is higher than 3 mol %.

Herein, the phrase "loading", or simply "load", and any grammatical diversion thereof, is used to describe the amount of an agent that is attached to the polymeric backbone of the conjugates described herein, and is represented herein by the mol % of this agent in the conjugate, as defined hereinafter.

As used herein, the term "mol %" describes the number of moles of an attached moiety per 1 mol of the polymeric conjugate, multiplied by 100.

Thus, for example, a 3 mol % load of alendronate describes a polymeric conjugate composed of 100 backbone HPMA units, whereby 3 HPMA backbone units have alendronate-containing monomer units attached thereto, and the other 97 HPMA backbone units are either free or have other agents attached thereto.

In the conjugates described herein, the load of alendronate can be, for example, 3, 3.1, 3.2, 3.3, 3.4, 3.5, 4, 4.5, 5, 5.5, 6, 6.5, 7, 7.5, 8, 8.5, 9, 9.5 and even as high as 10 mol %.

In some embodiments, the load of the alendronate in the polymer is greater than 5 mol %.

In some embodiments, the load of the alendronate in the polymer is about 7 mol %.

Herein, the phrase "about" describes ±1%.

Thus, the phrase "about 7 mol %" describes a mol percentage ranging between 6 mol % and 8 mol %, or between 6.5 mol % and 7.5 mol %. For example, this phrase encompasses 6.5 mol %, 6.6 mol %, 6.7 mol %, 6.8 mol %, 6.9 mol %, 7 mol %, 7.1 mol %, 7.2 mol %, 7.3 mol %, 7.4 mol % and 7.5 mol %.

As demonstrated in the Examples section that follows, at such high loads, alendronate can exhibit both a bone targeting effect and an anti-angiogenesis effect.

As further demonstrated in the Examples section that follows, it has been further surprisingly uncovered that a combined therapy of TNP-470 and alendronate results in a synergistic anti-angiogenic activity, when alendronate is utilized at a high concentration.

As demonstrated in the Examples section that follows, the anti-angiogenesis activity of alendronate and TNP-470, when administered together, as demonstrated by their inhibitory effect on the proliferation of endothelial cells, was superior to the cumulative anti-angiogenesis activity of each agent when administered alone (see, FIG. 2). This synergistic activity could be observed only at high alendronate concentration whereas at low alendronate concentration (lower than 100 nM), no synergistic activity could be detected. These results show that the synergistic activity between alendronate and TNP-470 is dose-dependent. As further demonstrated in the Examples section that follows, the in vivo inhibition of osteosarcoma tumor growth in mice was significantly enhanced when conjugating both TNP-470 and alendronate to HPMA, with a high load of alendronate (see, FIG. 7D), as compared to the inhibition observed when equivalent concentration of free alendronate and free TNP-470 were administered (i.e., unconjugated). It can therefore be clearly deduced that the synergistic anti-angiogenesis activity results from the relatively high concentration (load) of alendronate within the conjugate.

Since alendronate exhibits a dose-dependent anti-angiogenesis activity, and further since it is shown herein that alendronate and TNP-470 can act in synergy in inhibition of angiogenesis, such high-loaded conjugates can be beneficially utilized in the treatment of bone-related diseases and disorders such as those conditions that are associated with angiogenesis.

Thus, in some embodiments of the invention, the TNP-470 and alendronate that are attached to the polymer in the conjugates described herein act in synergy.

The phrase "synergy" or "synergistic activity", as used herein and in the art, describes a cooperative action encountered in combinations of two or more biologically active agents in which the combined effect exhibited by the two agents when used together exceeds the sum of the effect of each of the agents when used alone.

"Synergy" or "synergistic activity" is therefore often determined when a value representing an effect of a combination of two active agents is greater than the sum of the same values obtained for each of these agents when acting alone.

A synergy between two anti-angiogenesis agents may be determined by methods well known in the art.

In each of the conjugates described herein, the alendronate and the TNP-470 can each be linked to the polymeric backbone directly, or indirectly, through a linker moiety (also referred to herein as a linker, a linker group or a linking group), whereby, in some embodiments, the direct/indirect linkage is designed as being cleavable at conditions characterizing the environment of a desired bodily site (e.g., by certain enzymes or pH), as detailed hereinbelow.

Hence, according to some embodiments of the invention, at least one of the TNP-470 and the alendronate is attached to the polymeric backbone via a linker. In some embodiments, each of the TNP-470 and the alendronate is attached to the polymeric backbone via a linker. The linker linking the TNP-470 to the polymer and the linker linking the alendronate to the polymeric backbone may be the same or different.

The linker described herein refers to a chemical moiety that serves to couple the TNP-470 and/or the alendronate to the polymeric backbone while not adversely affecting either the targeting function of the alendronate or the therapeutic effect of the alendronate and/or the TNP-470.

In some embodiments, the linker is a biodegradable linker. The phrase "biodegradable linker", as used herein, describes a linker that is capable of being degraded, or cleaved, when exposed to physiological conditions. Such physiological conditions can be, for example, pH, a certain enzyme, and the like.

In some embodiments, the linker is capable of being cleaved by pre-selected cellular enzymes, for instance, those found in osteoblasts, osteoclasts, lysosomes of cancerous cells or proliferating endothelial cells. Alternatively, an acid hydrolysable linker could comprise an ester or amide linkage and be for instance, a cis-aconityl linkage. Such linkers further enhance the therapeutic activity and reduced toxicity of the conjugates described herein, by allowing the release of the anti-angiogenesis drug and/or the alendronate only at the desired bodily site.

Accordingly, according to some embodiments, the biodegradable linker is a pH-sensitive linker or an enzymatically-cleavable linker.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents attached to the polymer in the body, until its reaches a physiological environment where a pH is either acidic or basic, respectively.

Exemplary pH-sensitive linkers include, but are not limited to hydrazone bond, ester (including orthoesther) bonds, amide bonds of a cis-aconytil residue, a trityl group, acetals, ketals, Alanine ester, Gly-ester and a -[Gly-Phe-Gly]- moiety (SEQ ID NO:4).

In some embodiments, the biodegradable linker is an enzymatically-cleavable linker. Such a linker is typically designed so as to include a chemical moiety, typically, but not exclusively, an amino acid sequence, that is recognized by a pre-selected enzyme. Such an amino acid sequence is often referred to in the art as a "recognition motif". A conjugate comprising such a linker typically remains substantially intact in the absence of the pre-selected enzyme, and hence does not cleave or degrade so as to the release the agent attached thereto until it reaches an environment where this enzyme is present at a substantial concentration.

In some embodiments, the enzymatically cleavable linker is cleaved by an enzyme which is expressed in tumor tissues. A conjugate comprising such a linker ensures, for example, that a substantial amount of the conjugated TNP-470 is released from the conjugate only at the tumor tissue, thus reducing the side effects associated with the non-selective administration of the drug.

In some embodiments, the enzymatically cleavable linker is cleaved by an enzyme which is overexpressed in tumor tissues.

Exemplary enzymes which are suitable for use in the context of these embodiments include, but are not limited to, Cathepsin B, Cathepsin K, Cathepsin D, Cathepsin H, Cathepsin L, legumain, MMP-2 and MMP-9.

Suitable linkers include, but are not limited to, alkyl chains; alkyl chains optionally substituted with one or more substituents and in which one or more carbon atoms are optionally interrupted by a nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone and the alendronate, the polymeric backbone and the TNP-470). Such a functionalization may include incorporation or generation of reactive groups that participate in such covalent bindings.

In some embodiments, the linker is a biodegradable oligopeptide which contains, for example, from 2 to 10 amino acid residues.

In some embodiments, the linker is a Cathepsin K-cleavable linker.

Cathepsin K is a lysosomal cysteine protease involved in bone remodeling and resorption and is predominantly expressed in osteoclasts. Its expression is stimulated by inflammatory cytokines that are released after tissue injury and in bone neoplasms [Pan et al. 2006, *J Drug Target* 14:425-435; Husmann et al. 2008, *Mol Carcinog* 47: 66-73]. An exemplary linker having Cathepsin K cleavable sites is -[Gly-Gly-Pro-Nle]- (SEQ ID NO: 3).

In some embodiments, the linker comprises the amino acid sequence -[Gly-Gly-Pro-Nle]- (SEQ ID NO: 3).

In some embodiments, the linker consists of the amino acid sequence -[Gly-Gly-Pro-Nle]- (SEQ ID NO: 3).

Other Cathepsin K cleavable sites are those that include a -[Gly-Pro-Nle]- moiety (SEQ ID NO: 5). Another example include [-Gly-Gly-NH—C6-Gly-Pro-Nle]- (SEQ ID NO: 6).

As demonstrated in the Examples section that follows, a Cathepsin K cleavable linker being -[Gly-Gly-Pro-Nle]- (SEQ ID NO:3) was used, linking both alendronate and TNP-470 to the HPMA polymeric backbone (see, FIG. 1). As further demonstrated in the Examples section that follows, a HPMA copolymer-ALN-TNP-470 conjugate comprising such linker moieties successfully inhibited proliferation of endothelial cells as well as Saos-2 and MG-63-Ras human osteosarcoma cells. The involvement of Cathepsin K in the release of the TNP-470 and alendronate from the polymer could be deduced from the reduced activity of the conjugate when incubated together with a cathepsin K inhibitor whereby the conjugate inhibited the proliferation of HUVEC at a 4-logs higher concentration in the presence of cathepsin K inhibitor III than in its absence (see, FIG. 5).

An oligopeptide linker which contains the pre-selected amino acid sequence (recognition motif) can also be constructed such that the recognition motif is repeated several times within the linker, to thereby enhance the selective release of the attached agent. Various recognition motifs of the same or different enzymes can also be incorporated within the linker. Similarly, the linker may comprise multiple pH sensitive bonds or moieties. Linkers comprising such multiple cleavable sites can enhance the selective release of the anti-angiogenesis agent at the desired bodily site, thereby reducing adverse side effects, and further enhance the relative concentration of the released drug at the bodily site when it exhibits its activity.

In cases where the TNP-470 and/or the alendronate is bound directly to the polymeric backbone, the bond linking these moieties can also be biodegradable, for example, an enzymatically-cleavable bond or a pH-sensitive bond (e.g., an acid-hydrolyzable bond). Such a bond can be formed upon functionalizing backbone units of the polymeric backbone, the alendronate and/or the TNP-470, so as to include compatible reactive groups for forming the desired bond.

In some embodiments, the TNP-470 is linked to the polymer or to the linker via a spacer. In some embodiments, the alendronate is linked to the polymer or to the linker via a spacer. The spacers can be the same or different.

The term "spacer" as used herein describes a chemical moiety that is covalently attached to, and interposed between, the polymeric backbone and the linker, the TNP-470 and/or the alendronate, thereby forming a bridge-like structure between the polymeric backbone and the linker, the TNP-470 and/or the alendronate. In some embodiments, the spacer does not actively participate in a biological process, and is present in the conjugate for the purpose of facilitating its synthesis and/or improving its performance in terms of, for example, steric considerations, as is detailed hereinbelow.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the polymeric backbone, TNP-470 and/or alendronate.

In some embodiments, the spacer has the formula G-($CH_2$)n-K, wherein n is an integer from 1 to 10; and G and K are each a reactive group, as defined herein, such as, for example, NH, O or S. In some embodiments, G and K are each NH and n is 2.

In some embodiments, the spacer is an amino acid sequence, optionally an inert amino acid sequence (namely, does not affect the affinity or selectivity of the conjugate). Such a spacer can be utilized for elongating or functionalizing the linker.

In some cases, a spacer is utilized for enabling a more efficient and simpler attachment of the alendronate and/or the TNP-470 to the polymeric backbone or linker, in terms of steric considerations (renders the site of the polymeric backbone to which coupling is effected less hindered) or chemical reactivity considerations (adds a compatible reactive group to the site of the polymeric backbone to which coupling is effected). In some cases, the spacer may contribute to the performance of the resulting conjugate. For example, the spacer may render an enzymatically cleavable linker less sterically hindered and hence more susceptible to enzymatic interactions.

The spacer may also be used in order to attach other agents (e.g., a labeling agent, as described hereinbelow) to the conjugate.

The spacer may be varied in length and in composition, depending on steric and chemical considerations, and may be used to space the TNP-470 and alendronate form the polymeric backbone and/or the linker.

As demonstrated in the Examples section that follows, the present inventors have successfully synthesized a conjugate wherein the TNP-470 is linked to the HPMA polymeric backbone via a cathepsin K cleavable linker being -[Gly-Gly-Pro-Nle]- (SEQ ID NO: 3) and a spacer being —NH—($CH_2$)$_2$—NH— (see, FIG. 1).

As discussed hereinabove, the degree of loading of the TNP-470 and alendronate may be expressed as mole %, as defined herein.

The optimal degree of loading of TNP-470 is determined empirically based on the desired properties of the conjugate (e.g., water solubility, therapeutic efficacy, pharmacokinetic properties, toxicity and dosage requirements), and synthetic considerations (e.g., the amount of the drug that can be attached to the backbone units in a certain synthetic pathway).

In some embodiments, the loading of TNP-470 in the polymer is greater than 1 mol %.

In some embodiments, the loading of the TNP-470 in the conjugate ranges from 1 mol % to 90 mol %, from 1 mol % to 50 mol %, from 1 mol % to 20 mol %, from 1 mol % to 10 mol %, or from 1 mol % to 5 mol %.

The number of backbone units in the polymeric backbone having TNP-470 attached thereto is defined herein as "y", the number of backbone units in the polymeric backbone having alendronate attached thereto is herein defined as "w" and the number of free backbone units in the polymeric backbone (which are not bound to an additional moiety) is herein defined as "x".

Accordingly, in some embodiments, the conjugate described herein can be represented by the general formula II:

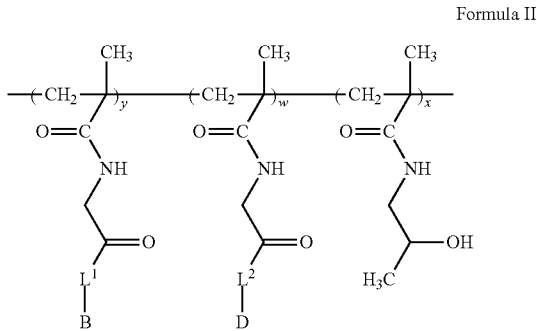

Formula II wherein:

x is an integer having a value such that x/(x+y+w) multiplied by 100 is in the range of from 0.01 to 99.9;

y is an integer having a value such that y/(x+y+w) multiplied by 100 is in the range of from 0.01 to 99.9; and w is an integer having a value such that w/(x+y+w) multiplied by 100 is in the range of from 3 to 99; B is TNP-470;

D is alendronate; and each of $L_1$ and $L_2$ is independently the linker, as described herein.

In some embodiments, the conjugate has the following structure:

wherein x, y and z are as defined herein.

According to some embodiments of the invention, x is an integer having a value such that x/(x+y+w) multiplied by 100 is in the range of from 70 to 99.9; y is an integer having a value such that y/(x+y+w) multiplied by 100 is in the range of from 0.01 to 15; and w is an integer having a value such that w/(x+y+w) multiplied by 100 is in the range of from 5 to 20.

For example, x/(x+y+w) multiplied by 100 may be 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9; y/(x+y+w) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15; and w/(x+y+w) multiplied by 100 may be 5, 5.2, 5.4, 5.6, 5.8, 6, 6.2, 6.4, 6.6, 6.8, 7, 7.2, 7.4, 7.6, 7.8, 8, 8.5, 9, 9.5, 10, 11, 12, 13, 14, 15, 16, 17, 18, 19 or 20. In some embodiments w/(x+y+w) multiplied by 100 is 7.

In some embodiments, the conjugate described herein further comprises a labeling agent attached thereto.

In some embodiments, the labeling agent is attached to a portion of the backbone units that do not have the TNP-470 or the alendronate attached thereto.

In such cases the number of backbone units in the polymeric backbone having the labeling agent attached thereto is defined as "z", as shown in the general Formula hereinbelow.

The attachment of a labeling agent to the conjugate enables utilizing these conjugates for monitoring bone related disease or disorders, for example, monitoring the therapeutic effect exhibited by the conjugate described herein, as well as its biodistribution.

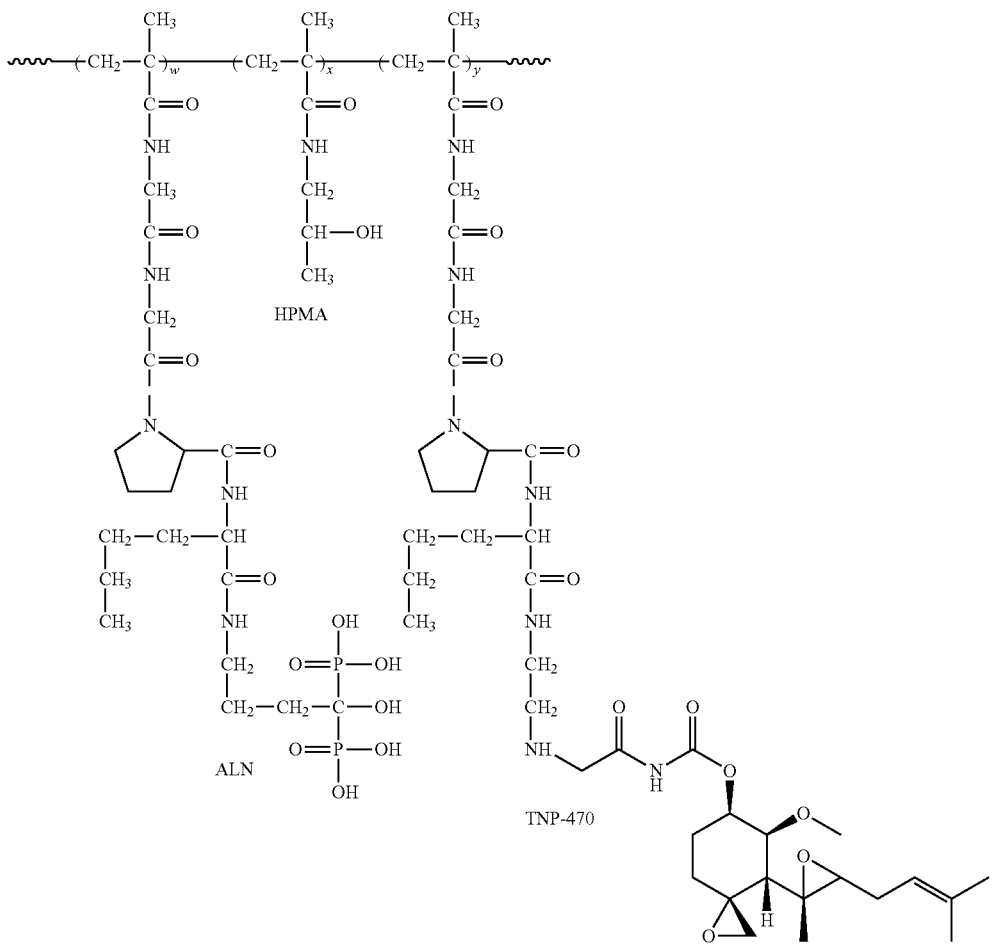

As used herein, the phrase "labeling agent" describes a detectable moiety or a probe. Exemplary labeling agents which are suitable for use in the context of the these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}$Tc, $^{18}$F, $^{131}$I and $^{125}$I.

The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

In some embodiments, the labeling agent is Fluorescein isothiocyanate.

As demonstrated in the Examples section that follows, a fluorescent agent being Fluorescein isothiocyanate (FITC) has been conjugated to HPMA copolymeric backbone having TNP-470 and alendronate attached thereto (HPMA copolymer-ALN-TNP-470-FITC; see, FIG. 1). The fluorescent agent was utilized for assessing the in vivo biodistribution of the conjugate (see, FIG. 7G) as well as to study the mechanism by which the conjugate internalize into endothelial and human osteosarcoma cells (see, FIG. 4). These fluorescence studies showed that the conjugate is mainly distributed to bone tissue and that the mechanism by which the conjugate is internalized is through a lysosomotropic pathway of cellular uptake via clathrin-coated vesicles.

In some embodiments, the conjugate has the following structure:

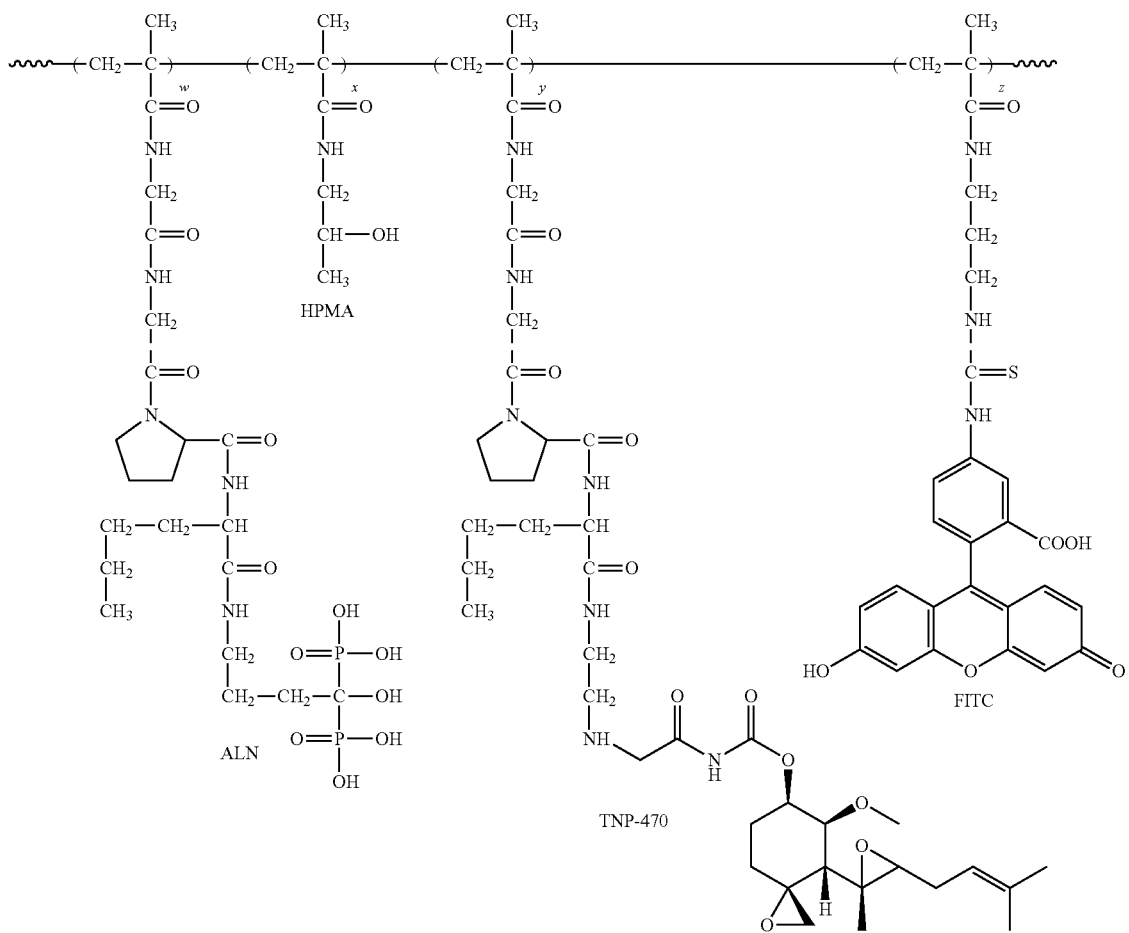

wherein:

x is an integer having a value such that x/(x+y+w+z) multiplied by 100 is in the range of from 0.01 to 99.9, as described herein;

y is an integer having a value such that y/(x+y+w+z) multiplied by 100 is in the range of from 0.01 to 99.9, as described herein;

w is an integer having a value such that w/(x+y+w+z) multiplied by 100 is in the range of from 2.1 to 99, as described herein; and z is an integer having a value such that z/(x+y+w+z) multiplied by 100 is in the range of from 0.01 to 99.9.

In some embodiments, z is an integer having a value such that z/(x+y+w+z) multiplied by 100 is in the range of from 0.01 to 10, and depends on the labeling agent utilized and the monitoring technology.

As discussed hereinabove and is further discussed in detail hereinbelow, the conjugates described herein were successfully prepared by devising and successfully practicing novel processes for their preparation. Such processes, in addition to allowing obtaining a conjugate with a high load of alendronate, further allow for obtaining conjugates having a low polydispersity index (PDI) and small mean size distribution.

Hence, in some embodiments, the conjugate described herein has a polydispersity index ranging from 1 to 1.4.

The term "polydispersity index" is a measure of the distribution of molecular mass in a given polymer sample. PDI is a value calculated as the weight average molecular weight divided by the number average molecular weight ($M_w/M_n$). It indicates the distribution of individual molecular masses in a batch of polymers. The PDI has a value always greater than 1, but as the polymer chains approach uniform chain length, the PDI approaches unity (1). Polymer-based nanocarriers similar to HPMA copolymer often exhibit inherent structural heterogeneity of the polymers, reflected in a high PDI value, typically higher than 1.4, and even higher than 1.6. Homogenous size distribution of polymer conjugates may contribute to a more defined biodistribution.

For example, the PDI value may be 1.39, 1.38, 1.37, 1.36, 1.35, 1.34, 1.33, 1.32, 1.31, 1.3, 1.29, 1.28, 1.27, 1.26, 1.25, 1.24, 1.26, 1.25, 1.24, 1.23, 1.22, 1.21, 1.2, 1.19, 1.18, 1.17, 1.16, 1.15, 1.14, 1.13, 1.12, 1.11, 1.1, 1.09, 1.08, 1.07, 1.06, 1.05, 1.04, 1.03, 1.02, and 1.01.

In some embodiments, the conjugate described herein has a mean size distribution lower than 150 nm.

For example, the mean size distribution may be lower than 149 nm, 148 nm, 147 nm, 146 nm, 145 nm, 143 nm, 142 nm, 141 nm, 140 nm, 139 nm, 138 nm, 137 nm, 136 nm, 135 nm, 134 nm, 133 nm, 132 nm, 131 nm, 130 nm, 129 nm, 128 nm, 127 nm, 126 nm, 125 nm, 124 nm, 123 nm, 122 nm, 121 nm, 120 nm, 119 nm, 118 nm, 117 nm, 116 nm, 115 nm, 114 nm, 113 nm, 112 nm, 111 nm, 110 nm, 109 nm, 108 nm, 107 nm, 106 nm, 105 nm, 104 nm, 103 nm, 102 nm, 101 nm, 100 nm, 99 nm, 97 nm, 95 nm, 93 nm, 91 nm, 89 nm, 87 nm, 85 nm, 83 nm, 81 nm, 79 nm, 77 nm, 75 nm, 73 nm, 71 nm, 69 nm, 67 nm, 65 nm, 63 nm, 61 nm, 55 nm, 50 nm, 45 nm, 40 nm, 35 nm, 30 nm, 25 nm, 20 nm, 15 nm etc.

Weight average molar mass ($M_w$) was evaluated for the conjugates synthesized from their SEC profiles and the Polydispersity index (PDI) was calculated according to the formula $M_w/M_n$.

While reducing the present invention to practice, the present inventors have designed and successfully practiced a novel process for preparing a HPMA co-polymer having attached thereto alendronate, TNP-470 and optionally a labeling agent (e.g., a fluorescent agent), whereby the load of the alendronate is greater than in currently known methodologies for attaching bisphosphonates, and optionally other targeting moieties, to polymers.

Currently known methodologies typically include attachment of a targeting moiety to an already prepared polymer or co-polymer, and thus, the load of the targeting moiety in the resulting conjugate is limited and non-controllable.

In contrast, in the methodology described herein, monomeric units of the polymeric backbone (HPMA) to which alendronate is attached are first prepared and then co-polymerized with HPMA monomeric, oligomeric and/or polymeric units. Alternatively, the alendronate-containing monomeric units are polymerized and then co-polymerized with other monomeric, oligomeric or polymeric units of the monomer. In some embodiments, co-polymerization is effected upon converting at least a pre-determined portion of the HPMA monomers, oligomers or polymers to such that terminate with a reactive group that is capable of reacting with TNP-470 (e.g., by means of adding a spacer that terminates with the desired reactive group), thereby functionalizing the HPMA monomers.

In some embodiments, co-polymerization is effected upon converting at least a pre-determined portion of the HPMA monomers, oligomers or polymers to such that terminate with a reactive group that is capable of reacting with a labeling agent (e.g., by means of adding a spacer that terminates with the desired reactive group).

In some embodiments, co-polymerization is effected upon converting at least a pre-determined portion of the HPMA monomers, oligomers or polymers to such that include a linker, as described herein, which optionally terminates with a reactive group that is capable of reacting with TNP-470 (e.g., by means of adding a spacer that terminates with the desired reactive group).

Hence, according to another aspect of some embodiments of the present invention, there is provided a process of synthesizing the conjugates described herein, the process comprising:

(a) coupling alendronate to N-(2-hydroxypropyl)methacrylamide monomeric units, to thereby obtain alendronate-containing methacrylamide monomeric units;

(b) co-polymerizing N-(2-hydroxypropyl)methacrylamide monomeric units, and/or a ((N-(2-hydroxypropyl)methacrylamide) oligomeric or polymeric units with the alendronate-containing methacrylamide monomeric units and with N-(2-hydroxypropyl)methacrylamide-derived monomeric units terminating with a first reactive group, to thereby obtain a polymeric backbone which comprises a plurality of methacrylamide backbone units in which a portion of the backbone units has an alendronate attached thereto, and another portion of the backbone units has the reactive group, the first reactive group being capable of coupling TNP-470; and (c) coupling the TNP-470 and the polymeric backbone via the first reactive group, thereby obtaining the polymeric conjugate.

In some embodiments, the process further comprises, optionally prior to the co-polymerizing in (b), coupling a labeling agent to N-(2-hydroxypropyl)methacrylamide monomeric units, to thereby obtain labeling agent-containing methacrylamide monomeric units; and (b) further comprises copolymerizing the labeling agent-containing methacrylamide monomeric units together with alendronate-containing methacrylamide monomeric units and N-(2-hydroxypropyl)methacrylamide-derived monomeric units terminating with a first reactive group, to thereby obtain an alendronate-containing copolymer having the reactive group, and labeling agent, the reactive group being capable of coupling TNP-470.

Alternatively, the co-polymerization in (b) comprises co-polymerizing the alendronate-containing monomeric units with the N-(2-hydroxypropyl)methacrylamide monomeric units and/or the ((N-(2-hydroxypropyl)methacrylamide) oligomeric or polymeric units and the N-(2-hydroxypropyl) methacrylamide-derived monomeric units terminating with a first reactive group, and further with N-(2-hydroxypropyl) methacrylamide-derived monomeric units terminating with a second reactive group, wherein the second reactive group is being capable of coupling the labeling agent.

In these embodiments, the process further comprises coupling the labeling agent to the co-polymer, via the second reactive group. Such a coupling can be effected prior to, concomitant with, or subsequent to coupling the TNP-470.

The copolymerization of the alendronate-containing HPMA monomers and the other, functionalized or non-functionalized HPMA monomers can be effected by any polymerization method known in the art, using suitable polymerization initiators and optionally chain transfer agents. Such suitable polymerization initiators and chain transfer agents can be readily identified by a person skilled in the art.

As demonstrated in the Examples section that follows, the copolymerization of alendronate containing HPMA-derived monomers+HPMA-derived monomers terminating with a reactive group (e.g., ethylenediamine)+free HPMA monomers, and optionally + an HPMA-derived monomer comprising FITC (step (b) in the process described hereinabove), was performed via two methodologies: (1) the "classical" thermopolymerization methodology using, as an example, 4,4'-azobis(4-cyanovaleric acid) as a polymerization initiator; and (2) the "reversible addition-fragmentation chain transfer" (RAFT) polymerization technique, using, as an example, 2,2'-Azobis[2-(2-imidazolin-2-yl)propane]dihydrochloride as a polymerization initiator and S,S'-bis($\alpha,\alpha'$-dimethyl-$\alpha''$-acetic acid)trithiocarbonate as a chain transfer agent (TTC).

Using these two synthetic approaches, it was shown that the load of alendronate in the conjugate, as well as other parameters of the obtained copolymer, can be finely controlled.

Using the RAFT approach further enables to perform the copolymerization at room temperature or at temperatures as low as 30° C.

The "reversible addition-fragmentation chain transfer" (RAFT) polymerization technique typically involves the use of thiocarbonylthio compounds, such as dithioesters, dithiocarbamates, trithiocarbonates, and xanthates in order to mediate the polymerization via a reversible chain-transfer process. This allows access to polymers with low polydispersity and high functionality.

As exemplified in the Examples section that follows, weight average molar mass ($M_w$) was determined for the conjugates synthesized from their SEC profiles and the Polydispersity index (PDI) was calculated according to the formula $M_w/M_n$. It has been shown that conjugates polymerized by RAFT were well-dispersed, exhibiting a considerably low and narrower PDI value of about 1.2, with a mean size distribution of 100 nm (see, FIGS. 3D-G).

Therefore, in some embodiments, the co-polymerizing is performed via the Reversible addition-fragmentation chain transfer (RAFT) technique.

In some embodiments, the process is performed such that the conjugate has a polydispersity index ranging from 1 to 1.4.

In some embodiments, the process is performed such that the conjugate has a mean size distribution lower than 150 nm.

Generally, the TNP-470 or alendronate can be attached to the monomeric units that form the polymeric backbone, or to the backbone units of the copolymer, by means of a functional group that is already present in the native molecule and/or the monomeric units of the polymer, or otherwise can be introduced or generated by well-known procedures in synthetic organic chemistry without altering the activity of the agent. For example, in the case of alendronate, a terminal carboxylic group can be generated within a monomeric HPMA, in order to form an amide with the amine functional group of alendronate. A carboxylic functional group can be generated, for example, by oxidizing the hydroxy group of the HPMA. Alternatively, a carboxylic functional group (reactive group) is generated by attaching to an HPMA monomer a spacer or a linker that terminates with a carboxylic group.

Similarly, an alkylhalide can be generated within the HPMA polymeric backbone or within HPMA monomers, in order to readily couple TNP-470. Such an alkylhalide can be generated by means of a spacer and/or linker, as described herein.

HPMA monomeric, oligomeric and polymeric units that have been modified so as to generate a reactive group are therefore referred to herein as HPMA-derived units or as methacrylamide units terminating by a reactive group.

Accordingly, in some embodiments, the process further comprises introduction of a linker to at least some of the HPMA monomeric, oligomeric or polymeric units participating in the co-polymerization.

In some embodiments, introducing the linker is performed subsequent to the co-polymerization.

Similarly, in some embodiments, the process further comprises introduction of a spacer to at least some of the HPMA monomeric, oligomeric or polymeric units participating in the co-polymerization.

In some embodiments, introducing the spacer is performed subsequent to the co-polymerization.

In some embodiments, a plurality of functionalized HPMA monomeric units is first prepared. The functionalized HPMA monomers include: HPMA monomers that include a spacer and/or a linker for attaching alendronate; HPMA monomers that include a spacer and/or a linker for attaching TNP-470; and optionally HPMA monomers that include a spacer for attaching a labeling agent. These functionalized HPMA monomeric units are referred to herein as HPMA-derived units.

Then, alendronate-containing HPMA-derived monomers are prepared, and are co-polymerized with the other functionalized HPMA monomers, optionally in the presence of non-modified HPMA monomers (which form "free" backbone units upon co-polymerization).

In some embodiments, alendronate-containing methacrylamide monomeric are prepared by first preparing N-methacryloylglycylglycylprolylnorleucine units (SEQ ID NO:7), and thereafter conjugating thereto the alendronate, so as to obtain N-methacryloylglycylglycylprolylnorleucyl-alendronate monomeric units (SEQ ID NO:8).

In some embodiments, HPMA-derived methacrylamide units that terminate with a first reactive group include N-methacryloylglycylglycylprolylnorleucine units (SEQ ID NO:7).

In some embodiments, HPMA-derived methacrylamide units that terminate with a second reactive group include N-methacryloylglycylglycyl units (SEQ ID NO:9).

Since attaching alendronate, a labeling agent, a spacer and/or a linker to HPMA units, or otherwise generating a reactive group within the HPMA unit, involves reaction with the 2-hydroxypropyl group in these units, such functionalized HPMA units are also referred to herein as methacrylamide units that contain the above-described moieties or groups.

Co-polymerization is effected as described hereinabove.

Then, TNP-470 is coupled to the formed co-polymer.

The order of steps can be modified, as long as alendronate is attached to monomeric HPMA units, prior to co-polymerization of such units, in order to assure a high and controllable load of alendronate.

Herein, the phrases "functional group" and "reactive group" are used interchangeably. Accordingly, "functionalized" monomers (monomeric units), oligomers, etc. describe such monomers, oligomers, etc. that have a reactive group, as defined and described herein.

The present inventors have utilized some of the methodologies described herein for introducing another targeting moiety into a polymer conjugate that further comprises a therapeutically active agent such as an anti-angiogenesis agent.

Thus, the present inventors have further designed and successfully prepared and practiced novel conjugates of a polymer (e.g., a N-(2-hydroxypropyl)methacrylamide (HPMA) copolymer), an anti-angiogenesis agent (e.g., TNP-470) and a bone targeting agent being an oilgoaspartate (e.g. D-Asp$_8$ (SEQ ID NO: 1)).

As demonstrated in the Examples section that follows, an HPMA copolymer having TNP-470 and D-Asp$_8$ (SEQ ID NO: 1) attached thereto has been prepared (HPMA copolymer-D-Asp$_8$-TNP-470; see, FIG. 8). The anti-angiogenesis activity of the conjugate has been demonstrated by the ability to inhibit the proliferation of HUVEC by the conjugate (see, FIG. 10) and inhibition of vascular endothelial growth factor (VEGF)-induced HUVEC migration (FIG. 11).

These results suggest that the use of these conjugates for treating bone and bone related disorders (such as cancer and disorders characterized by angiogenesis), is beneficial.

Therefore, according to another aspect of some embodiments of the present invention there is provided a polymeric conjugate comprising a polymeric backbone having attached thereto an anti-angiogenesis agent and a bone targeting moiety, the bone targeting moiety being an oligopeptide of aspartic acid which comprises from 2 to 100 aspartic acid residues.

The term "anti-angiogenesis agent" is as defined hereinabove.

The phrase "bone targeting moiety" describes a compound having the capability of preferentially accumulating in hard tissues (i.e. bone tissues) rather than any other organ or tissue, after administration in vivo.

Oligopeptides of aspartic acid such as D-aspartate octapeptide (D-Asp$_8$) (SEQ ID NO: 1) have been known to accumulate in bone. These oligopeptides bind to Hydroxyapitate (HA), the major constituent of the bone, thereby being suitable for serving as a bone targeting moiety.

As defined hereinabove the oligopeptide of aspartic acid described herein comprises from 2 to 100 aspartic acid residues. Therefore, such oligopeptides may comprise 2, 3, 4, 5, 6, 7, 8, 9, 10, 11, 12, 13, 14 15, 16, 17, 18, 19, 20, 25, 30, 35, 40, 45, 50, 55, 60, 65, 70, 75, 80, 85, 90, 95, 100 etc. aspartic acid residues.

In some embodiments the oligopeptide of aspartic acid comprises from 2 to 20 aspartic acid residues. In some embodiments the oligopeptide of aspartic acid comprises 8 aspartic acid residues (Asp$_8$). In some embodiments the oligopeptide of aspartic acid consists of 8 aspartic acid residues (Asp$_8$, SEQ ID NO:10).

The oligopeptide can further include other amino acid residues, as long as it includes one or more amino acid sequences that consist of two or more aspartic acid residues. In some embodiments, such amino acid sequences consist of 2 to 20 aspartic acid residues or of 8 aspartic acid residues.

The aspartic acid can be D-aspartic acid and/or L-aspartic acid. In some embodiments, the aspartic acid is D-aspartic acid.

In some embodiments, the anti-angiogenesis agent is TNP-470.

Other anti-angiogenesis agents useful in the context of these embodiments of the invention include, but are not limited to, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, marimastat, a matrix metalloproteinase, penicillamine, PTK787/ZK 222584, RPI.4610, squalamine lactate, SU5416, thalidomide, combretastatin, tamoxifen, COL-3, neovastat, BMS-275291, SU6668, anti-VEGF antibody, Medi-522 (Vitaxin II), CAI, Interleukin-12, IM862, Amilloride, Angiostatin®Protein, Angiostatin K1-3, Angiostatin K1-5, Captopril, DL-alpha-Difluoromethylornithine, DL-alpha-Difluoromethylornithine HCl, His-Tag® Endostatin™ Protein, Fumagillin, Herbimycin A, 4-Hydroxyphenylretinamide, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Neutrophil Granulocyte, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3 and 2-ME2.

In some embodiments, the anti-angiogenesis agent is selected from the group consisting of Paclitaxel, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3; 2-ME2 and Bisphosphonates (e.g., Zoledronate).

As used herein, the term "COX-2 inhibitor" refers to a non-steroidal drug that relatively inhibits the enzyme COX-2 in preference to COX-1. Preferred examples of COX-2 inhibitors include, but are no limited to, celecoxib, parecoxib, rofecoxib, valdecoxib, meloxicam, and etoricoxib.

In some embodiments, the polymeric conjugates described herein are composed of a polymeric backbone, formed from a plurality of backbone units that are covalently linked to one another, wherein at least a portion of this plurality of backbone units has an anti-angiogenesis agent, as described herein, attached thereto, and at least another portion of the plurality of backbone units has the bone targeting moiety (the oligoaspartate, as described herein), attached thereto.

Those backbone units that have the anti-angiogenesis agent attached thereto and those backbone units that have the oligoaspartate attached thereto can be randomly dispersed within the polymeric backbone.

The polymeric backbone can further include non-functionalized backbone units, as discussed hereinbelow, to which none of the anti-angiogenesis agent and the oligoaspartate are attached.

In some embodiments, the polymeric backbone of the conjugates described constitutes polymers (or co-polymers) to which the anti-angiogenesis agent and the bone targeting moiety are attached.

Polymers which are suitable for use in the context of the present embodiments are preferably biocompatible, non-immunogenic and non-toxic. The polymers serve as carriers that enable specific delivery into tumor tissue, possible due to the EPR effect described hereinabove.

As used herein, the term "polymer" describes an organic substance composed of a plurality of repeating structural units (backbone units) covalently connected to one another. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

The polymer is comprised of backbone units formed by polymerizing the corresponding monomeric units whereby the anti-angiogenesis agent and the bone targeting moiety are attached to at least a portion of the backbone units. Some or all of these backbone units are typically functionalized prior to conjugation so as to have a reactive group for attaching the anti-angiogenesis agent and the bone targeting moiety. Those backbone units that are not functionalized and/or do not participate in the conjugations of the anti-angiogenesis agent and bone targeting moiety are referred to herein as "free" backbone units.

The polymer may be a biostable polymer, a biodegradable polymer or a combination thereof. The term "biostable", as used in this context of embodiments of the invention, describes a compound or a polymer that remains intact under physiological conditions (e.g., is not degraded in vivo).

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of embodiments of the present invention, also encompasses the term "bioresorbable", which describes a substance that decomposes under physiological conditions to break down products that undergo bioresorption into the host-organism, namely, become metabolites of the biochemical systems of the host-organism.

The polymers can be water-soluble or water-insoluble. In some embodiments, the polymers are water soluble at room temperature.

The polymers can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the polymer has an average molecular weight in the range of 100 Da to 800 kDa. In some embodiments, the polymer has an average molecular weight lower than 60 kDa. In some embodiments, the polymer's average molecular weight ranges from 10 kDa to 40 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The molecular weight of the polymer can be controlled, at least to some extent, by the degree of polymerization (or co-polymerization).

The polymer used in the context of these embodiments of the invention can be a synthetic polymer or a naturally-occurring polymer. In some embodiments, the polymer is a synthetic polymer.

The polymeric backbone of the polymer described herein may be derived from, for example, polyacrylates, polyvinyls, polyamides, polyurethanes, polyimines, polysaccharides, polypeptides, polycarboxylates, and mixtures thereof.

Exemplary polymers which are suitable for use in the context of the present embodiments include, but are not limited to the group consisting of dextran, a water soluble polyamino acid, a polyethylenglycol (PEG), a polyglutamic acid (PGA), a polylactic acid (PLA), a polylactic-co-glycolic acid, (PLGA), a poly(D,L-lactide-co-glycolide) (PLA/PLGA), a poly(hydroxyalkylmethacrylamide), a polyglycerol, a polyamidoamine (PAMAM), and a polyethylenimine (PEI).

These polymers can be of any molecular weight, as described herein.

In some embodiments, the polymeric backbone is derived from a poly(hydroxyalkylmethacrylamide) or a copolymer thereof. Such a polymeric backbone comprises methacrylamide backbone units having attached thereto either 2-hydroxypropyl groups or such 2-hydroxypropyl groups that have been modified by attaching thereto (directly or indirectly) the moieties described herein (the oligoaspartate and the anti-angiogenesis agent).

It is to be understood that the polymers as discussed herein describe those polymers that are formed from homogenic or heterogenic, non-functionalized monomeric units, and that the polymeric backbone constituting the polymeric conjugate corresponds to such polymers by being comprised of the same monomeric units, while some of these monomeric units are functionalized, as described herein. Thus, the polymeric backbone of the polymeric conjugate is similar to that of the polymers described herein, and differs from the polymers by having the above-described agents attached to some of the backbone units therein.

In each of the conjugates described herein, the bone targeting moiety and the anti-angiogenesis agent can each be linked to the respective portion of the backbone units in the polymeric backbone directly, or indirectly, through a linker moiety (also referred to herein as a linker, a linker group or a linking group), whereby, in some embodiments, the direct/indirect linkage is designed as being cleavable at conditions characterizing the desired bodily site (e.g., by certain enzymes or pH), as detailed hereinbelow.

Hence, according to some embodiments of the invention, at least one of the anti-angiogenesis agent and the bone targeting moiety is attached to the polymer via a linker. In some embodiments, each of the anti-angiogenesis agent and the bone targeting moiety is attached to the polymer via a linker. The linker linking the anti-angiogenesis agent to the polymer and the linker linking the bone targeting moiety to the polymer may be the same or different.

The linker described herein refers to a chemical moiety that serves to couple the anti-angiogenesis agent and/or the bone targeting moiety to the polymer while not adversely affecting either the targeting function of the bone targeting moiety or the therapeutic effect of the anti-angiogenesis agent.

The linker characteristics have been described elaborately hereinabove.

In some embodiments, each of the anti-angiogenesis agent and the bone targeting moiety is attached to the polymer via a linker. In such a case, the linker linking the anti-angiogenesis agent and the linker linking the bone targeting moiety may be the same or different.

In some embodiments, only the anti-angiogenesis agent is linked to the polymer via a biodegradable linker, thereby being released from the polymer at the desired bodily site.

As demonstrated in the Examples section that follows, a HPMA copolymer of TNP-470 and D-Asp$_8$ (SEQ ID NO: 1) has been synthesized using the biodegradable linker -[Gly-Gly-Pro-Nle]- (SEQ ID NO: 3) in order to link TNP-470 to the polymer.

As discussed hereinabove, an exemplary linker is a Cathepsin K cleavable linker.

Hence, in some embodiments, the linker is an enzymatically-cleavable linker. In some embodiments the enzymatically-cleavable linker is cleaved by an enzyme which is expressed in tumor tissues. In some embodiments the enzymatically-cleavable linker is cleaved by an enzyme which is overexpressed in tumor tissues.

Exemplary enzymes which are suitable for use in the context of the present embodiments include, but are not limited to Cathepsin B, Cathepsin K, Cathepsin D, Cathepsin H, Cathepsin L, legumain, MMP-2 and MMP-9.

As discussed hereinabove, Cathepsin K is expressed predominantly in osteoclasts. Therefore, in some embodiments the enzymatically-cleavable linker is cleaved by Cathepsin K.

In some embodiments the biodegradable linker comprises an oligopeptide having from 2 to 10 amino acid residues.

As discussed hereinabove, a Cathepsin K cleavable linker being -[Gly-Gly-Pro-Nle]- (SEQ ID NO: 3) has been used by the present inventors in order to conjugate TNP-470 to a HPMA polymer (see FIG. 8). Accordingly, in some embodiments, the linker comprises -[Gly-Gly-Pro-Nle]- (SEQ ID NO: 3).

In some embodiments, the bone targeting moiety described in the context of these embodiments of the invention is attached to the polymeric backbone via a biostable linker.

In some embodiments, the bone targeting moieties attached to the polymeric backbone via an enzymatically cleavable linker, for example, a Cathepsin K cleavable linker as described hereinabove.

In some cases, the conjugate described herein comprise an additional spacer moiety which enables a more efficient and simpler attachment of the anti-angiogenesis agent and/or the bone targeting moiety to the polymeric backbone. The spacer may be further utilized in order to attach a labeling agent to the conjugate. Such a spacer has been described extensively hereinabove.

As illustrated in the example section that follows hereinbelow, spacers comprising a —[NH—(CH$_2$)$_2$—NH]— group and a 1-aminohaxanoyl have been used, intradispersly, in order to conjugate TNP-470 through a -[Gly-Gly-Pro-Nle]- (SEQ ID NO: 3) Cathepsin K cleavable linker to the HPMA copolymer (see, FIG. 8). Spacers derived from 1-aminohexaonoic acid were used intradispersly in order to attach D-Asp$_8$ (SEQ ID NO: 1) and a labeling agent being FITC to the polymer (see, FIG. 8).

In some embodiments, the conjugate may further comprise a labeling agent, as defined herein. Such a labeling agent is described elaborately hereinabove. In some embodiments, the labeling agent is attached to the conjugate via a spacer, as described herein. As demonstrated in the Examples section that follows, a labeling agent being Fluorescein isothiocyanate (FITC) has been conjugated to a HPMA copolymer-D-Asp$_8$-TNP-470 via the spacer used to couple the D-Asp$_8$ (the D-Asp$_8$ having an ID SEQ NO: 1) (see, FIG. 8).

The degree of loading of the anti-angiogenesis agent and the bone targeting moiety may be expressed as mol %, as defined herein.

Thus, for example, a 1 mol % load of a bone targeting moiety describes a polymeric conjugate composed of 100 backbone units, whereby 1 backbone unit has a targeting moiety attached thereto and the other 99 backbone units are either free or have other agents attached thereto.

The optimal degree of loading of the anti-angiogenesis agent and bone targeting moiety for a given conjugate and a given use is determined empirically based on the desired properties of the conjugate (e.g., water solubility, therapeutic efficacy, pharmacokinetic properties, toxicity and dosage requirements), and optionally on the amount of the conjugated moiety that can be attached to a polymeric backbone in a synthetic pathway of choice.

The % loading can be measured by methods well known by those skilled in the art, some of which are described hereinbelow under the Materials and Methods of the Examples section that follows.

In some embodiments, the loading of the anti-angiogenesis agent in the polymer is greater than 1 mol %.

In some embodiments, the loading of the anti-angiogenesis agent in the conjugate ranges from 1 mol % to 99 mol %, from 1 mol % to 50 mol %, from 1 mol % to 20 mol %, from 1 mol % to 10 mol %, or from 1 mol % to 5 mol %.

In some embodiments the loading of the bone targeting moiety in the polymer is greater than 1 mol %.

In some embodiments, the loading of the bone targeting moiety in the conjugate ranges from 1 mol % to 99 mol %, from 1 mol % to 50 mol %, from 1 mol % to 20 mol %, from 1 mol % to 10 mol %, or from 1 mol % to 5 mol %.

The number of backbone units within the polymeric backbone that have an anti-angiogenesis agent conjugated thereto is defined herein as "a", the number of backbone units within the polymeric backbone that have a bone targeting moiety conjugated thereto is herein defined as "b" and the number of free backbone units in the polymeric backbone (which are not bound to an additional moiety) is herein defined as "d".

Accordingly, in some embodiments, the conjugate described herein can be represented by the general formula I:

$$[A_1]d[A_2\text{-}L_1\text{-}B]a[A_3\text{-}L_2\text{-}D]b \qquad \text{Formula I}$$

wherein:

a is an integer having a value such that x/(x+y+w) multiplied by 100 is in the range of from 0.01 to 99.9;

b is an integer having a value such that y/(x+y+w) multiplied by 100 is in the range of from 0.01 to 99.9; and d is an integer having a value such that w/(x+y+w) multiplied by 100 is in the range of from 0.01 to 99.9;

$A_1$, $A_2$ and $A_3$ are each backbone units covalently linked to one another and forming the polymeric backbone, wherein:

B is the anti-angiogenesis agent as defined hereinabove;

D is the bone targeting moiety as defined hereinabove; and each of the $L_1$ and $L_2$ is independently a linker as defined hereinabove;

such that [$A_2$-$L_1$-B] is a backbone unit having attached thereto the anti-angiogenesis agent; and

[$A_3$-$L_2$-B] is a backbone unit having attached thereto the bone targeting moiety;

wherein each of the [$A_1$], the [$A_2$-$L_1$-B] and the [$A_3$-$L_2$-D] is either a terminal backbone unit being linked to one of the [$A_1$], the [$A_2$-$L_1$-B] and the [$A_3$-$L_2$-D], or is linked to at least two of the [$A_1$], the [$A_2$-$L_1$-B] and the [$A_3$-$L_2$-B] and the $A_1$, $A_2$ and/or $A_3$ are linked to one another to thereby form the polymeric backbone.

In embodiments where the polymeric conjugate is derived from HPMA, $A_1$ is a hydroxypropylmethacrylamide unit; and $A_2$ and $A_3$ is a methacrylamide unit, as discussed hereinabove.

In some embodiments, the conjugate described herein can be represented by the general formula IIa:

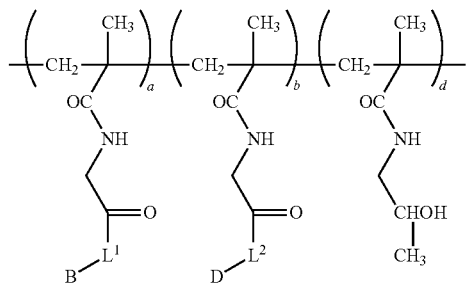

wherein a, b and d are as defined herein.

In some embodiments the conjugate has the following structure:

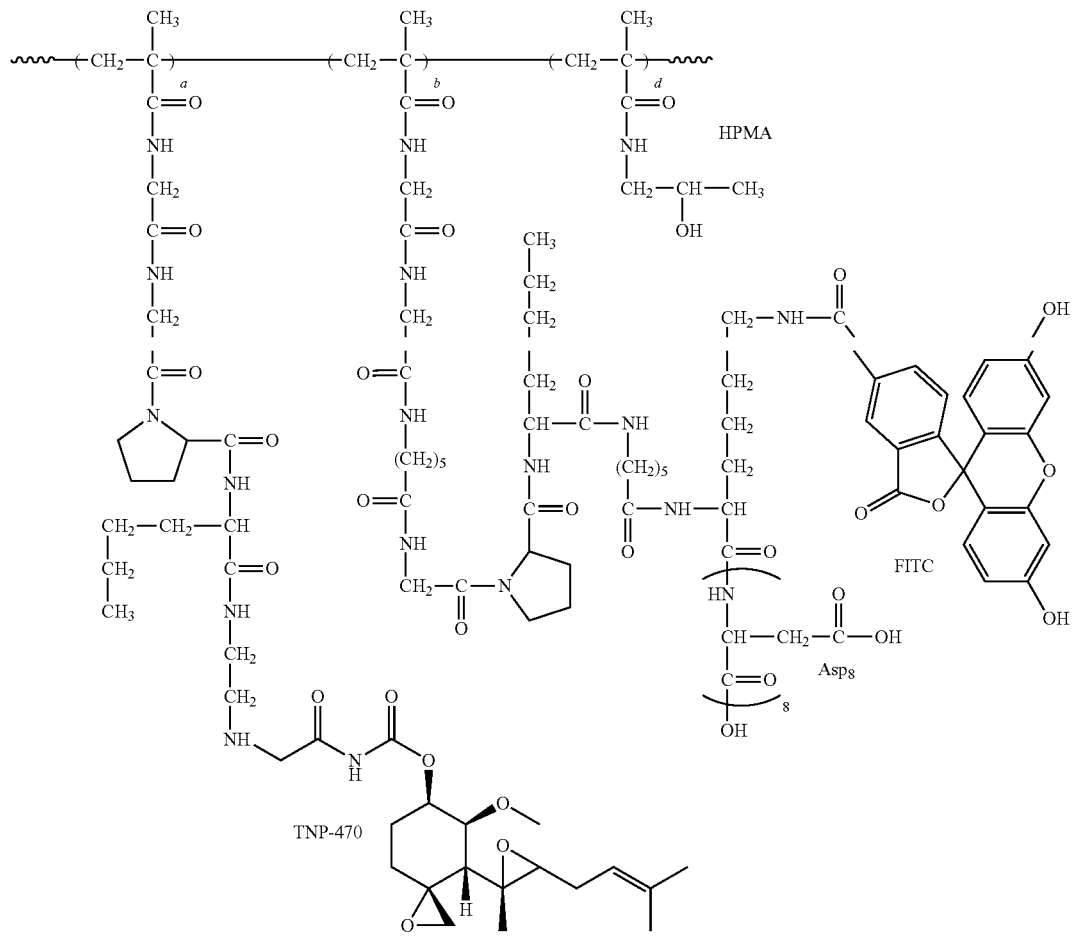

wherein a and b are each independently an integer having a value such that a/(a+b+d) multiplied by 100 and/or b/(a+b+d)×100 are in the range of from 0.01 to 15; and d is an integer having a value such that d/(a+b+d) multiplied by 100 is in the range of from 70 to 99.9.

It would be appreciated that a, b and d can be controlled as desired by selecting the mol ratio of the respective monomeric units used for forming the polymeric conjugate.

According to another aspect of some embodiments of the present invention, there is provided a process for preparing the conjugates described herein. The process, according to these embodiments, is effected by:

(a) co-polymerizing a plurality of monomeric units of said polymeric backbone, wherein a portion of said plurality comprises monomeric units terminating by a first reactive group, and another portion of said plurality comprises monomeric units terminating by a second reactive group, to thereby obtain a co-polymer comprising a polymeric backbone that comprises a plurality of backbone units, wherein a portion of said backbone units has said first reactive group and another portion of said backbone units has said second reactive group, said first reactive group being capable of reacting with said anti-angiogenesis agent and said second reactive being capable of reacting with said bone targeting moiety;

(b) coupling the bone targeting moiety to the co-polymer via the first reactive group, thereby obtaining a bone targeting moiety-containing copolymer; and (c) coupling the anti-angiogenesis agent to the co-polymer via the second reactive group; thereby obtaining the conjugate.

The phrase "oligomeric units of the polymer", or simply "oligomeric units", as used herein throughout, describes a polymer comprised of 2-50 backbone units. Hence, the polymeric backbone of the conjugate described herein may be constructed by copolymerizing the functionalized monomeric units, as described hereinabove, together with non-functionalized monomeric or oligomeric units that compose the backbone.

In some embodiments, each of the functionalized monomeric units can first be polymerized, so as to form a functionalized oligomer bearing a plurality of the first reactive groups and a functionalized oligomer bearing a plurality of the second reactive groups, and these oligomers can be co-polymerized with each other and with the non-functionalized oligomeric or monomeric units.

In some embodiments, only one of the functionalized monomeric units is polymerized so as to form a functionalized oligomer, which is then co-polymerized with the other functionalized monomeric units and non-functionalized monomeric or oligomeric units.

As used herein throughout, the term "functionalized" describes a monomer or an oligomer that terminates with one or more reactive groups.

As used herein throughout, a "reactive group" describes a chemical group that is capable of reacting with another group so as to form a chemical bond, typically a covalent bond. Optionally, an ionic or coordinative bond is formed.

A reactive group is termed as such if being chemically compatible with a reactive group of an agent or moiety that should be desirably attached thereto. For example, a carboxylic group is a reactive group suitable for conjugating an agent or a moiety that terminates with an amine group, and vice versa.

A reactive group can be inherently present in the monomeric units, oligomeric units and/or bone targeting moiety and the anti-angiogenesis agent, or be generated therewithin by terms of chemical modifications of the chemical groups thereon or by means of attaching to these chemical groups a spacer or a linker that terminates with the desired reactive group, as described herein.

Co-polymerizing the monomers or oligomers described herein can be effected by any of the polymerization methods known in the art, using suitable polymerization initiators or any other catalysts known in the art.

As discussed hereinabove, it has been shown that co-polymerization via the Reversible addition-fragmentation chain transfer (RAFT) technique yields conjugates having a low polydispersity index and small mean size distribution.

Therefore, in some embodiments, the co-polymerization is performed via the reversible addition-fragmentation chain transfer (RAFT) technique, as exemplified in the Examples section that follows.

In some embodiments, the anti-angiogenesis agent is conjugated to the polymer prior to the conjugation of the bone targeting moiety. In some embodiments, the bone targeting moiety is coupled to the polymer prior to conjugating the anti-angiogenesis agent.

Each of the first and the second reactive groups can be protected prior to the respective conjugation thereto. In such cases, the process further comprises deprotecting each of the reactive groups prior to the respective conjugation.

This allows a controlled conjugation of, for example, the anti-angiogenesis agent to those backbone units that comprises a biodegradable linker.

It should be appreciated that the monomeric units, spacers and linkers utilized for coupling the anti-angiogenesis agent and/or the bone targeting moiety to the polymer are designed so as to allow a smooth and efficient conjugation of the respective moiety and an optimal performance of the obtained conjugate, as discussed elaborately hereinabove.

Thus, in some embodiments, the process is further effected by preparing the monomeric units or oligomeric units that comprise the first and second reactive groups.

In some embodiments, monomeric units having attached thereto a spacer terminating with a protected first reactive group are prepared. Exemplary such monomeric units are methacrylamide units (derived from HPMA, as defined herein) having attached thereto a protected Gly-Gly group (SEQ ID NO:11).

Similarly, monomeric units having attached thereto a linker and optionally a spacer, terminating with a protected second reactive group are prepared.

The ratio between the above-described monomeric units and non-functionalized monomeric or oligomeric units that form a part of the formed polymer determines, at least in part, the mol ratio of the respective bone targeting moiety and anti-angiogenesis moiety in the formed conjugate.

Co-polymerizing the monomeric and/or oligomeric units bearing the reactive groups results in a functionalized polymer, bearing the first and second reactive groups (optionally protected with respective protecting groups).

In some embodiments, the bone targeting moiety and/or the anti-angiogenesis moiety are modified prior to being conjugated to the functionalized polymer, so as to include reactive groups that are compatible with the first and second reactive groups, respectively, of the functionalized polymer.

Such a modification can be effected by means of attaching a spacer and/or a linker to the bone targeting moiety and/or the anti-angiogenesis agent prior to the conjugation thereof to the functionalized polymer.

Hence, in some embodiments, the process is further effected by preparing such modified bone targeting moiety and/or anti-angiogenesis agent.

The linkers and/or spacers interposed between the polymeric backbone and the moieties conjugated thereto are designed so as to exhibit the properties described elaborately hereinabove with respect thereto.

Similarly, embodiments of the process described herein also apply for other processes described herein (e.g., for preparing a HPMA copolymer-alendronate-TNP-470 conjugate as described herein).

The spacer may be varied in length and in composition depending on steric consideration and may be used to space the angiogenesis agent and/or bone targeting moiety form the polymer, thereby enabling easier synthesis of the conjugate and/or improved performance of the formed conjugate, as detailed hereinabove.

In some embodiments the process further comprises attaching a labeling agent, as defined herein, to the formed conjugate. The labeling agent can be attached to either of functionalized monomeric units, prior to co-polymerization or to the formed co-polymer.

In some embodiments, the labeling agent is attached to the co-polymer concomitantly with the bone targeting moiety. Alternatively, it is attached prior to or subsequent to attaching the bone targeting moiety and/or the anti-angiogenesis agent.

In some embodiments, the process comprises co-polymerizing, along with the functionalized and non-functionalized monomeric or oligomeric units described herein, monomeric units terminating with a third reactive group, the third reactive group being for conjugating thereto a labeling agent or any other additional moiety, as described herein.

Thus, each of the conjugates described in any of the embodiments of the invention, may further include an additional moiety conjugated thereto. Such an additional moiety can be conjugated either to monomeric units within and throughout the polymeric backbone, or be attached at one or both ends of the polymeric backbone.

Such an additional moiety can be a labeling agent, as described herein, or an additional targeting moiety or an additional therapeutically active agent, which may improve the performance of the formed conjugate. Such an additional moiety can further be a moiety that improves the solubility, bioavailability, and/or any other desired feature of the formed conjugate.

The conjugates described hereinabove may be prepared, administered or otherwise utilized in any of the aspects of embodiments of the invention, either as is, or as a pharmaceutically acceptable salt, enantiomers, diastereomers, solvates, hydrates or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the moieties and/or conjugates which are prepared with relatively nontoxic acids or bases, depending on the particular substituents found on the compounds described herein. When conjugates according to embodiments of the invention contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When conjugates according to embodiments of the invention contain relatively basic functionalities, acid addition salts can be obtained by contacting the neutral form of such conjugates with a sufficient amount of the desired acid, either neat or in a suitable inert solvent. Examples of pharmaceutically acceptable acid addition salts include, but are not limited to, those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al., "Pharmaceutical Salts", Journal of Pharmaceutical Science, 1977, 66, 1-19). Certain specific conjugates of the present invention contain both basic and acidic functionalities that allow the conjugates to be converted into either base or acid addition salts.

The neutral forms of the conjugates are preferably regenerated by contacting the salt with a base or acid and isolating the parent conjugate in a conventional manner. The parent form of the conjugate differs from the various salt forms in certain physical properties, such as solubility in polar solvents, but otherwise the salts are equivalent to the parent form of the conjugate for the purposes of the present invention.

In an example, a pharmaceutically acceptable salt of alendronate is utilized. An exemplary such salt is sodium alendronate. An alendronate-containing conjugate can therefore comprise a sodium salt of alendronate.

In another example, a pharmaceutically acceptable salt of aspartate is utilized.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The conjugates described herein may possess asymmetric carbon atoms (optical centers) or double bonds; the racemates, diastereomers, geometric isomers and individual isomers are encompassed within the scope of embodiments of the invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The conjugates described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Certain conjugates of the present invention may exist in multiple crystalline or amorphous forms. In general, all physical forms are equivalent for the uses contemplated by the present invention and are intended to be within the scope of the present invention.

As discussed hereinabove, the conjugates described herein (also referred to herein throughout as polymeric conjugates) comprise a bone targeting moiety being either alendronate or an oligopeptide of aspartate, which enables the targeting of the conjugate to bone and bone related structures. Due to the anti-angiogenesis/anti-proliferative activity exhibited by the moieties attached to the polymer and the formed conjugate as a whole, each of the conjugates described herein can be beneficially used for treating bone and bone related disease and disorders.

Hence, according to another aspect of some embodiments of the present invention there are provided methods of treating a bone related disease or disorder in a subject in need thereof. These methods are effected by administering to the subject a therapeutically effective amount of any of the conjugates described herein.

Accordingly, according to another aspect of some embodiments of the present invention there are provided uses of any of the conjugates described herein as a medicament. In some embodiments, the medicament is for treating a bone-related disease or disorder.

According to another aspect of some embodiments of the present invention, the conjugates described herein are identified for use in the treatment of a bone related disease or disorder.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The phrase "a bone related disease or disorder" describes a disease or disorder wherein bone formation, deposition, or resorption is abnormal, especially those characterized by excessive angiogenesis. The phrase "bone related disease or disorder" also encompasses disease and disorders occurring in bodily sites other than bone which evolved from a bone related disease or disorder such as, for example, metastasis of bone cancer in another organ and diseases and disorders which evolved in other bodily sites and affect bone tissues.

Bone-related diseases disorders include, but are not limited to, bone cancer and bone cancer metastases, osteopenia due to bone metastases, periodontal disease, periarticular erosions in rheumatoid arthritis, Paget's disease, malignant hypercalcemia, osteolytic lesions produced by bone metastasis, bone abnormalities caused by cancer therapeutics and hyperostosis.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. When the treatable disease is bone cancer, this term encompasses any inhibition of tumor growth or metastasis, or any attempt to inhibit, slow or abrogate tumor growth or metastasis.

It is noted herein that by targeting an anti-angiogenesis agent via the methodologies described herein, the toxicity of the anti-angiogenesis agent is substantially reduced, due to the conjugate selectivity towards bone tissues. Consequently, besides the use of the conjugates described herein in a clinically evident disease, optionally in combination with other drugs, these conjugates may potentially be used as a long term-prophylactic for individuals who are at risk for relapse due to residual dormant cancers. The use of non-toxic targeted conjugates for the treatment of asymptomatic individuals who are at risk for relapse of osteosarcoma, as an example, may lead to a major paradigm shift in cancer treatment from current methods where treatment is generally not initiated until a bone related disease such as osteosarcoma becomes clinically evident.

The term "subject" (alternatively referred to herein as "patient") as used herein refers to an animal, preferably a mammal, most preferably a human, who has been the object of treatment, observation or experiment.

As demonstrated in the Examples section that follows and discussed elaborately hereinabove, it has been shown that the conjugates described herein inhibit angiogenesis as well as cell proliferation and therefore can be utilized for the treatment of bone related disease and disorders characterized by pathologically excessive angiogenesis wherein the inhibition of angiogenesis and/or cell proliferation is beneficial.

Hence, in some embodiments the bone related disease or disorder is associated with angiogenesis.

Tumor growth and metastasis are particularly dependent on the degree of angiogenesis. Tumor angiogenesis is the proliferation of a network of blood vessels that penetrate into cancerous tumors in order to supply nutrients and oxygen and remove waste products, thus leading to tumor growth. Tumor angiogenesis involves hormonal stimulation and activation of oncogenes, expression of angiogenic growth factors, extravasation of plasma protein, deposition of a provisional extracellular matrix (ECM), degradation of ECM, and migration, proliferation and elongation of endothelial capillaries. Inhibition of further vascular expansion has therefore been the focus of active research for cancer therapy.

Hence, in some embodiments, the bone related disease or disorder is selected from the group consisting of bone cancer metastases and bone cancer.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not-malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

The term "bone cancer" describes tumors that arise from the tissues of the bone. The term "bone cancer", as used herein, further encompasses tumors in tissues located in proximity to bone structures and associated with bone such as cartilage, bone cavity and bone marrow. The term "bone cancer" further encompasses cancer which evolved from bone cells (i.e. primary tumor), as well as cancer cells which have "breaken away", "leaked", or "spilled" from a primary tumor located in bone, entered the lymphatic and/or blood vessels, circulated through the lymphatic system and/or bloodstream, settled down and proliferated within normal tissues elsewhere in the body thereby creating a secondary tumor. For example, metastases originating from osteosarcoma can be frequently found in the lungs and in other organs. These lesions produce an osteoid and therefore can be targeted with bone targeting moieties, as described herein.

Bone cancer is found most often in the bones of the arms and legs, but it can occur in any bone.

Bone cancers are also known as sarcomas. There are several types of sarcomas of bone, depending upon the kind of bone tissue where the tumor developed. Exemplary types of bone cancers that are treatable according to embodiments of the invention include, but are not limited to, osteosarcoma, Ewing's sarcoma, chondrosarcoma, fibrosarcoma, malignant giant cell tumor, and chordoma.

Osteosarcoma is the most common type of primary bone cancer and classified as a malignant mesenchymal neoplasm in which the tumor directly produces defective osteoid (immature bone). It is a highly vascular and extremely destructive malignancy that most commonly arises in the metaphyseal ends of long bones. Several strategies were proposed, such as immune-based therapy, tumor-suppressor or suicide gene therapy, or anticancer drugs that are not commonly used in osteosarcoma [Quan et al. *Cancer Metastasis Rev* 2006; 10: 707-713]. However, still one-third of patients die from this devastating cancer, and for those with unresectable disease there are no curative systemic therapies.

The term "bone metastases" describes cancer evolving form a primary tumor located in bodily site other than bone but metastasizing to the bone (i.e. a secondary tumor). Cancers that commonly metastasize, or spread, to the bones include breast cancer, lung cancer, thyroid cancer, prostate cancer, some brain cancers and cancers of the kidney.

For example, prostate cancer is the most common cancer of males in industrialized countries and the second leading cause of male cancer mortality. Prostate cancer predominantly metastasizes to bone, but other organ sites are affected including the lung, liver, and adrenal gland. Bone metastases incidence in patients with advanced metastatic disease is approximately 70%. Bone metastases are associated with considerable skeletal morbidity, including severe bone pain, pathologic fracture, spinal cord or nerve root compressions, and hypercalcemia of malignancy.

As discussed hereinabove, the conjugates described herein may be further utilized for monitoring bone related disease or disorders. In such a case the conjugate further comprises a labeling agent, as defined herein, for easy detection of the conjugate in the body of the patient, using well known imaging techniques. For example, in the case of the bone related disease or disorder being bone cancer the detection of the conjugate, as assessed by the level of labeling agent signal, can serve to detect bone cancer metastases in bodily sites other than bone.

Hence, according to another aspect of some embodiments of the invention, there are provided methods of monitoring a bone related disease or disorder in a subject. The method according to these embodiments of the invention is effected by administering to the subject any of the conjugates described herein, having a labeling agent attached to the polymer, as described herein, and employing an imaging technique for monitoring a distribution of the conjugate within the body or a portion thereof.

Accordingly, according to another aspect of some embodiments of the present invention there are provided uses of any of the conjugates described herein, having a labeling agent as described herein, as diagnostic agents and/or in the manufacture of a diagnostic agent for monitoring a bone related disease or disorder.

According to another aspect of some embodiments of the present invention, each of the conjugates described herein, which comprises a labeling agent, is identified for use as a diagnostic agent, for monitoring a bone related disease or disorder.

Suitable imaging techniques include, but are not limited to, positron emission tomography (PET), gamma-scintigraphy, magnetic resonance imaging (MRI), functional magnetic resonance imaging (FMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

According to another aspect of the present invention there is provided a pharmaceutical composition comprising, as an active ingredient, any of the conjugates described herein and a pharmaceutically acceptable carrier Accordingly, in any of the methods and uses described herein, any of the conjugates described herein can be provided to an individual either per se, or as part of a pharmaceutical composition where it is mixed with a pharmaceutically acceptable carrier.

As used herein a "pharmaceutical composition" refers to a preparation of one or more of the conjugates described herein (as active ingredient), or physiologically acceptable salts or prodrugs thereof, with other chemical components including but not limited to, physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to some embodiments, the pharmaceutical composition described herein is packaged in a packaging material and identified in print, in or on the packaging material, for use in the treatment of a bone related disease or disorder.

According to other embodiment of the present invention, the pharmaceutical composition is packaged in a packaging material and identified in print, in or on the packaging material, for use in monitoring a bone related disease or disorder.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In any of the methods, uses and compositions described herein, the conjugates described herein can be utilized in combination with additional therapeutically active agents. Such additional agents include, as non-limiting examples, chemotherapeutic agents, anti-angiogensis agents, hormones, growth factors, antibiotics, anti-microbial agents, anti-depressants, immunostimulants, and any other agent that may enhance the therapeutic effect of the conjugate and/or the well-being of the treated subject.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise; For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Materials and Methods

Materials:

All reactions requiring anhydrous conditions were performed under argon or nitrogen atmosphere.

Chemicals and solvents were either A.R. Grade or purified by standard techniques.

Thin layer chromatography (TLC): silica gel plates Merck 60 $F_{254}$; compounds were visualized by irradiation with UV light and/or by treatment with a solution of phosphomolybdic acid (20% wt. in ethanol), followed by heating.

Flash chromatography (FC): silica gel Merck 60 (particle size 0.040-0.063 mm), eluent given in parentheses.

Cathepsin K inhibitor III was purchased from Calbiochem, Germany.

Phalloidin-TRITC conjugate, Propidium iodide and hydroxyapatite (HA) were purchased from Sigma-Aldrich, Israel.

Alendronate was purchased from Alcon Biosciences, India.

Ultra pure double distilled water (DDW) was purchased from Biological Industries, Israel.

Antifade® mounting media was from Biomeda.

Alexa® Fluor 594 human transferrin was from Molecular Probes™

Peroxidase Block was purchased from Merck, Germany. Primary rat anti-murine CD34 antibody (MEC 14.7) was purchased from Abcam, (Cambridge, Mass.). Rabbit anti-rat antibody, anti-rabbit horseradish peroxidase-conjugated antibody (ABC detection kit) and ImmPACT™ DAB diluent kit were purchased from Vector Laboratories, CA, USA.

Boyden chambers 8 μm were from Transwell-Costar Corporation.

Hema 3 Stain System was from Fisher Diagnostics.

EGM-2 medium was from Cambrex, USA and endothelial cells growth supplement (ECGS) from Zotal, Israel.

All other chemical reagents, including salts and solvents, were purchased from Sigma-Aldrich.

All animal procedures were performed in compliance with Tel Aviv University, Sackler School of Medicine guidelines and protocols approved by the Institutional Animal Care and Use Committee. Mice's body weight and tumor size were measured three times a week.

Generation of mCherry-Infected MG-63-Ras Human Osteosarcoma Cell Line:

mCherry was subcloned from pART7-mCherry, into pQCXIP (Clontech). Human embryonic kidney 293T (HEK 293T) cells were co-transfected with pQC-mCherry and the compatible packaging plasmids (pMD.G.VSVG and pGag-pol.gpt). Forty eight hours following transfection, the pQC-mCherry retroviral particles containing supernatant was collected. MG-63-Ras human osteosarcoma cells were infected with the retroviral particles media, and 48 hours following the infection, mCherry positive cells were selected by puromycin resistance.

Cell Culture:

Saos-2 human osteosarcoma cells were obtained from the American Type Culture Collection (ATCC). Cells were cultured in Dulbecco's modified Eagle's medium (DMEM) supplemented with 10% fetal bovine serum (FBS), 100 μg/ml Penicillin, 100 U/ml Streptomycin, 12.5 U/ml Nystatin and 2 mM L-glutamin (Biological Industries, Israel). Cells were grown at 37° C. in 5% $CO_2$. Isolation of primary human umbilical vein endothelial cells (HUVEC) was obtained as described previously [Larrivee et al. *Methods Mol Biol* 2005; 290: 315-329]. Cells were cultured in Endothelial Cell Medium-2 (EGM-2 medium; Cambrex, USA) and grown at 37° C. in 5% $CO_2$.

Cell Proliferation Assay:

HUVEC were plated at 10,000 cells/well onto 24-well culture plates in EBM-2 supplemented with 5% FBS and incubated for 24 hours (37° C.; 5% $CO_2$). Medium was replaced with 2.5% endothelial cell basal medium-2 (EBM-2) supplemented with 1% Endothelial cell growth supplement (ECGS). Human osteosarcoma Saos-2 or MG-63-Ras cells were plated at 2500 cells/well in DMEM supplemented with 5 FBS and incubated for 24 hours (37° C.; 5% $CO_2$). The medium was then replaced with DMEM supplemented with 10% FBS. Cells were exposed to ALN, TNP-470, and HPMA copolymer-ALN-TNP-470 conjugate or with equivalent concentrations of combinations of free ALN and TNP-470 at serial dilutions. HUVEC were also incubated with or without 1 μM of cathepsin-K inhibitor III. Control cells were grown in the presence or absence of growth factors. HUVEC or Saos-2 viable cells were counted by a Z1 Coulter® Particle Counter (Beckman Coulter™) or by XTT reagent respectively after 72 hours of incubation.

Isobolograms of ALN and TNP-470 Drug Combination Treatments:

$IC_{50}$ represents the concentration of a drug that is required for 50% inhibition in vitro. The $IC_{30, 50, 70}$ values of treatment with ALN, TNP-470 and their respective combinations from HUVEC proliferation assay were collected. $IC_{30, 50, 70}$ values of TNP-470 and ALN were marked on X, Y axis respectively and a line which represents additive effect was drawn between each inhibitory concentration (IC). The combination index (CI) of each treatment was calculated according to the classic isobologram equation $CI=[(D)_1/(Dx)_1]+[(D)_2/(Dx)_2]$ as previously described [Chou T. C. *Pharmacol Rev* 2006; 58:621-681]. Area on the right side of each IC additive line represents antagonist effect while the left side represents synergic effect.

Characterization of HPMA-ALN-TNP-470 Conjugate:

(a) Determination of ALN Content:

The formation of chromophoric complex between ALN and $Fe^{3+}$ ions in perchloric acid solution was used to spectrophotometrically determine the ALN content by spectrophotometry. Briefly, 0.1 ml conjugate (concentration 2-10 mgram/ml) was mixed with 0.1 ml 4 mM $FeCl_3$ and 0.8 ml 0.2 M $HClO_4$ and absorbance at 300 nm was measured against blank. The calibration curve was prepared by using an ALN solution at a concentration range of 0-3 mM.

(b) Estimation of TNP-470 Content:

The content of TNP-470 was estimated from the content of $NH_2$ groups in the HPMA copolymer-ALN-$NH_2$ precursor (shown in FIG. 1, middle structure), assuming that the TNP-470 binding was quantitative. The content of $NH_2$ groups was determined by ninhydrin method using an amine containing monomer (N-(3-aminopropyl)methacrylamide) as the calibration sample (modified from Duncan, at el. *J Control Release* 2001; 74: 135-146).

(c) Determination of FITC Content:

The content of FITC was measured spectrophotometricaly using $\epsilon$ 80000 M-1 cm-1 in 0.1 M borate buffer.

(d) Determination of HPMA Copolymer-ALN-TNP-470 Conjugate Molecular Weight and Polydispersity Index (PDI):

Determination of polymer-drug molecular weight profile by size exclusion chromatography was done using AKTA/

FPLC system (Pharmacia/GE Healthcare), Superose 12 HR10/30 column, buffer 0.1 M acetate+30% acetonitrile, pH 5.5, flow rate 0.4 ml/minute; UV and RI detection. Weight average molar mass ($M_w$) was evaluated from the SEC profiles and the PDI was calculated according to the formula $M_w/M_n$. The column was calibrated using polyHPMA fractions of narrow polydispersity (e) Quantitative Evaluation of HPMA Copolymer-ALN-TNP-470 Conjugate Size Distribution:

The mean hydrodynamic diameter of the conjugate was evaluated using a real time particle analyzer (NANOSIGHT LM20™) containing a solid-state, single mode laser diode (<20 mW, 655 nm) configured to launch a finely focused beam through a 500 μl sample chamber. HPMA copolymer-ALN-TNP-470 conjugate was dissolved in phosphate buffered saline (PBS) to final concentrations of 0.5, 1 and 2 mg/ml. The samples were then injected into the chamber by syringe and allowed to equilibrate to unit temperature (23° C.) for 30 seconds. The particles dynamics were visualized at 30 frames per second (fps) for 60 seconds at 640×480 resolution by a coupled charge device (CCD) camera. The paths the particles take under Brownian motion over time were analyzed using Nanoparticle Tracking Analysis (NTA) software. The diffusion coefficient and hence sphere equivalent hydrodynamic radius of each particle was separately determined and the particle size distribution profiles were generated. Each sample was measured three times in triplicates, and the results represent the mean diameter.

Hydroxyapatite Binding Assay:

In order to assess the ability of HPMA copolymer-ALN-TNP-470 conjugate to bind to bone mineral, its binding potency to hydroxyapatite (HA) was evaluated. HPMA copolymer-ALN-TNP-470 conjugate was dissolved in phosphate buffered saline (PBS), pH 7.4 (1 mg/ml). The conjugate solution (500 μl) was incubated with hydroxyapatite powder (15 mg), in 500 μl PBS, pH 7.4. HPMA copolymer-Gly-Phe-Leu-Gly was used as control. Incubated samples were centrifuged at 6000 RPM for 3 minutes and a sample from the upper layer (100 μl) was collected at selected time points. FPLC analysis using HighTrap desalting column (Amersham®) was used for detection of unbound conjugate in the samples (FPLC conditions: AKTA™ Purifier®, mobile phase 100% DDW, 2 ml/minute, 215 nm). Hydroxyapatite binding kinetic analysis of the conjugate was performed using the Unicorn® AKTA™ software. Areas under the curve (AUC) were calculated from chromatographs at each time point. AUC of each hydroxyapatite incubated conjugate chromatogram was normalized to percent AUC of conjugate sample in the absence of hydroxyapatite used as control.

Intracellular Trafficking of a HPMA Copolymer-ALN-TNP-470 Conjugate:

For all experiments, human umbilical vain endothelial cells (HUVEC) and Saos-2 human osteosarcoma cells were seeded on sterile 13 mm cover glasses in 35 mm culture dishes 24 hours before incubation with fluorescein isothiocyanate (FITC) labeled HPMA copolymer-ALN-TNP-470 conjugate and left to reach 90% confluence. HUVEC and Saos-2 cells were then incubated with 10 μM FITC-HPMA copolymer ALN-TNP-470 conjugate for 12 hours. Following incubation, cells were washed several times with cold phosphate buffered saline (PBS), fixed with 3.5% paraformaldehyde for 15 minutes at room temperature (RT) and washed with PBS again. For counter staining, cells were permeabilized with 0.1% Triton-X100 for 3 minutes and rinsed with PBS again. For confocal imaging of FITC-labeled HPMA copolymer ALN-TNP-470 conjugate cellular uptake by HUVEC, nuclei were labeled using propidium iodide (10 μg/ml) and cover glasses were mounted by Antifade® mounting media. Alternatively, actin filaments were labeled using phalloidin-TRITC conjugate (50 μg/ml, 40 minutes at RT) and cover glasses were mounted by Vectashild®DAPI containing medium. For conjugate endosomal pathway internalization analysis, HUVEC and Saos-2 cells were incubated with 10 μM FITC-HPMA copolymer ALN-TNP-470 conjugate for 6 hours. Following incubation cells were washed several times with cold PBS, starved for 45 minutes in serum free medium at 37° C. and incubated with 40 μg/ml Alexa® Fluor 594 human transferrin for 1 hour at 37° C. Cells were then fixed and mounted as described before. All slides were kept at 4° C. in dark until confocal microscopy analysis was preformed.

Confocal Microscopy:

Cellular uptake, internalization and colocalization of FITC-labeled HPMA copolymer ALN-TNP-470-FITC conjugate were monitored utilizing a Zeiss Meta LSM 510 and a Leica TCS SP5 confocal imaging systems with 60× oil objectives. All images were taken using a multi-track channel acquisition to prevent emission cross-talk between fluorescence dyes. Single XY, XZ plane-images were acquired in 1024×1024 resolution. Images from Z stack acquisition were processed as separate channels using Huygens® deconvolution software and overlaid as a single image.

Human Umbilical Vain Endothelial Cells (HUVEC) Migration Assay:

Cell migration assays were performed using modified 8 μm Boyden chambers coated with 10 μg/ml fibronectin. HUVEC ($15 \times 10^4$ cells/100 μl) were challenged with HPMA copolymer ALN-TNP-470 conjugate or with combinations of free ALN+free TNP-470 at equivalent concentrations and were added to the upper chamber of the transwell for 4 hours incubation. Following incubation, cells were allowed to migrate to the underside of the chamber for 4 hours in the presence or absence of Vascular endothelial growth factor (VEGF) (20 ng/ml) in the lower chamber. Cells were then fixed with ice-cold menthol and stained using Hema 3 Stain System. The stained migrated cells were imaged using Nikon TE2000E inverted microscope integrated with Nikon DS5 cooled CCD camera by 10× objective, brightfield illumination. Migrated cells from the captured images per membrane were counted using NIH image software. Migration was normalized to percent migration, with 100% representing VEGF dependent migration of cells which were not incubated with free or HPMA-conjugated ALN and TNP-470.

Capillary-Like Tube Formation Assay:

The surface of 24-well plates was coated with Matrigel® basement membrane (50 μl/well; 10 mg/ml) on ice and was allowed to polymerize at 37° C. for 30 minutes. HUVEC ($3 \times 10^4$ cells) were challenged with HPMA copolymer ALN-TNP-470 conjugate or with combinations of free ALN+free TNP-470 at equivalent concentrations and were seeded on coated plates in the presence of complete EGM-2 medium. After 8 hours of incubation (37° C.; 5% $CO_2$), wells were imaged using Nikon TE2000E inverted microscope integrated with Nikon DS5 cooled CCD camera by 4× objective, brightfield illumination. Images were analyzed for total tube area using Nikon NIS elements image software.

Miles Vascular Permeability Assay:

Balb/c male mice were injected subcutaneously (s.c.) with TNP-470, HPMA copolymer-ALN-TNP-470 conjugate (30 mg/kg TNP-470 equivalents) or saline (n=5 mice/group). Three days later, a modified Miles assay was performed as previously described [Claffey et al. 1996, *Cancer Res* 56: 172-181; Miles & Miles 1952, *J Physiol* 118:228-257]. Briefly, Evans blue dye (100 μl of a 1% solution in 0.9% NaCl) was injected into the retro-orbital plexus of the mice.

Ten minutes later, 50 µl of human VEGF$_{165}$ (1 ng/µl) or PBS were injected intradermally into the pre-shaved back skin. Twenty minutes later, the animals were killed, and an area of skin that included the entire injection site was removed. Evans blue dye was extracted from the skin by incubation with formamide for 5 days at room temperature, and the absorbance of the extracted dye was measured at 620 nm. Data is expressed as mean±standard error of the mean (s.e.m.).

Evaluation of Antitumor Activity of HPMA Copolymer-ALN-TNP-470 Conjugate:

SCID male were inoculated s.c. with 5×10$^5$ mCherry-labeled MG-63-Ras human osteosarcoma. Mice bearing 70 mm$^3$ tumors were injected s.c. with combination of free ALN and TNP-470 (1:1, 30 mg/kg), FITC-labeled HPMA copolymer-ALN-TNP-470 conjugate (30 mg/kg q.o.d.×3 times TNP-470-equivalent dose) or saline (n=5 mice/group). Therapy was initiated at a relatively early state (70 mm$^3$) in order to imitate a metastatic scenario as well as an early primary osteosarcoma. Tumor progression was monitored by caliper measurement (width×length$^2$×0.52) and by CRI™ Maestro non-invasive intravital imaging system. At termination, tumors were dissected, weighed and analyzed. Data is expressed as mean±standard error of the mean (s.e.m.).

Intravital Non-Invasive Imaging of mCherry-Labeled MG-63-Ras Tumor-Bearing Mice and FITC-Labeled HPMA Copolymer-ALN-TNP-470 Conjugate Biodistribution in Mice:

CRI Maestro™ non-invasive fluorescence imaging system was used to follow tumor progression of mice bearing mCherry-labeled MG-63-Ras human osteosarcoma tumors and for biodistribution studies of FITC-labeled HPMA copolymer-ALN-TNP-470 conjugate. Mice were maintained on a non-fluorescent diet (Harlan) for the whole period of the experiment. Mice were anesthetized using ketamine (100 mg/kg) and xylazine (12 mg/kg), treated with a depilatory cream (Veet®) and placed inside the imaging system. Alternatively, selected organs from mice were dissected and placed inside the imaging system. Multispectral image-cubes were acquired through 550-800 nm spectral range in 10 nm steps using excitation (575-605 nm) and emission (645 nm long-pass) filter set. Mice autofluorescence and undesired background signals were eliminated by spectral analysis and linear unmixing algorithm. Additionally, dissected tumors were fixed in 4% PFA and imaged as whole-mount by confocal microscopy as described earlier in order to assess the conjugate accumulation in the tumor site.

Immunohistochemistry:

Immunohistochemistry of tumor nodules was performed using 5 µm thick formalin-fixed, paraffin-embedded tissue sections. Paraffin sections were de-paraffinized, rehydrated, and stained by hematoxylin and eosin (H & E). For CD34 staining (an endothelial cell marker), slides were deparaffinized and pre-treated with 10 mM citrate, pH 6.0 for 50 min in a steam pressure cooker (Decloaking Chamber, BioCare Medical, Walnut Creek, Calif.). All further steps were performed at room temperature in a hydrated chamber. Slides were covered with Peroxidase Block (Merck, Germany) for 5 minutes to quench endogenous peroxidase activity, followed by incubation with 10% of rabbit serum in 50 mM Tris-HCl, pH 7.4, for 30 min to block non-specific binding sites. Primary rat anti-murine CD34 antibody (MEC 14.7 1:50 dilution; Abcam, Cambridge, Mass.) was applied in 1% rabbit serum in Tris-HCl, pH 7.4 at room temperature for 1 hour. Slides were washed in 50 mM TrisHCl, pH 7.4 and rabbit anti-rat antibody (1:750 dilution; Vector Laboratories, CA, USA) was applied for 30 minutes, followed by anti-rabbit horseradish peroxidase-conjugated antibody (ABC detection kit, Vector Laboratories, CA, USA). Following further washing, immunoperoxidase staining was developed using a ImmPACT™ DAB diluent kit (Vector Laboratories, CA, USA) per the manufacturer instructions and counterstained with methyl green. Microvessel density (MVD) was calculated as previously described [Weidner et al. 1991, *N Engl J Med* 324:1-8].

Statistical Methods:

In vitro data from proliferation assays on HUVEC, MG-63-Ras and Saso-2 cells, HUVEC's migration and capillary-like tube formation expressed as mean±standard deviation (s.d.). In vivo data of Miles assay and evaluation of antitumor activity of HPMA copolymer-ALN-TNP-470 conjugate was expressed as mean±standard error of the mean (s.e.m.). Statistical significance was determined using an unpaired t-test. $P<0.05$ was considered statistically significant. All statistical tests were two-sided.

Example 1

Synthesis of HPMA Copolymer-ALN-TNP-470 Conjugate

The general synthesis of a HPMA-ALN-TNP-470 conjugate according to some embodiments of the present invention is depicted in FIG. 1.

HPMA-Gly-Gly-Pro-Nle-ALN-TNP-470 (SEQ ID NO: 12) conjugate was prepared in a two-step synthesis. First, an intermediate was synthesized by copolymerization of HPMA, ALN-methacrylamide monomer (MA-Gly-Gly-Pro-Nle-ALN; (SEQ ID NO: 8), and amino group-containing methacrylamide monomer (MA-Gly-Gly-Pro-Nle-ethylenediamine; SEQ ID NO: 13). Optionally, for the evaluation of intracellular trafficking, a polymerizable derivative of fluorescein isothiocyanate (FITC), N-methacryloylaminopropyl fluorescein thiourea (MA-FITC), was added to the monomer mixture. Next, TNP-470 was linked to free amino groups by nucleophilic substitution of the terminal chlorine of TNP-470.

Synthesis of ALN-containing monomer (MA-Gly-Gly-Pro-Nle-ALN; SEQ ID NO: 8): MA-Gly-Gly-Pro-Nle (SEQ ID NO: 7) was synthesized by solid phase peptide synthesis (SPPS) and manual Fmoc/tBu strategy using 2 grams of 2-chlorotrityl chloride beads with 80% loading, yielding the desired monomer (0.88 grams, 95% purity). MA-Gly-Gly-Pro-Nle-OH (SEQ ID NO: 14; 100 mg, 0.24 mmol) and 2-mercaptothiazoline (TT, 33 mg, 0.28 mmol) were dissolved in a mixture of 2 ml 1,4-dioxane and 1 ml tetrahydrofuran (THF), and cooled to 4° C. N,N'-Dicyclohexylcarbodiimide (DCC; 60 mg, 0.29 mmol) in 1 ml of 1,4-dioxane was added dropwise and the reaction mixture stirred overnight at 4° C. Dicyclohexylurea (DCU) was thereafter removed by filtration and the filtrate was added to ALN aqueous solution (70 mg, 4 ml; pH was adjusted to about 7.4 by NaHCO$_3$ solution). The reaction mixture was stirred overnight at room temperature. The solvent was then removed on a rotary evaporator and the residue was re-dissolved in water and extracted with ethyl acetate 3 times to remove TT. The product was purified by preparative high performance liquid chromatography (HPLC), yielding 83 mg of the desired ALN monomer.

The MALDI-TOF spectrum negative ion: m/z=640 (M−H$^+$), 662 (M-mono-Na salt−H$^+$); positive ion: m/z=642 (M+H$^+$), 664 (M-mono-Na salt+H$^+$), 686 (M-mono-Na salt+Na$^+$).

Synthesis of amine containing monomer (MA-Gly-Gly-Pro-Nle-NH(CH$_2$)$_2$NH$_2$; SEQ ID NO: 13): MA-Gly-Gly- Pro-Nle-ethylenediamine (SEQ ID NO:13) was synthesized by SPPS using 1.5 gram of 2-chlorotrityl chloride beads. Six-time excess of ethylenediamine in anhydrous tetrahydrofuran (THF) was applied, followed by Fmoc-amino acids, and capping with MA-Gly-Gly-OH (SEQ ID NO:15). The final peptide was cleaved by 5% trifluoroacetic acid (TFA) in dichloromethane (DCM), yielding 0.85 gram of the desired compound, in 89% purity, as determined by HPLC (buffer A: $H_2O$, 0.1% TFA; buffer B: acetonitrile, 0.1% TFA; gradient method: buffer B 2-60%/30 minutes; 1 ml/minute; single peak, elution time 8.27 minutes).

The MALDI-TOF spectrum (Fmoc derivative) positive ion: m/z=697 (M+Na$^+$), 713 (M+K$^+$).

Synthesis of fluorescein thiourea (FITC) containing monomer N-methacryloylaminopropyl-FITC (MA-FITC): FITC (1 gram, 2.57 mmol) and N-(3-aminopropyl)methacrylamide hydrochloride (0.92 gram, 5.14 mmol) were dissolved in 5 ml dimethylformamide (DMF) and the solution was cooled to 4° C. diisopropylethylamine (DIPEA) (1.79 ml, 10.3 mmol) in 2 ml of DMF was thereafter added dropwise and the reaction mixture was stirred at 4° C. for 2 days. The reaction mixture was then poured into 100 ml water (pH of about 4-5) and the pH was adjusted to about 4 by 6 N HCl. The precipitate was filtered off, washed with water, and vacuum dried over $P_2O_5$.

Synthesis of Polymer Precursor Containing ALN, Free $NH_2$, and (Optionally) FITC Groups (HPMA Copolymer-ALN-NH$_2$)

Two synthesis approaches were attempted:

In a first synthetic approach, MA-Gly-Gly-Pro-Nle-ALN (SEQ ID NO: 8), MA-Gly-Gly-Pro-Nle-NH-ethylene-NH$_2$ (SEQ ID NO: 13) (for conjugating TNP-470), HPMA and MA-FITC (optional) are dissolved in water in the presence of 4,4'-azobis(4-cyanovaleric acid) (VA-501) as a co-polymerization initiator. The solution is bubbled with nitrogen for 10 minutes, the ampoule is sealed, and copolymerization is performed at 60° C.

The relative amounts of the various monomeric units can be varied as desired, so as to determine the load of the alendronate, the TNP-470 and the PITC (if present) in the formed polymer. The reaction conditions can further be manipulated, so as to determine the degree of polymerization or to incorporate other moieties such as tyrosine groups in order to radiolabel the conjugate In one example, MA-Gly-Gly-Pro-Nle-ALN (SEQ ID NO: 8) (73 mg), MA-Gly-Gly-Pro-Nle-NH-ethylene-NH$_2$ (SEQ ID NO: 13) (55 mg), HPMA (200 mg), MA-FITC (4 mg, if present) and 4,4'-azobis(4-cyanovaleric acid) (VA-501, 3 mg) as the initiator were dissolved in 2 ml of water. The solution was bubbled with nitrogen for 10 minutes, the ampoule sealed, and the mixture polymerized at 60° C. for 24 hours.

In another example, MA-Gly-Gly-Pro-Nle-ALN (SEQ ID NO: 8) (73 mg), MA-Gly-Gly-Pro-Nle-NH-ethylene-NH$_2$ (SEQ ID NO: 13) (55 mg) and HPMA (200 mg) were dissolved in 2 ml water in the presence of 4,4'-azobis(4-cyanovaleric acid) (VA-501, 3 mg). The solution was bubbled with nitrogen for 10 minutes, the ampoule sealed, and the mixture polymerized at 60° C. for 24 hours.

In a second synthetic approach, a reversible addition-fragmentation chain transfer (RAFT) polymerization technique was used.

MA-Gly-Gly-Pro-Nle-ALN (SEQ ID NO: 8), MA-Gly-Gly-Pro-Nle-NH(CH$_2$)$_2$NH$_2$ (SEQ ID NO: 13), HPMA, and MA-FITC (optional) are dissolved in water in the presence of 2,2'-Azobis[2-(2-imidazolin-2-yl)propane]dihydrochloride (VA-044) as an initiator and S,S'-bis(α,α'-dimethyl-α"-acetic acid)trithiocarbonate as a chain transfer agent (TTC). The solution is bubbled with nitrogen for 30 minutes, sealed in ampoule, and co-polymerization is performed at 30° C.

In an example, MA-Gly-Gly-Pro-Nle-ALN (SEQ ID NO: 8) (293 mg), MA-Gly-Gly-Pro-Nle-NH(CH$_2$)$_2$NH$_2$ (SEQ ID NO: 13) (215 mg), HPMA (948 mg), MA-FITC (4 mg if present), 2,2'-Azobis[2-(2-imidazolin-2-yl)propane]dihydrochloride (VA-044 1.6 mg) as initiator and S,S'-bis(α,α'-dimethyl-α"-acetic acid)trithiocarbonate as chain transfer agent (TTC 4.2 mg) were dissolved in 7.5 ml of water. The solution was bubbled with nitrogen for 30 minutes, sealed in ampoule, and the mixture polymerized at 30° C. for 48 hours.

Both polymers were purified by dissolving in water and precipitating into an excess of acetone (3 times); following each precipitation, the precipitate was washed with acetone. Finally, the polymers were dissolved in 15 ml of water; pH adjusted to 12 with 1 N NaOH, and dialyzed against DI water for 24 hours at 4° C. (MWCO 12-14 kDa) to remove excess ALN monomer. The sample was freeze-dried after dialysis.

The content of ALN, FITC and amine in the HPMA conjugate was estimated as described in the methods section hereinabove. In an exemplary conjugate synthesized via the first synthesis approach, as described hereinabove, the content of ALN was determined to be 0.42 mmol/gram (7.0 mol %), the content of FITC was determined to be 0.04 mmol/gram (0.6 mol %), and the content of amine (for use in the estimation of % of bound TNP-470) was determined to be 0.24 mmol/gram (4.3 mol %). In another exemplary conjugate synthesized via the first synthesis approach but without FITC and while using a different concentration of alendronate-containing monomeric units, the content of ALN was determined to be 0.18 mmol/gram (3.2 mol %), and the content of amine was determined to be 0.36 mmol/gram (6.4 mol %).

In an exemplary conjugate synthesized via the second synthesis approach (RAFT), as detailed hereinabove, the content of ALN was determined to be 7.7 mol %, the content of FITC was determined to be 0.1 mol %, and the content of amine was determined to be 6.3 mol %.

It is therefore shown that in any of synthetic approaches described herein, the load of alendronate can be controlled as desired and further, a relatively high load can be obtained.

Synthesis of HPMA-ALN-TNP-470 conjugate: HPMA copolymer-ALN-NH$_2$ (150 mg) was dissolved in 6 ml of dimethylformamide (DMF; if necessary, a small amount of water was added to dissolve the polymer) and the solution was cooled to 4° C. Then, TNP-470 (150 mg) in 1 ml DMF was added. The reaction mixture was stirred at 4° C. in the dark for 12 hours. The conjugate was thereafter precipitated into acetone and purified by reprecipitation (3 times) from an aqueous solution into an excess of acetone. The precipitate was washed with acetone and the residue was dissolved in water and dialyzed for 1 day at 4° C. (MWCO 12-14 kDa) against DI water. The product was isolated by free-drying.

The final product was purified and characterized by reverse phase preparative HPLC. HPMA-ALN-TNP-470 conjugate eluted as a single peak with a retention time of 20 minutes as evaluated by size exclusion chromatography (SEC) (see, FIG. 3B).

Quantitative evaluation of HPMA-ALN-TNP-470 conjugate size distribution: The molecular weight and polydispersity of the two conjugates synthesized, namely, the conjugate polymerized by the classical polymerization method (polymerization I conjugate) and the conjugate polymerized by "living polymerization" RAFT (polymerization II conjugate), were estimated by SEC exhibiting an apparent $M_w$ of 80 kDa (FIGS. 3D and 3E respectively). Additionally, the hydrodynamic diameter size distribution of the HPMA copolymer- ALN-TNP-470 conjugates was determined using an optical analyzer. The conjugate polymerized by the classical polymerization method had a PDI of ~1.62 with a mean size distribution of 241 nm whereas the conjugate polymerized by "living polymerization" RAFT was well-dispersed exhibiting a considerably lower and narrower PDI of ~1.2 with a mean size distribution of 100 nm (FIG. 3F). The values of mean size distribution of the first conjugates, synthesized by the classical polymerization method, clearly indicate that associates formed under the experimental conditions used.

Example 2

Effect of Combination Treatment of ALN and TNP-470 on Proliferation of Endothelial Cells In Vitro Prior to conjugation of ALN and TNP-470 to HPMA copolymer backbone, the nature of the inhibitory effect of ALN and TNP-470 as a combined therapy on endothelial cells proliferation in vitro was evaluated. HUVEC were challenged with free or combined ALN and TNP-470. The results, presented in FIG. 2A show that combination treatments of ALN and TNP-470 decreased the IC's of the drugs as single treatments. ALN inhibited cell proliferation at inhibitory concentration $IC_{30, 50, 70}$ of 10, 50, 90 μM, respectively, and TNP-470 inhibited cell proliferation at $IC_{30, 50, 70}$ of 0.00025, 0.1, 1000 nM, respectively. Combination treatments I (serial concentrations of ALN and TNP-470 0.01 nM) and II (serial concentrations of TNP-470 and ALN 10 μM) inhibited HUVEC proliferation at $IC_{30, 50, 70}$ of 0.2, 10, 30 μM and 0.00001, 0.004, 40 nM, respectively.

Combination index (CI)-isobologram equation allowed quantitative determination of drug interactions, where CI<1, =1, or >1 indicated synergism, additive effect, or antagonism, respectively. Next, data from combination treatments were calculated according to CI equation and were used to generate isobolograms at $IC_{30, 50, 70}$ of HUVEC proliferation by ALN-TNP-470 combinations. As shown in FIG. 2B, combination treatment I had synergistic inhibitory effect on HUVEC at $IC_{30, 50, 70}$ with CI of 0.055, 0.3, and 0.89. Combination treatment II had synergistic effect at $IC_{50, 70}$ with CI of 0.23, 0.121 and additive effect at $IC_{30}$ with CI of 1.025.

Example 3

Binding of a HPMA-ALN-TNP-470 Conjugate to Bone Mineral Hydroxyapatite

One of the main characteristics of ALN besides its anti-angiogenic and antitumor activities is its pharmacokinetic profile which exhibits a strong affinity to bone mineral under physiological conditions. To determine if the activity of ALN is retained following polymer-conjugation, the affinity of the conjugate to bone mineral was evaluated by in vitro hydroxyapitate binding assay and FPLC analysis using Hitrap desalting column. As shown in FIG. 3B, unbound conjugates eluted as a single peak with a retention time of 1.9 minutes. AUC decreased in correlation with hydroxyapitate incubation time. Following 2 minutes of incubation with hydroxyapitate, 50% of the HPMA copolymer ALN-TNP-470 conjugate in the solution was bound to hydroxyapitate (see, FIG. 3C). This rapid binding rate to hydroxyapitate decreased after 10 minutes and finally reached a plateau after 175 minutes of incubation time with 92% of the HPMA copolymer ALN-TNP-470 conjugate bound to hydroxyapitate.

Example 4

Intracellular Trafficking of FITC-Labeled HPMA-ALN-TNP-470 Conjugate in Endothelial and Saos-2 Human Osteosarcoma Cells Following chemical characterization, the ability of FITC-labeled HPMA copolymer ALN-TNP-470 conjugate to internalize into endothelial and human osteosarcoma cells and the mechanism by which it internalizes was studied. HUVEC and Saos-2 osteosarcoma cells were incubated with the conjugate, fixed, permeabilzed and stained with the nuclei marker propidium iodide (PI). Confocal microscopy was performed by separately multi-channel tracking for PI (red) and FITC-labeled conjugate (green).

As shown in FIG. 4A, following 12 hours of incubation, the conjugate accumulated mostly in the cytoplasm of HUVEC and of Saos-2 cells as observed in the single plane image.

To evaluate the conjugate cellular localization and to eliminate optical artifacts, Z-stack of 5.7 μm with 28 slices and X, Z slice was captured and analyzed. As shown in FIGS. 4B and 4C, the conjugate was found to be located at the same focal plane as the nuclei, confirming its intracellular uptake.

Further examination of the conjugate cellular internalization was preformed using phalloidin (red) for actin filaments staining and DAPI for nuclei staining. As shown in FIGS. 4D-K, the staining revealed accumulation of the conjugate mainly around the nuclei in HUVEC (FIGS. 4D-G) and Saos-2 cells (FIGS. 4H-K).

The conjugate was capable of internalizing into HUVAC and Saos-2 cells as demonstrated by colocalization of 82% of the conjugate with transferrin in HUVEC cells (FIGS. 4L-O) and of 71% in Saos-2 cells (FIGS. 4P-S). These high percentages of colocalization suggest a lysosomotrophic pathway of cellular uptake via clathrin-coated vesicles.

Example 5

Effect of HPMA-ALN-TNP-470 Conjugate on Proliferation of Endothelial, Saos-2 and MG-63-Ras Human Osteosarcoma Cells To determine whether HPMA copolymer ALN-TNP-470 conjugate is active in vitro and that the bound drugs retained their antitumor and anti-angiogenic activity following polymer-conjugation, the inhibitory effect of the conjugate on HUVEC, Saos-2 and MG-63-Ras human osteosarcoma cell proliferation was examined.

The results, presented in FIG. 5, show that endothelial cell growth supplement (ECGS)-induced proliferation of HUVEC was inhibited similarly by the combination of free ALN+free TNP-470 and the HPMA copolymer-ALN-TNP-470 conjugate at ALN and TNP-470 equivalent concentrations, exhibiting an $IC_{50}$ of 0.7 and 1 nM, and had cytotoxic effect at doses higher than 1 and 10 nM, respectively.

Saos-2 human osteosarcoma cell proliferation was inhibited similarly by free and conjugated ALN and TNP-470 combinations at $IC_{50}$ of 30 μM.

MG-63-Ras human osteosarcoma cell proliferation was inhibited similarly by free and conjugated ALN-TNP-470 at $IC_{50}$ of 10 μM.

HPMA alone was inert in vitro and in vivo (data not shown), in agreement with previously published data [Duncan et al. *J Control Release* 2001; 74: 135-146].

In order to validate that HPMA copolymer-ALN-TNP-470 conjugate is active mainly upon the release of ALN and TNP-470 by cathepsin K cleavage mechanism, the inhibition of HUVEC proliferation by HPMA copolymer-ALN-TNP-470 conjugate in the presence of cathepsin K inhibitor III was evaluated. HPMA copolymer-ALN-TNP-470 conjugate inhibited the proliferation of HUVEC at a 4-logs higher concentration in the presence of cathepsin K inhibitor III than in its absence. Following 72 hours, there was probably some free ALN and TNP-470 released hydrolytically from HPMA copolymer-ALN-TNP-470 conjugate which led to the inhibition of proliferation of HUVEC at concentrations higher than 4 μM ALN-equivalent concentrations.

Example 6

Effect of HPMA Copolymer-ALN-TNP-470 Conjugate on Endothelial Cells Migration Towards the Chemoattractant VEGF The effect of HPMA copolymer ALN-TNP-470 conjugate on vascular endothelial growth factor (VEGF)-induced HUVEC migration was examined. Migration was assessed by counting the number of cells that migrated through the membranes towards the chemoattractant VEGF during a 4 hour period following 4 hours of treatment with a combination of free ALN+free TNP-470 or conjugated HPMA-ALN-TNP-470.

As shown in FIG. 6A, treatments with free or conjugated ALN/TNP-470 at equivalent concentrations of 0.1, 1, 10 nM dramatically inhibited the chemotactic migration response to VEGF by 23% ($p=0.038$), 41% ($p=0.003$), 58% ($p=0.013$), and 18% ($p=0.037$), 35% ($p=0.032$) and 61% ($p=0.0006$) respectively. HUVEC basal migration in the absence of VEGF was 33% compared to VEGF induced cells.

Example 7

Effect of HPMA Copolymer-ALN-TNP-470 Conjugate on Capillary-Like Tube Formation of HUVEC In Vitro The ability of HPMA copolymer-ALN-TNP-470 conjugate to inhibit capillary-like tube formation of HUVEC was examined.

As shown in FIG. 6C, the combination of free ALN+free TNP-470 and the conjugated HPMA-ALN-TNP-470 at equivalent concentrations of 0.01, 0.1, 1 nM inhibited capillary-like tube length compared with control (untreated) by 34% ($p=0.031$), 53% (0.007), 73% ($p=0.004$), and 29% ($p=0.021$), 54% (0.008) and 64% (0.014), respectively.

Example 8

HPMA Copolymer-ALN-TNP-470 Conjugate Reduces Vascular Hyperpermeability in Vivo

Both conjugates synthesized by classical and by RAFT polymerization reactions exhibited similar effects on the in vitro assays described hereinabove. Therefore, the narrowly dispersed and smaller in diameter RAFT-polymerized conjugate was chosen for all in vivo studies due to an expected improved biodistribution.

To determine whether HPMA copolymer-ALN-TNP-470 conjugate is able to reduce microvessel hyperpermeability a modified Miles assay was used. Evans blue dye was injected to the retro-orbital plexus and immediately thereafter the vascular permeability-induced factor VEGF was injected into the shaved flank of Balb/c mice. Evans blue binds to plasma proteins and therefore extravasates along with them at sites of increased permeability. VEGF-induced extravasation of Evans blue dye was remarkably inhibited in mice treated with free combination of ALN and TNP-470 and with HPMA copolymer-ALN-TNP-470 conjugate compared to vehicle treated mice by 87% ($P=0.002$) and 92% ($P=0.001$), respectively (see, FIGS. 7A and 7B respectively).

Example 9

HPMA Copolymer-ALN-TNP-470 Conjugate Inhibits MG-63-Ras Human Osteosarcoma In Vivo SCID male mice bearing s.c. mCherry-labeled MG-63-Ras human osteosarcoma showed decreased tumor growth rates when treated with free and conjugated ALN and TNP-470 (1:1, 30 mg/kg q.o.d. 3 times). The superiority of administering both drugs when conjugated to the polymer compared to a cocktail of both free drugs becomes evident when injected in vivo (FIG. 7D). HPMA copolymer-ALN-TNP-470 conjugate exhibited superior antitumor activity compared to free ALN and TNP-470 combination treatment. On day 19 when control mice were euthanized, HPMA copolymer-ALN-TNP-470 conjugate inhibited tumor growth by 96% ($p=0.001$) compared with 45% ($p=0.012$) of free ALN and TNP-470 (n=5 mice per group; (FIGS. 7C and 7D). Confocal microscopy analysis of mCherry-labeled tumors dissected from mice treated with FITC-labeled HPMA copolymer-ALN-TNP-470 conjugate revealed high accumulation of the conjugate at the tumor site (FIG. 7E).

H & E staining of tumor sections of MG-63-Ras human osteosarcoma tumors treated with combination of free TNP-470 and ALN or with the conjugate revealed that tumor sections from control mice consisted of poorly differentiated tumor cells invasive through the muscle layer with central calcified areas allowing the HA-targeting of the conjugate with ALN. Conjugate-treated tumors were almost regressed showing cholesterol deposits with connective tissue and giant cells and macrophages around them as signs of regression (FIG. 6F). CD34 staining (used as an endothelial cell marker) showed reduction of 39% ($p=5.5 \times 10^{-11}$) in microvessel density (MVD) of combination of free ALN with TNP-470 ($76 \pm 14$ microvessels/mm$^2$) and 74% ($P=4.7 \times 10^{-19}$) reduction in MVD of conjugate-treated tumors ($32 \pm 9$ microvessels/mm$^2$) vs. control group of mice ($125 \pm 16$ microvessels/mm$^2$) (n=5 mice per group; FIG. 6F).

Fluorescence imaging of organs dissected from mice treated with FITC-labeled HPMA copolymer-ALN-TNP-470 conjugate showed greater intensity of FITC-fluorescence spectrum (composed images of unmixed multispectral cubes) in bone tissues then in the spleen, heart, lungs, kidneys and liver (FIG. 6G). Some fluorescence is shown in the kidneys due to renal excretion of the conjugate.

Example 10

HPMA Copolymer-TNP-470 Conjugates with Octa-D-Aspartate as a Bone Targeting Moiety Two HPMA copolymer-TNP-470 conjugates with octa-D-aspartate as a bone targeting moiety are described herein (polymers denoted as HP1 and HP2). The samples containing aspartate were prepared using different polymer precursors, obtained either by "thermo" polymerization (AIBN as the initiator; HP1) or "photo" polymerization (HP2). The molecular weight profiles of these two polymers are different.

Synthesis of HPMA Copolymer-TNP-470 Conjugates Containing Octa-D-Aspartate Bone Targeting Group (HPMA-Asp8-TNP470) (HP1 and HP2)

The general synthesis of a HPMA-Asp8-TNP470 conjugate (Compound 6) according to some embodiments of the present invention is depicted in FIG. 8.

Synthesis of Trichlorophenoxy Active Ester of Methacrylate-Gly-Gly Containing Monomer [MA-GlyGly-OTcp; SEQ ID NO: 16 (compound 1)]:

MA-Gly-Gly-OH (SEQ ID NO: 15) (10 grams, 0.05 mol) and 2,4,5-trichlorophenol (12 grams, 0.06 mol) were dissolved in 100 ml DMF and cooled to (−5)-(−10)° C. Dicyclohexylcarbodiimide (DCC; 12.5 grams, 0.06 mol) in 50 ml DMF was added slowly, and the reaction mixture was stirred for 3 hours at (−5) to (−10)° C., overnight at 4° C., and 4 hours at room temperature. Acetic acid (about 0.5 ml) was then added and stirring continued for 1 hour. The DCU (dicyclohexylurea) was removed by filtration and the filtrate was slowly poured into about 800 ml of cooled water. The precipitate was filtered and dried under vacuum at room temperature. The product was purified by recrystallization from ethanol (dissolved in about 200 ml of boiling ethanol, then left to cool to room temperature, and placed into a refrigerator for crystallization). The product (crystals) was filtered, washed with a small amount of ethanol, and dried under vacuum thereby yielding 15 grams of the desired Compound 1 (79%).

m.p.=183-188° C.

Synthesis of Fmoc-Amine Containing Monomer [MA-GlyGlyProNle-NH(CH$_2$)$_2$NH-Fmoc (Compound 2; SEQ ID NO: 17)]:

MA-Gly-Gly-Pro-Nle-ethylenediamine (SEQ ID NO: 13) (100 mg) and diisopropylethylamine (DIPEA; 77 μl) were dissolved in 2 ml of THF and cooled to 0° C. Fmoc-Cl (115 mg) in 3 ml of THF was added slowly under stirring. The reaction mixture was stirred at room temperature for an additional 1 hour. Then the solvent was removed under vacuum, and the residue was purified by chromatography using a silica gel column with elution solvents: CHCl$_3$, followed by CHCl$_3$/MeOH 9/1 yielding the desired Compound 2.

Synthesis of FITC Labeled D-Asp$_8$ Containing Block (NH2-C6-GlyProNle-C6-Lys [FD8 (Compound 3; SEQ ID NO: 18)]:

FD8 (SEQ ID NO:18) was synthesized by solid phase peptide synthesis (SPPS) using 1 gram of 2-chlorotrityl chloride beads with 50% loading. The C6 spacer (1 amino hexanoic acid) was introduced to reduce the steric hindrance during the synthesis and the following binding reaction.

Synthesis of Polymer Precursor HPMA Containing TCP and Fmoc Protected Amino Groups [HPMA-OTcp-NH-Fmoc (Compound 4)]:

HPMA (200 mg), MA-Gly-Gly-Pro-Nle-ethylenediamine-Fmoc (Compound 2; 77 mg; SEQ ID NO:17), MA-Gly-Gly-OTcp (SEQ ID NO: 16; Compound 1; 44 mg), and 3 mg of AIBN were dissolved in 2.5 ml of DMSO and the solution was bubbled with N$_2$ for 10 minutes. The polymerization ampoule was sealed and polymerization proceeded at 50° C. for 24 hours. The polymer was precipitated into an excess of acetone and purified by dissolving in methanol and precipitating into acetone 3 times. The final product was dried under vacuum, yielding 260 mg of the desired Compound 4.

HPMA-OTcp-NH-Fmoc was also synthesized by photopolymerization, as follows: 2,2-Dimethoxy-2-phenylacetophenone (DMPAP; 40 mM), instead of AIBN, was used as the initiator. The polymerization was conducted under light (about 1000 lm/m$^2$) for 24 hours at room temperature. Purification was performed as described hereinabove for thermopolymerization.

Binding of FITC-D-ASP$_8$ (FD8; SEQ ID NO:18) Targeting Moiety to the HPMA Polymer [HPMA-FD8-NH-Fmoc (Compound 5)]:

HPMA-OTcp-NH-Fmoc (compound 4; 200 mg) was dissolved in 2.5 ml DMSO. FD8 (SEQ ID NO: 18; 130 mg) and DIPEA (130 μl), dissolved in 2 ml DMSO, were added and the reaction mixture was stirred overnight at room temperature. The polymer was precipitated into acetone, washed with acetone, and dried under vacuum yielding the desired compound 5.

Deprotection of Fmoc and Binding of TNP-470 to the HPMA-D-Asp$_8$ [P-FD8-TNP470 (Compound 6)]:

HPMA-FD8-NH-Fmoc (Compound 5; 150 mg) was dissolved in DMF (5 ml) and piperidine (1.2 ml) was added. The reaction mixture was stirred for 1 hour at room temperature. Then, the reaction mixture was acidified with acetic acid and precipitated into acetone (the polymer did not precipitate into acetone without acidifying). The copolymer was purified by washing 3 times with CHCl$_3$ to remove the piperidine-acetic acid salt, re-precipitated 3 times from methanol into acetone, and dried under vacuum. The polymer was further purified by FPLC (acetate buffer, pH 5.5). The polymer fraction was concentrated and pH adjusted to about 8 by NaHCO$_3$, followed by dialysis against DI water for 24 hours at 4° C. (MWCO 6-8 kDa) to remove the salt. The sample was freeze-dried after dialysis. HPMA-FD8-NH$_2$ (100 mg) was dissolved in DMF (3 ml) and cooled to 4° C. Then TNP-470 (100 mg) in 1 ml of DMF was added. The reaction mixture was stirred at 4° C. in dark for 12 hours. The conjugate was thereafter precipitated into acetone, and purified by dissolving in water and precipitating in acetone for 3 times; after each precipitation the precipitate was washed with acetone. The conjugate was further purified by FPLC (acetate buffer, pH 5.5), dialyzed for 1 day at 4° C. (MWCO 6-8 kDa) and freeze-dried yielding the desired HPMA-D-Asp$_8$-TNP-470 conjugate (Compound 6).

Example 11

Characterization of HPMA Copolymer-D-ASP$_8$-TNP-470 Conjugate (P-FD8-TNP470; SEQ ID NO:19)

Table 1 presents the chemical characteristics of the two HPMA-D-ASP$_8$-TNP-470 conjugates (HP1 and HP2; SEQ ID NO: 19), prepared as described in Example 10 hereinabove, with respect to the Asp$_8$ content, Fmoc (implying TNP470 content) and MW.

The Asp$_8$ content was determined by spectroscopy using FITC absorbance of the Asp$_8$ (using Σ495 nm=25300 M$^{-1}$cm$^{-1}$; borate pH 9.0; 35% FD8 contained FITC modified Lys).

Fmoc content was determined by spectroscopy using extinction coefficient Σ300 nm=6600 M$^{-1}$cm$^{-1}$ in MeOH; assuming that TNP-470 content is similar.

The molecular weight of the conjugate was determined by size exclusion chromatography (SEC) (see, FIG. 9) on AKTA/FPLC system (Pharmacia), using Superose 6 HR 10/30 column, buffer 0.1 M acetate/30% acetonitrile, pH 5.5.

TABLE 1

| Sample # | Structure | Asp$_8$ content mmol/g | Asp$_8$ content ~mol % | Fmoc content (=TNP470 content) mmol/g | Fmoc content (=TNP470 content) ~mol % | Mw (kDa) Mw/Mn | Amount mg | Note |
|---|---|---|---|---|---|---|---|---|
| HP1 | P-Asp$_8$-TNP-470 | 0.28 | 4.9 | 0.21 | 3.8 | 75 1.8 | 56 | "Thermo" polymerization |
| HP2 | P-Asp$_8$-TNP-470 | 0.15 | 2.7 | 0.28 | 5 | 20 1.6 | 31 | "photo" polymerization |

Example 12

Effect of HP1 and HP2 Conjugates on Growth Inhibition and Migration of HUVEC As an attempt to evaluate whether. TNP-470, when bound to HPMA copolymer, retained its antiangiogenic effect, proliferation and migration assays were performed.

The proliferation of HUVEC was inhibited similarly by free TNP-470 and conjugated TNP-470 (see, FIG. 10). The effect of HP1 and HP2 conjugates on vascular endothelial growth factor (VEGF)-induced HUVEC migration was examined. Migration was assessed by counting the number of cells that migrated through the membranes towards the chemoattractant VEGF during a 4 hour period following 4 hours of treatment with free TNP-470 or conjugated TNP-470.

As shown in FIG. 11, treatments with free or conjugated TNP-470 at equivalent concentrations of 0.1, 1 and 10 nM dramatically inhibited the chemotactic migration response to VEGF (see, FIG. 11A for HP1 and FIG. 11B for HP2). HUVEC basal migration in the absence of VEGF was 33% compared to VEGF induced cells.

Example 13

Alendronate Inhibits HUVEC and Saos-2 Human Sarcoma Cells Proliferation in a Dose Dependent Manner To determine whether the anti-angiogenic activity of alendronate is dose dependent, the inhibitory effect of the drug on HUVEC and Saos-2 human osteosarcoma cell proliferation was examined.

The results, presented in FIG. 12, show that endothelial cell growth supplement (ECGS)-induced proliferation of HUVEC (FIG. 12A) and Saos-2 human osteosarcoma cell proliferation (FIG. 12B) were inhibited at a dose dependent manner by free ALN and HPMA conjugated ALN (1 mol %).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A polymeric conjugate comprising an (N-(2-hydroxypropyl)methacrylamide) polymeric backbone comprised of a plurality of methacrylamide backbone units, said polymeric backbone having TNP-470 attached to a portion said backbone units and having alendronate attached to another portion said backbone units, wherein a load of said alendronate in the polymeric conjugate is greater than 3 mol %, wherein at least one of said TNP-470 and said alendronate is attached to said backbone units via a biodegradable linker.

2. The conjugate of claim 1, wherein said load of said alendronate is greater than 5 mol %.

3. The conjugate of claim 2, wherein said load of said alendronate is about 7 mol %.

4. The conjugate of claim 1, wherein said biodegradable linker is an enzymatically cleavable linker.

5. The conjugate of claim 4, wherein said enzymatically cleavable linker is cleaved by Cathepsin K.

6. The conjugate of claim 5, wherein said linker comprises a -[Gly-Gly-Pro-Nle]- oligopeptide.

7. The conjugate of claim 1, having the general formula II:

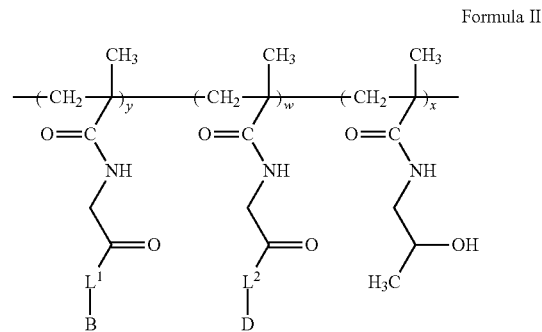

Formula II wherein:

B is said TNP-470;

D is said alendronate;

each of said $L_1$ and $L_2$ is independently said linker;

x is an integer having a value such that x/(x+y+w) multiplied by 100 is in the range of from 0.01 to 99.9;

y is an integer having a value such that y/(x+y+w) multiplied by 100 is in the range of from 0.01 to 99.9; and w is an integer having a value such that w/(x+y+w) multiplied by 100 is in the range of from 3 to 99.9.

8. The conjugate of claim 1, having the structure:

wherein:

x is an integer having a value such that x/(x+y+w) multiplied by 100 is in the range of from 0.01 to 99.9;

y is an integer having a value such that y/(x+y+w) multiplied by 100 is in the range of from 0.01 to 99.9; and w is an integer having a value such that w/(x+y+w) multiplied by 100 is in the range of from 3 to 99.9.

9. The conjugate of claim 7, wherein:

x is an integer having a value such that x/(x+y+w) multiplied by 100 is in the range of from 70 to 99.9;

y is an integer having a value such that y/(x+y+w) multiplied by 100 is in the range of from 0.01 to 15; and w is an integer having a value such that w/(x+y+w) multiplied by 100 is in the range of from 5 to 20.

10. The conjugate of claim 1, further comprising a labeling agent attached thereto.

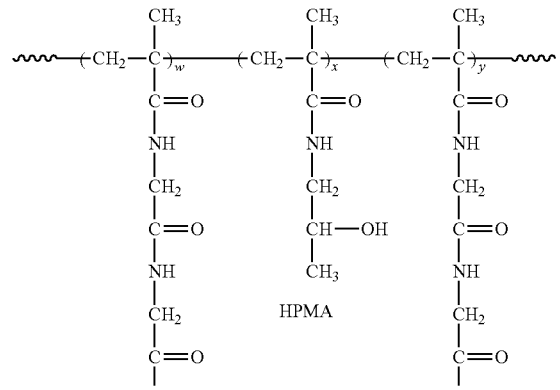

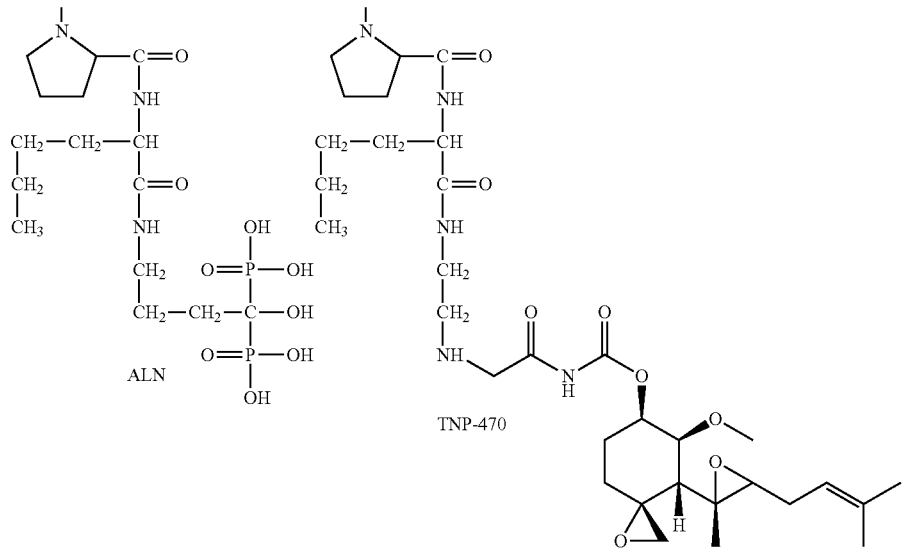

11. The conjugate of claim 10, having the structure:

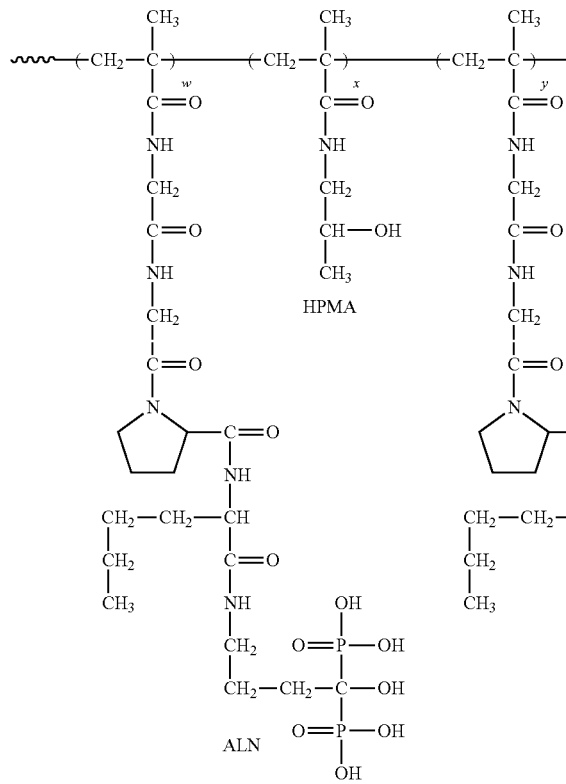
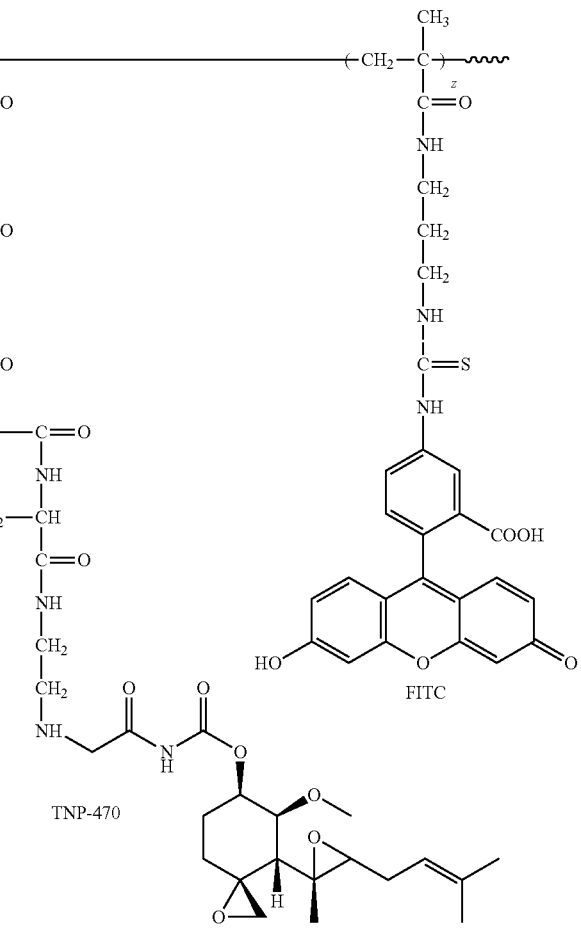

wherein:
  x is an integer having a value such that x/(x+y+w+z) multiplied by 100 is in the range from 0.01 to 99.9;
  y is an integer having a value such that y/(x+y+w+z) multiplied by 100 is in the range of from 0.01 to 99.9;
  w is an integer having a value such that w/(x+y+w+z) multiplied by 100 is in the range of from 3 to 99; and
  z is an integer having a value such that x/(x+y+w+z) multiplied by 100 is in the range of from 0.01 to 99.9.

12. The conjugate of claim 1, having a polydispersity index ranging from 1 to 1.4.

13. The conjugate of claim 1, having a mean size distribution lower than 150 nm.

14. A pharmaceutical composition comprising, as an active ingredient, the conjugate of claim 1 and a pharmaceutically acceptable carrier.

15. The pharmaceutical composition of claim 14, being packaged in a packaging material and identified in print, in or on said packaging material, for use in the treatment of, or in monitoring, a bone related disease or disorder.

16. The pharmaceutical composition of claim 15, wherein said disease or disorder is associated with angiogenesis.

17. The pharmaceutical composition of claim 16, wherein said disease or disorder is selected from the group consisting of bone metastases and bone cancer.

18. A method of treating a bone related disease or disorder in a subject in need thereof, the method comprising administering to the subject a therapeutically effective amount of the conjugate of claim 1.

19. The method of claim 18, wherein said disease or disorder is associated with angiogenesis.

20. The method of claim 19, wherein said disease or disorder is selected from the group consisting of bone metastases and bone cancer.

21. A method of monitoring a bone related disease or disorder in a subject, the method comprising:
  administering to the subject the conjugate of claim 10; and
  employing an imaging technique for monitoring a distribution of the conjugate within the body or a portion thereof.

22. The method of claim 21, wherein said disease or disorder is selected from the group consisting of bone metastases and bone cancer.

23. A process of synthesizing the conjugate of claim 1, the process comprising:
  (a) coupling alendronate to N-(2-hydroxypropyl)methacrylamide monomeric units, to thereby obtain alendronate-containing methacrylamide monomeric units;
  (b) co-polymerizing N-(2-hydroxypropyl)methacrylamide monomeric units, and/or ((N-(2-hydroxypropyl)methacrylamide) oligomeric or polymeric units with said alendronate-containing methacrylamide monomeric units and with methacrylamide monomeric units terminating with a first reactive group, to thereby obtain a polymeric backbone which comprises a plurality of methacrylamide backbone units in which a portion of the backbone units has an alendronate attached thereto, and another portion of the backbone units has said reactive group, said first reactive group being capable of coupling TNP-470; and (c) coupling said TNP-470 and said polymeric backbone via said first reactive group, thereby obtaining the polymeric conjugate.

24. The process of claim 23, wherein said co-polymerizing is performed via the Reversible addition-fragmentation chain transfer (RAFT) technique.

25. A polymeric conjugate comprising a polymeric backbone having attached thereto an anti-angiogenesis agent and a bone targeting moiety, said bone targeting moiety being an oligopeptide which comprises from 2 to 100 aspartic acid residues.

26. The polymeric conjugate of claim 25, wherein said polymeric backbone comprises a plurality of backbone units, 29. The conjugate of claim 25, wherein said aspartic acid is D-aspartic acid.

30. The conjugate of claim 25, wherein at least one of said anti-angiogenesis agent and said oligopeptide is attached to said polymeric backbone via a linker.

31. The conjugate of claim 25, wherein said polymeric backbone is derived from a polymer selected from the group consisting of dextran, a water soluble polyamino acid, a polyethylenglycol (PEG), a polyglutamic acid (PGA), a polylactic acid (PLA), a polylactic-co-glycolic acid (PLGA), a poly(D,L-lactide-co-glycolide) (PLA/PLGA), a poly(hydroxyalkylmethacrylamide), a polyglycerol, a polyamidoamine (PAMAM), and a polyethylenimine (PEI).

32. The conjugate of claim 25, further comprising a labeling agent attached thereto.

33. The conjugate of claim 32, having the structure:

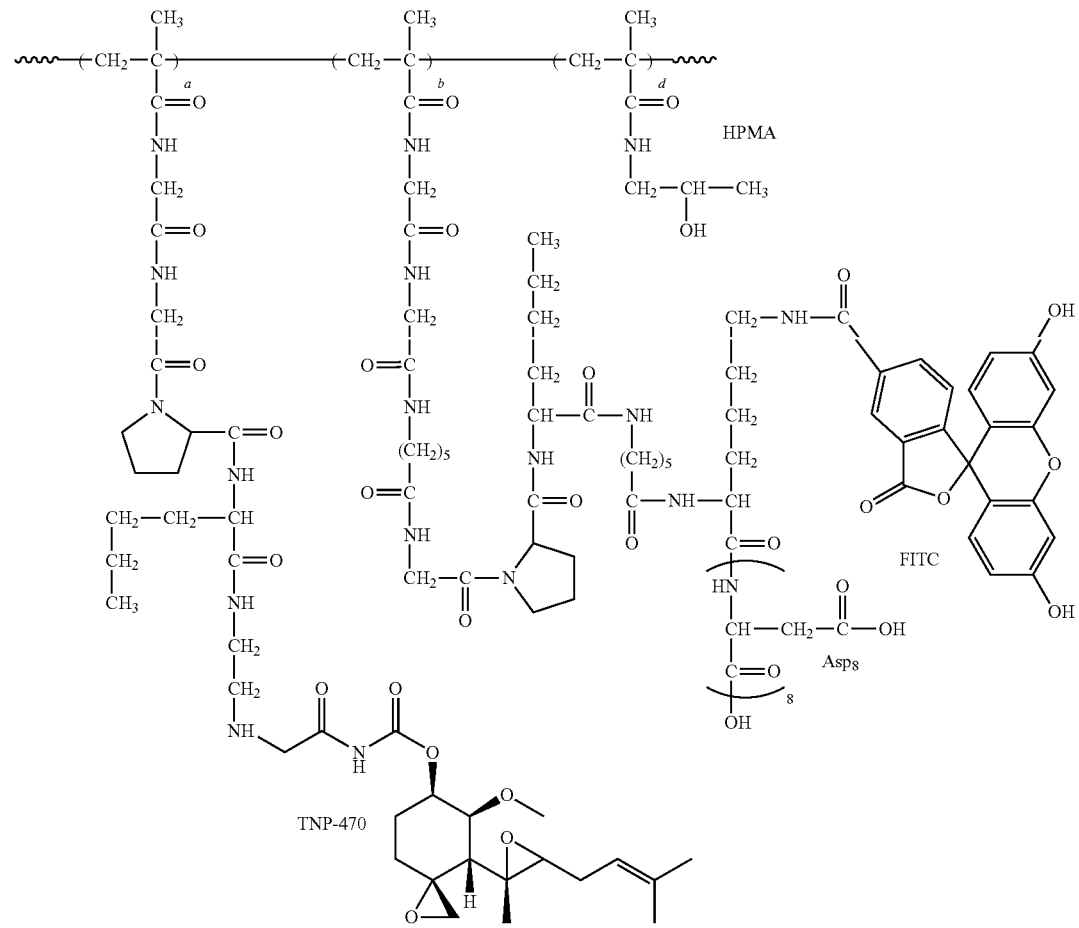

and wherein a portion of said plurality of backbone units has said anti-angiogenesis agent attached thereto and another portion of said plurality of backbone units has said oligopeptide of aspartic acid attached thereto.

27. The conjugate of claim 25, wherein said oligopeptide comprises from 2 to 20 aspartic acid residues.

28. The conjugate of claim 27, wherein said oligopeptide comprises 8 aspartic acid residues.

wherein:
a and b are each independently an integer having a value such that a/(a+b+d) multiplied by 100 and/or b/(a+b+d) x100 are in the range of from 0.01 to 15; and
d is an integer having a value such that d/(a+b+d) multiplied by 100 is in the range of from 70 to 99.9.

34. A pharmaceutical composition comprising, as an active ingredient, the conjugate of claim 25 and a pharmaceutically acceptable carrier.

35. The pharmaceutical composition of claim 34, being packaged in a packaging material and identified in print, in or on said packaging material, for use in the treatment of, or in monitoring, a bone related disease or disorder.

36. A method of treating a bone related disease or disorder in a subject in need thereof, the method comprising administering to the subject a therapeutically effective amount of the conjugate of claim 25.

37. A method of monitoring a bone related disease or disorder in a subject, the method comprising:
   administering to the subject the conjugate of claim 32; and
   employing an imaging technique for monitoring a distribution of the conjugate within the body or a portion thereof.

38. A process of synthesizing the conjugate of claim 25, the process comprising:
   (a) co-polymerizing a plurality of monomeric units of said polymeric backbone, wherein a portion of said plurality comprises monomeric units terminating by a first reactive group, and another portion of said plurality comprises monomeric units terminating by a second reactive group, to thereby obtain a co-polymer comprising a polymeric backbone that comprises a plurality of backbone units, wherein a portion of said backbone units has said first reactive group and another portion of said backbone units has said second reactive group, said first reactive group being capable of reacting with said anti-angiogenesis agent and said second reactive being capable of reacting with said bone targeting moiety;
   (b) coupling said bone targeting moiety to said co-polymer via said first reactive group, thereby obtaining a bone targeting moiety-containing copolymer; and
   (c) coupling said anti-angiogenesis agent to said co-polymer via said second reactive group, thereby obtaining the conjugate.

39. The process of claim 38, wherein said co-polymerizing is performed via the Reversible addition-fragmentation chain transfer (RAFT) technique.

* * * * *

```
SEQUENCE LISTING

<160> NUMBER OF SEQ ID NOS: 19

<210> SEQ ID NO 1
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(8)
<223> OTHER INFORMATION: D enantiomer

<400> SEQUENCE: 1

Asp Asp Asp Asp Asp Asp Asp Asp
1               5

<210> SEQ ID NO 2
<211> LENGTH: 4
<212> TYPE: PRT
```

```
<213> ORGANISM: Artificial sequence
<220> FEATURE:
<223> OTHER INFORMATION: Synthetic peptide

<400> SEQUENCE: 2

Gly Phe Leu Gly
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Nle

<400> SEQUENCE: 3

Gly Gly Pro Xaa
1

<210> SEQ ID NO 4
<211> LENGTH: 3
<212> TYPE: PRT
<213> ORGANISM: Artificial sequence
<220> FEATURE:
<223> OTHER INFORMATION: Synthetic peptide

<400> SEQUENCE: 4

Gly Phe Gly
1

<210> SEQ ID NO 5
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Nle

<400> SEQUENCE: 5

Gly Pro Xaa
1

<210> SEQ ID NO 6
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: 1 amino hexanoic acid spacer
<220> FEATURE:
<221> NAME/KEY: MOD_RES
<222> LOCATION: (6)..(6)
<223> OTHER INFORMATION: Nle

<400> SEQUENCE: 6

Gly Gly Xaa Gly Pro Xaa
1               5

<210> SEQ ID NO 7
<211> LENGTH: 4
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: MOD_RES
<222> LOCATION: (4)..(4)
<223> OTHER INFORMATION: Nle

<400> SEQUENCE: 7

Gly Gly Pro Xaa
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: MOD_RES
<222> LOCATION: (4)..(4)
<223> OTHER INFORMATION: Norleucine (Nle)
<220> FEATURE:
<221> NAME/KEY: misc_feature
<222> LOCATION: (4)..(4)
<223> OTHER INFORMATION: Alendronate conjugate

<400> SEQUENCE: 8

Gly Gly Pro Xaa
1

<210> SEQ ID NO 9
<211> LENGTH: 2
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate

<400> SEQUENCE: 9

Gly Gly
1

<210> SEQ ID NO 10
<211> LENGTH: 8
<212> TYPE: PRT
<213> ORGANISM: Artificial sequence
<220> FEATURE:
<223> OTHER INFORMATION: Synthetic peptide

<400> SEQUENCE: 10

Asp Asp Asp Asp Asp Asp Asp Asp
1               5

<210> SEQ ID NO 11
<211> LENGTH: 2
<212> TYPE: PRT
<213> ORGANISM: Artificial sequence
<220> FEATURE:
<223> OTHER INFORMATION: Synthetic peptide conjugate
```

```
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: misc_feature
<222> LOCATION: (2)..(2)
<223> OTHER INFORMATION: Protecting group conjugated through an oxygen
      on caboxylic end

<400> SEQUENCE: 11

Gly Gly
1

<210> SEQ ID NO 12
<211> LENGTH: 4
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-(2-hydroxypropyl)methacrylamide (HPMA)
      copolymer conjugate
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (4)..(4)
<223> OTHER INFORMATION: Alendronate(ALN)-TNP-470 conjugate

<400> SEQUENCE: 12

Gly Gly Pro Xaa
1

<210> SEQ ID NO 13
<211> LENGTH: 4
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (4)..(4)
<223> OTHER INFORMATION: NH(CH2)2NH2 conjugate

<400> SEQUENCE: 13

Gly Gly Pro Xaa
1

<210> SEQ ID NO 14
<211> LENGTH: 4
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: MOD_RES
<222> LOCATION: (4)..(4)
```

```
<223> OTHER INFORMATION: Nle
<220> FEATURE:
<221> NAME/KEY: misc_feature
<222> LOCATION: (4)..(4)
<223> OTHER INFORMATION: Hydroxyl group on end of peptide

<400> SEQUENCE: 14

Gly Gly Pro Xaa
1

<210> SEQ ID NO 15
<211> LENGTH: 2
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: misc_feature
<222> LOCATION: (2)..(2)
<223> OTHER INFORMATION: Hydroxyl group on end of peptide

<400> SEQUENCE: 15

Gly Gly
1

<210> SEQ ID NO 16
<211> LENGTH: 2
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: misc_feature
<222> LOCATION: (2)..(2)
<223> OTHER INFORMATION: O-TCP conjugate

<400> SEQUENCE: 16

Gly Gly
1

<210> SEQ ID NO 17
<211> LENGTH: 4
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: N-methacryloyl conjugate
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (4)..(4)
<223> OTHER INFORMATION: NH(CH2)2NH-FMOC conjugate

<400> SEQUENCE: 17

Gly Gly Pro Xaa
1

<210> SEQ ID NO 18
```

```
-continued

<211> LENGTH: 14
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: 1-amino hexanoic acid or hexanoic acid
<220> FEATURE:
<221> NAME/KEY: MOD_RES
<222> LOCATION: (4)..(4)
<223> OTHER INFORMATION: Nle
<220> FEATURE:
<221> NAME/KEY: misc_feature
<222> LOCATION: (5)..(5)
<223> OTHER INFORMATION: A spacer consisting of 1-aminohexanoic acid
<220> FEATURE:
<221> NAME/KEY: misc_feature
<222> LOCATION: (6)..(6)
<223> OTHER INFORMATION: FITC conjugate
<220> FEATURE:
<221> NAME/KEY: misc_feature
<222> LOCATION: (7)..(14)
<223> OTHER INFORMATION: D enantiomer

<400> SEQUENCE: 18

Xaa Gly Pro Xaa Xaa Lys Asp Asp Asp Asp Asp Asp Asp Asp
1               5                   10

<210> SEQ ID NO 19
<211> LENGTH: 8
<212> TYPE: PRT
<213> ORGANISM: Artificial sequence
<220> FEATURE:
<223> OTHER INFORMATION: Synthetic peptide conjugate
<220> FEATURE:
<221> NAME/KEY: misc_feature
<222> LOCATION: (1)..(1)
<223> OTHER INFORMATION: HPMA copolymer conjugate
<220> FEATURE:
<221> NAME/KEY: misc_feature
<222> LOCATION: (1)..(8)
<223> OTHER INFORMATION: D enantiomer
<220> FEATURE:
<221> NAME/KEY: misc_feature
<222> LOCATION: (8)..(8)
<223> OTHER INFORMATION: TNP-470 conjugate

<400> SEQUENCE: 19

Asp Asp Asp Asp Asp Asp Asp Asp
1               5
```